United States Patent
Gong et al.

(10) Patent No.: US 7,371,874 B2
(45) Date of Patent: *May 13, 2008

(54) 6-ALKYLAMINO-2-METHYL-2'-(N-METHYL SUBSTITUTED SULFONAMIDO)METHYL-2H-1-BENZOPYRAN DERIVATIVE AS ANTI-INFLAMMATORY INHIBITOR

(75) Inventors: Young-Dae Gong, Daejeon (KR); Hyae-Gyeong Cheon, Daejeon (KR); Moon-Kook Jeon, Daejeon (KR); Cho Young Sik, Daejeon (KR); Jong Yeon Hwang, Jeollabuk-do (KR); Choi Hyung Sub, Daejeon (KR); Jeon Hyun Suk, Gwangju (KR); Soon-Hee Hwang, Daejeon (KR); Song Jin Sook, Daejeon (KR); Kim Chi Hyun, Daejeon (KR); Sung-eun Yoo, Gongju-si (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/491,320

(22) Filed: Jul. 21, 2006

(65) Prior Publication Data
US 2007/0049621 A1    Mar. 1, 2007

(30) Foreign Application Priority Data
Aug. 30, 2005   (KR) .................. 10-2005-0080383

(51) Int. Cl.
*C07D 311/00*    (2006.01)
*C07D 405/00*    (2006.01)
*A61K 31/35*    (2006.01)
*A61K 31/46*    (2006.01)

(52) U.S. Cl. .................... 549/404; 549/60; 549/365; 546/282.7; 546/283.1; 514/457; 514/456; 514/444; 514/337

(58) Field of Classification Search ................ 549/404, 549/60, 365; 546/282.7, 283.1; 514/457, 514/456, 444, 337
See application file for complete search history.

(56) References Cited

U.S. PATENT DOCUMENTS

| | | | | |
|---|---|---|---|---|
| 5,646,308 A | * | 7/1997 | Koga et al. | 549/404 |
| 5,696,137 A | * | 12/1997 | Heine et al. | 514/322 |
| 6,395,909 B1 | * | 5/2002 | Bell et al. | 549/404 |

* cited by examiner

*Primary Examiner*—Janet L. Andres
*Assistant Examiner*—Raymond Covington
(74) *Attorney, Agent, or Firm*—Frommer Lawrence & Haug LLP; Ronald R. Santucci

(57) ABSTRACT

The present invention relates to a noble 6-alkylamino-2-methyl-2'-(N-methyl substituted sulfonamido)methyl-2H-1-benzopyran derivative, a method for preparing the same with high efficiency using a parallel synthetic method, one of combinatorial chemical synthetic techniques, and a use of the novel compound showing a high inhibitory effect to 5-lipoxygenase (5-LO) activity for preventing and treating leukotriene (LTA4, B4, C4, D4) activation-related diseases such as inflammatory diseases, rheumatoid arthritis, colitis, asthma and psoriasis.

4 Claims, No Drawings

6-ALKYLAMINO-2-METHYL-2'-(N-METHYL SUBSTITUTED SULFONAMIDO)METHYL-2H-1-BENZOPYRAN DERIVATIVE AS ANTI-INFLAMMATORY INHIBITOR

This application claims priority benefits from Korean Patent Application No. 10-2005-0080383 filed Aug. 30, 2005.

TECHNICAL FIELD

The present invention relates to a noble 6-alkylamino-2-methyl-2'-(N-methyl substituted sulfonamido)methyl-2H-1-benzopyran derivative, a method for preparing the same with high efficiency using a parallel synthetic method, one of combinatorial chemical synthetic techniques, and a use of the novel compound showing a high inhibitory effect to 5-lipoxygenase (5-LO) activity for preventing and treating leukotriene (LTA4, B4, C4, D4) activation-related diseases such as inflammatory diseases, rheumatoid arthritis, colitis, asthma and psoriasis.

BACKGROUND ART

5-LO is an enzyme involved in the arachidonic acid metabolism. It synthesizes leukotriene by acting on the generation of 5-HPETE from arachidonic acid. LTB4, the most powerful chemoattractant among synthesized leukotrienes, is a major cause of several diseases such as chronic inflammation, rheumatoid arthritis, allergy, asthma and psoriasis. When the cell content of leukotriene increases, inflammatory cells are activated, causing such inflammatory diseases as chronic inflammation and rheumatism. Also, endotoxins resulting from tissue damage or bacterial infection cause acute or chronical damage of the corresponding tissue and organ.

Therefore, by developing a 5-LO inhibitor capable of preventing tissue and organ damages by inhibiting the activation of inflammatory cells caused by the increase in cellular leukotriene, it is possible to prevent or treat several inflammation-related diseases.

Since some natural products and synthetic compounds having a 2'-sulfonamidomethylbenzopyran backbone show an antioxidant activity, they have been widely known as a privileged structure for developing a pharmacological therapeutic compound effective for treating nerve diseases, hypertension and diabetes and broadly employed in the medicinal chemistry field. However, there is no report that a compound having 2'-sulfonamidomethylbenzopyran moiety as a privileged structure has been developed as an anti-inflammatory agent.

Construction of a benzopyran library having various derivatives using the combinatorial chemical synthetic technique can be effectively used for screening biological hit compounds and lead compounds at the early stage of a noble drug development.

Particularly, it is very important to efficiently construct a large and focused library of small organic molecules, which enable introduction of various derivatives without significantly deviating from the range of Rule of 5 by Lipinsky, with regard to molecular varieties effective for screening lead compounds.

The combinatorial chemical synthesis is a new synthetic method for developing a new compound. While the conventional organic synthetic methods can synthesize one kind of compound via a single reaction, the combinatorial chemical synthetic technique is a highly efficient method which can synthesize more various and numerous compounds at the same time or automate the multi-step synthetic process. With the technique, it has become easier to screen a biological hit compound and a lead compound having a new structure and optimize structure and activity thereof.

Since the combinatorial chemical synthetic technique carries out most of the reaction procedures on a solid support, successive multi-step reaction and automated reaction are possible. In addition, a high throughput screening (HTS) is made possible because the steps of isolation and purification of products are very simple in this method.

Although the combinatorial chemical synthetic technique solves the uneconomic and inefficient problems of conventional synthetic methods, there are several reasons why this method is not readily applied to the organic synthetic field. One of the representative reasons is that an undesirable side reaction occurs because reagents are used in excessive amounts in most of chemical reactions performed on a solid support and that the range of applicable chemical reactions is limited because employable solvents are restricted depending on the physical property of the solid support. The Merrifield resin and the Wang resin are widely employed as solid support in the combinatorial chemical synthesis. Since these solid supports show a significantly low swelling effect in highly polar solvents such as alcohol and water, selection of reaction solvents is very limited. Accordingly, in order to synthesize various derivatives through solid-phase reaction, selection of a solid support and a linker, optimization of reagents and reaction conditions and selection of a substituent group capable of diversely changing the chemical structure and physical property of the target compound are important factors. Therefore, in order to construct a target compound library using the solid-phase combinatorial chemical synthetic technique, it is necessary to efficiently develop a reaction condition adequate for the characteristics of the target compound and a post-reaction treatment procedure.

DISCLOSURE OF THE INVENTION

The present inventors have found that a 2'-sulfonamidomethylbenzopyran derivative significantly inhibits 5-LO activity. Further, the present inventors have endeavored to develop an optimized technique for screening a lead compound by mass production of a 2'-sulfonamidomethylbenzopyran library using a combinatorial chemical synthetic technique on solid phase. As a result, the present inventors completed the present invention by finding out that, while conventional chemical reactions on solution phase require synthesis of a target compound by carrying out each reaction step for introducing a substituent group, purification after the reaction and structure confirmation, a large amount of 6-alkylamino-2-methyl-2'-(N-methyl substituted sulfonamido)methyl-2H-1-benzopyran library having various substituents, or the target compounds, can be produced economically in a short period of time with high yields by performing several reactions at the same time and an efficient treatment after the reaction, through a combinatorial chemical synthetic technique using a solid-phase parallel synthetic method.

Accordingly, it is an object of the present invention to provide a 6-alkylamino-2-methyl-2'-(N-methyl substituted sulfonamido)methyl-2H-1-benzopyran derivative having a novel structure.

It is another object of the present invention to provide a method for preparing a 6-alkylamino-2-methyl-2'-(N-methyl substituted sulfonamido)methyl-2H-1-benzopyran derivative using a solid-phase parallel synthetic method whose advantage is that the chemical structure of the final product can be easily analyzed via an automatic reaction procedure and purification step and that production yield is high.

It is still another object of the present invention to provide a use of the 6-alkylamino-2-methyl-2'-(N-methyl substituted sulfonamido)methyl-2H-1-benzopyran derivative showing a high inhibitory effect to 5-LO activity for preventing and treating various inflammatory diseases caused by the inflammatory cell activation due to the increase of cellular leukotriene, including chronic inflammation, rheumatism and arthritis.

BEST MODE FOR CARRYING OUT THE INVENTION

The present invention is characterized by a 6-alkylamino-2-methyl-2'-(N-methyl substituted sulfonamido)methyl-2H-1-benzopyran derivative represented by the formula 1 below:

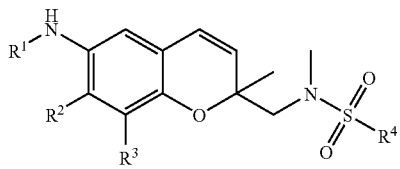

(1)

wherein $R^1$ is $C_1$-$C_{10}$ alkyl; phenyl; phenyl substituted with a substituent selected from the group consisting of $C_1$-$C_6$ alkyl, $C_1$-$C_6$ acyloxy, $C_1$-$C_{10}$ alkoxyalkyl and $C_1$-$C_{10}$ dialkoxyalkyl; benzyl; benzyl substituted with a substituent selected from the group consisting of halogen, nitro, cyano, hydroxy, $C_1$-$C_6$ alkyl and $C_1$-$C_6$ alkoxy; phenethyl; pyridylmethyl; thiophenemethyl; or thiophenemethyl substituted with $C_1$-$C_6$ alkyl, each of $R^2$ and $R^3$ is a hydrogen atom; or $C_1$-$C_6$ alkyl and $R^4$ is $C_1$-$C_{10}$ alkyl; phenyl; phenyl substituted with a substituent selected from the group consisting of halogen, $C_1$-$C_6$ alkyl and $C_1$-$C_6$ alkoxy; benzyl; or thiophene.

Since the 6-alkylamino-2-methyl-2'-(N-methyl substituted sulfonamido)methyl-2H-1-benzopyran derivative represented by the formula 1 has a chiral carbon, the present invention also includes a racemic compound or each isomeric compound isolated by a conventional method and mixtures thereof.

Hereinafter, the present invention is described in further detail.

The present invention is characterized by a 6-alkylamino-2-methyl-2'-(N-methyl substituted sulfonamido)methyl-2H-1-benzopyran derivative represented by the formula 1, a method for preparing the same by a combinatorial chemical synthetic technique which can efficiently synthesize the novel benzopyran derivative using solid-phase parallel synthetic method rather than solution-phase chemical reaction and a use of the novel compound for preventing and treating diseases caused by the activation of inflammatory cells due to the increase of cellular leukotrienes.

A preferred compound of the present invention is a 6-alkylamino-2-methyl-2'-(N-methyl substituted sulfonamido)methyl-2H-1-benzopyran derivative or an isomeric compound thereof, which is represented by the formula 1, wherein $R^1$ is $C_1$-$C_6$ alkyl; phenyl; phenyl substituted with a substituent selected from the group consisting of $C_1$-$C_4$ alkyl, acetyl and diethoxymethyl; benzyl; benzyl substituted with a substituent selected from the group consisting of halogen, nitro, cyano, hydroxy, $C_1$-$C_4$ alkyl and $C_1$-$C_4$ alkoxy; phenethyl; pyridylmethyl; thiophenemethyl; or thiophenemethyl substituted with $C_1$-$C_4$ alkyl, each of $R^2$ and $R^3$ is a hydrogen atom; or $C_1$-$C_4$ alkyl and $R^4$ is $C_1$-$C_6$ alkyl; phenyl; phenyl substituted with a substituent selected from the group consisting of halogen, $C_1$-$C_4$ alkyl and $C_1$-$C_4$ alkoxy; benzyl; or thiophene.

A method for preparing the 6-alkylamino-2-methyl-2'-(N-methyl substituted sulfonamido)methyl-2H-1-benzopyran derivative represented by the formula 1 using a combinatorial chemical synthetic technique according to the present invention is briefly described in the following scheme 1:

Scheme 1

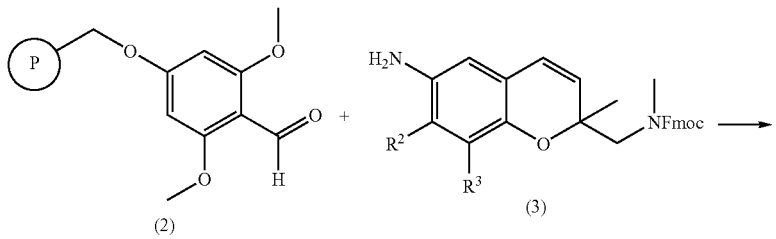

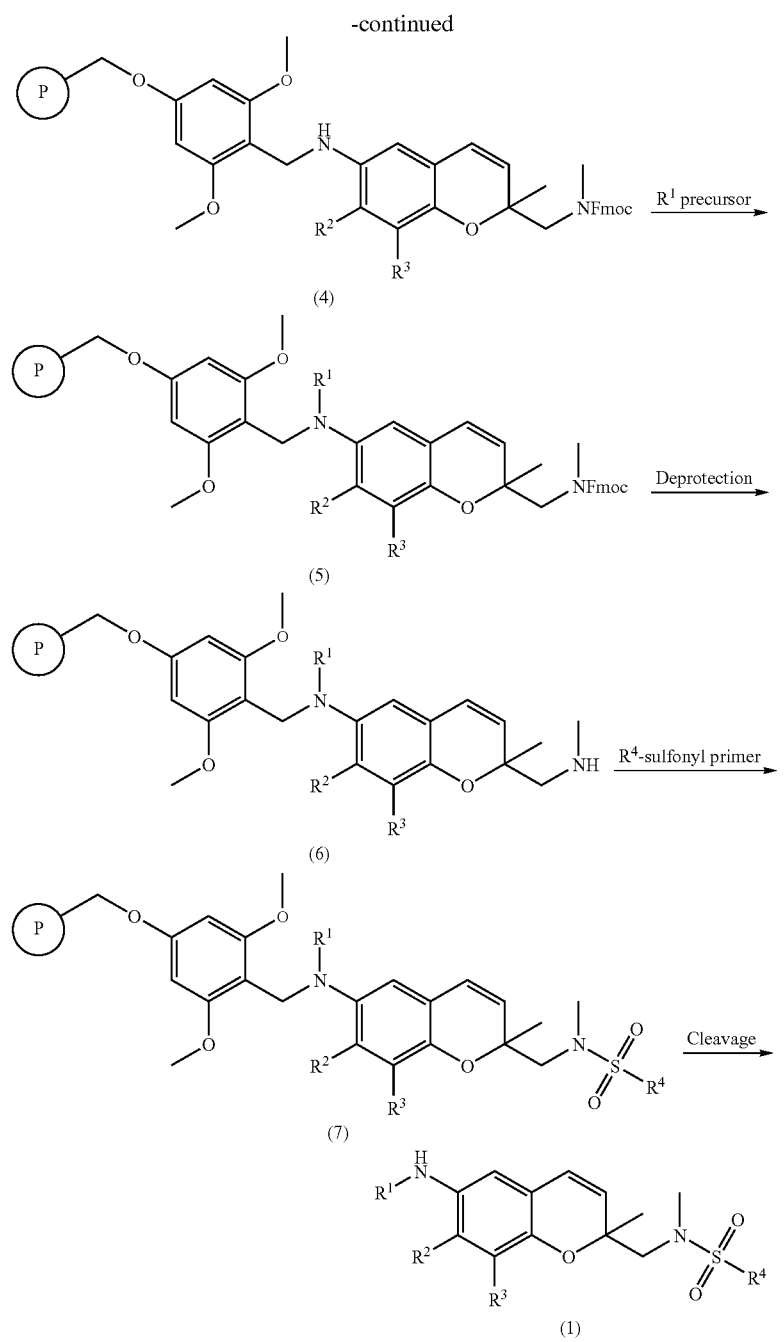

wherein, $R^1$, $R^2$, $R^3$ and $R^4$ are the same as defined above; and Ⓟ is a solid support in the form of a high molecular weight polymer selected from the group consisting of polystyrene-divinylbenzene, methacrylic acid-dimethylacrylamide and hydroxyl methacrylic acid.

The reaction intermediates in the preparation method according to the present invention, or 6-amino-2-methyl-2'-(Fmoc protected methylamino)methyl-2H-1-benzopyran resin represented by the formula 4,6-alkylamino-2-methyl-2'-(Fmoc protected methylamino)methyl-2H-1-benzopyran resin represented by the formula 5,6-alkylamino-2-methyl-2'-(methylamino)methyl-2H-1-benzopyran resin represented by the formula 6 and 6-alkylamino-2-methyl-2'-(N-methyl substituted sulfonamido)methyl-2H-1-benzopyran resin represented by the formula 7 are also optical isomers and thus it is possible to isolate them as isomeric compounds, if necessary.

The preparation method of the present invention according to Scheme 1 comprises the following 5 steps of:

synthesizing 6-amino-2-methyl-2'-(Fmoc protected methylamino)methyl-2H-1-benzopyran resin represented by the formula 4 by introducing 6-amino-2-methyl-2'-(Fmoc protected methylamino)methyl-2H-7,8-disubstituted benzopyran represented by the formula 3 to a solid support coupled with a backbone amide linker (BAL linker) represented by the formula 2 (the first step);

synthesizing 6-alkylamino-2-methyl-2'-(Fmoc protected methylamino)methyl-2H-1-benzopyran represented by the formula 5 by selectively introducing the $R^1$ substituent to the nitrogen atom of 6-amino-2-methyl-2'-(Fmoc protected methylamino)methyl-2H-1-benzopyran resin represented by the formula 4 (the second step);

synthesizing 6-alkylamino-2-methyl-2'-(methylamino) methyl-2H-1-benzopyran resin represented by the formula 6 by deprotection of the Fmoc protecting group of 6-alkylamino-2-methyl-2'-(Fmoc protected methylamino)methyl-2H-1-benzopyran represented by the formula 5 with an organic base selected from the group consisting of alkylamine, pyridine and piperidine (the third step);

synthesizing 6-alkylamino-2-methyl-2'-(N-methyl substituted sulfonamido)methyl-2H-1-benzopyran resin represented by the formula 7 by selectively introducing the $R^4$ sulfonyl substituent to the nitrogen atom of 6-alkylamino-2-methyl-2'-(methylamino)methyl-2H-1-benzopyran resin represented by the formula 6 (the fourth step); and synthesizing a 6-alkylamino-2-methyl-2'-(N-methyl substituted sulfonamido)methyl-2H-1-benzopyran library represented by the formula 1, the final target compound, by cleaving the 6-alkylamino-2-methyl-2'-(N-methyl substituted sulfonamido)methyl-2H-1-benzopyran resin compound represented by the formula 7 with a dichloromethane solution containing trifluoroacetate (TFA) or an organic solvent containing an organic acid (the fifth step).

According to the finding of the present inventors, when two rounds of N-alkylation are carried out via a parallel synthetic method using the 6-amino-2-methyl-2'-(Fmoc protected methylamino)methyl-2H-1-benzopyran resin coupled with a BAL linker on a solid support represented by the formula 4 and the 6-alkylamino-2-methyl-2'-(methylamino) methyl-2H-1-benzopyran resin represented by the formula 6, it is possible to conduct tens to hundreds of reactions and purifications at the same time, which enables synthesis of various 6-alkylamino-2-methyl-2'-(N-methyl substituted sulfonamido)methyl-2H-1-benzopyran derivatives in a short period of time.

The reaction procedures, solvent system compositions and reaction conditions in the steps of the present invention are described in detail as follows.

An organic solvent showing excellent swelling effect on Wang resin or Merrifield resin is used as solvent in the present invention.

The first step is a procedure of reductive amination and dimethylformamide (DMF) containing 1% acetic acid is used as solvent. For the reducing agent, it is preferable to use $NaBH(OAc)_3$ in amount of about 3 equivalents, and more economically preferably, about 2 equivalents.

The second step is a procedure of selectively introducing the $R^1$ substituent to the nitrogen atom of 6-amino group and DMF is used as solvent. It is preferable to use a base and the $R^1$ substituent in amount of about 3 equivalents respectively, and more economically preferably, about 2 equivalents. At this time, an organic amine base may be used as the base. Preferably, the organic amine base is one having large steric hindrance, e.g., diisopropylethylamine (DIPEA).

The third step is a procedure of deprotecting the 2'-Fmoc protecting group. An organic solvent containing an organic base selected from the group consisting of alkylamine, pyridine and piperidine is used as solvent. Preferably, DMF containing 20% piperidine is used.

The fourth step is a procedure of selectively introducing the $R^4$ sulfonyl substituent to the nitrogen atom of 2'-aminomethyl group and DMF is used as solvent. It is preferable to use an organic base, e.g., triethylamine, and an $R^4$ sulfonyl precursor in amount of about 3 equivalents respectively, and more economically preferably, about 2 equivalents.

The fifth step is a procedure of cleaving a final target product from the solid support. An organic solvent containing an organic acid is used as solvent, and preferably, dichloromethane containing 20% TFA is used.

Further, in order to confirm the synthesis of 6-alkylamino-2-methyl-2'-(N-methyl substituted sulfonamido)methyl-2H-1-benzopyran derivative represented by the formula 1 in accordance with the present invention, the target compound cleaved from 6-alkylamino-2-methyl-2'-(N-methyl substituted sulfonamido)methyl-2H-1-benzopyran resin represented by the formula 7 was purified and isolated by flash column chromatography and its structure was analyzed and identified with NMR and mass spectroscopy. The progress of reaction was monitored by ATR-FTIR of the resins represented by the formula 2, 4, 5, 6 and 7, or the reaction intermediates.

The compounds of the present invention show a high inhibitory effect to 5-LO activity and thus they can be efficiently used for preventing and treating inflammatory diseases caused by activation of the leukotriene-related receptor. Thus, the compounds of the present invention can be used as a drug for preventing or treating rheumatism, asthma and allergy caused by activation of inflammatory cells.

Therefore, the present invention includes a pharmaceutical composition for preventing and treating various diseases caused by the promotion of 5-LO or activation of inflammatory cells, which comprises the 6-alkylamino-2-methyl-2'-(N-methyl substituted sulfonamido)methyl-2H-1-benzopyran derivative represented by the formula 1 or a pharmaceutically acceptable salt thereof.

The pharmaceutically acceptable salt of the present invention can be prepared by a conventional method well-known in the art. For example, the pharmaceutically acceptable salt may be prepared in the form of an acidic salt by reaction with an inorganic acid such as hydrochloric acid, hydrogen bromide, sulfuric acid, sodium hydrogen sulfate, phosphoric acid and carbonic acid or an organic acid such as formic acid, acetic acid, oxalic acid, benzoic acid, citric acid, tartaric acid, gluconic acid, gestisic acid, fumaric acid, lactobionic acid, salicylic acid and acetylsalicylic acid (aspirin). The pharmaceutically acceptable salt may be also prepared in the form of a metal salt by reaction with an alkali metal ion such as sodium and potassium or in the form of another pharmaceutically acceptable salt by reaction with an ammonium ion.

Further, the pharmaceutical composition of this invention, which is prepared by adding a commonly used non-toxic pharmaceutically acceptable carrier, reinforcing agent, vehicle, etc. to the 6-alkylamino-2-methyl-2'-(N-methyl substituted sulfonamido)methyl-2H-1-benzopyran derivative or pharmaceutically acceptable salt thereof, may be formulated in the form of a conventional formulation, for example, an oral drug such as tablet, capsule, troche, solution and suspension or a non-oral drug. The administration dosage of the compound of the present invention for humans may vary depending on the age, body weight, sex and physical condition of the patient, severity of disease and administration type. A general dosage is 0.01-1000 mg/day for an adult patient weighing 70 kg and the pharmaceutical composition may be administered in a single dose or in a divided dose, according to the instruction of a physician or a pharmacist.

Hereinafter, the present invention is described in further detail through examples. The formulas of the representative compounds and biological examination test results for 5-LO inhibitory effect are shown in Table 1 and Table 2 below, respectively. However, the following examples are only for the understanding of the invention and the invention is not limited to or by them.

EXAMPLE I

Synthesis and confirmation of 6-amino-2-methyl-2'-(Fmoc protected methylamino)methyl-2H-1-benzopyran resin (formula 4)

I-1: Synthesis and confirmation of 6-amino-2-methyl-2'-(Fmoc protected methylamino)methyl-2H-1-benzopyran resin

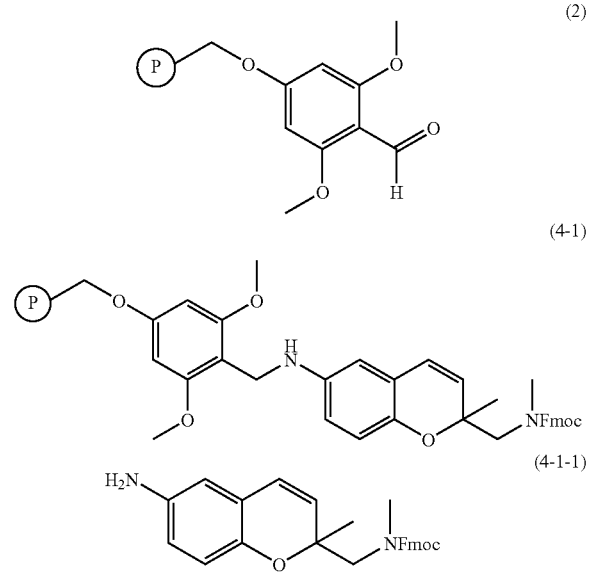

A BAL resin (1.6 mmol/g, 10 g, 16.0 mmol) represented by the formula 2 was added to 100 mL of DMF containing 1% acetic acid and then 6-amino-2-methyl-2'-(Fmoc protected methylamino)methyl-2H-1-benzopyran (13.65 g, 32.0 mmol) and sodium triacetoxyboron hydride (NaBH(OAc)$_3$, 6.78 g, 32.0 mmol) were successively added thereto. The reaction mixture was shaken for 15 hours for mixing. After the completion of reaction, the reaction mixture was filtered and washed repeatedly with DMF, MC, MC/MeOH (1/1, v/v) and MeOH to obtain a solid resin (formula 4-1; 11.5 g) (ATR-FTIR; carbamate: 1700 cm$^{-1}$).

The obtained resin (formula 4-1; 0.200 g, 0.16 mmol) was added to 5 mL of dichloromethane (DCM) and then 1 mL of TFA was added thereto. The reaction mixture was shaken at room temperature for 4 hours. After the completion of reaction, the reaction mixture was filtered and washed repeatedly with DCM and MeOH. The washed solution and the filtrate were combined and then concentrated. After 3 mL of ethylacetate was added to the concentrated mixture, the reaction mixture was filtered with a strong anion exchange resin (SAX resin) and washed repeatedly with ethylacetate to remove residual TFA. After concentration under reduced pressure, the concentrate was isolated and purified by silica gel column chromatography using a solvent mixture of hexane/ethylacetate (4/1, v/v) to obtain an oil represented by the formula 4-1-1 (93.8 mg, 69%; loading capacity of resin 4-1=1.1 mmol/g).

I-2: Synthesis and confirmation of 6-amino-2,7-dimethyl-2'-(Fmoc protected methylamino)methyl-2H-1-benzopyran resin

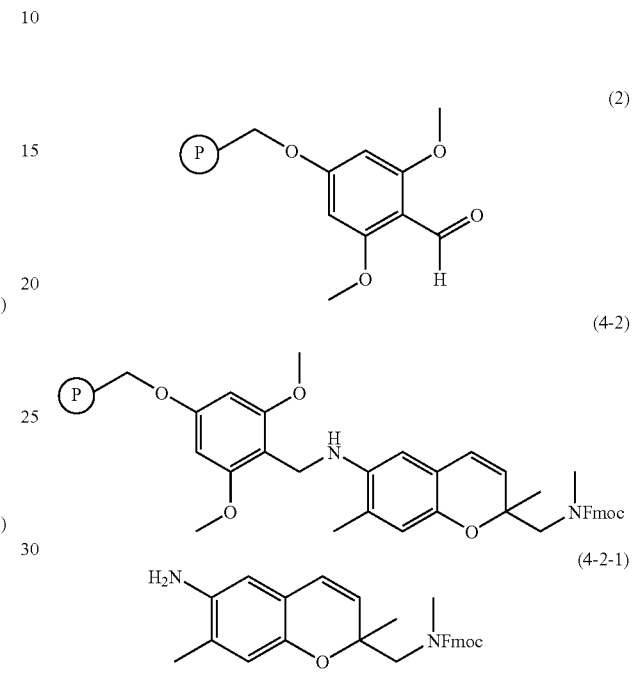

A BAL resin (1.6 mmol/g, 10 g, 16.0 mmol) represented by the formula 2 was added to 100 mL DMF containing 1% acetic acid and then 6-amino-2,7-dimethyl-2'-(Fmoc protected methylamino)methyl-2H-1-benzopyran (14.10 g, 32.0 mmol) and sodium triacetoxyboron hydride (NaBH(OAc)$_3$, 6.78 g, 32.0 mmol) were successively added thereto. The reaction mixture was shaken for 15 hours for mixing. After the completion of reaction, the reaction mixture was filtered and washed repeatedly with DMF, MC, MC/MeOH (1/1, v/v) and MeOH to obtain a solid resin (formula 4-2; 11.4 g) (ATR-FTIR; carbamate: 1700 cm$^{-1}$).

The obtained resin (formula 4-2; 0.200 g, 0.16 mmol) was added to 5 mL of DCM and then 1 mL of TFA was added thereto. The reaction mixture was shaken at room temperature for 4 hours. After the completion of reaction, the reaction mixture was filtered and washed repeatedly with DCM and MeOH. The washed solution and the filtrate were combined and then concentrated. After 3 mL of ethylacetate was added to the concentrated mixture, the reaction mixture was filtered with a strong anion exchange resin (SAX resin) and washed repeatedly with ethylacetate to remove residual TFA. After concentration under reduced pressure, the concentrate was isolated and purified with a silica gel column chromatography using a solvent mixture of hexane/ethylacetate (4/1, v/v) to obtain an oil represented by the formula 4-2-1 (88.1 mg, 63%; loading capacity of resin 4-2=1.0 mmol/g).

EXAMPLE II

N-alkylation using 6-amino-2-methyl-2'-(Fmoc protected methylamino)methyl-2H-1-benzopyran resin (formula 4)

II-1: N-benzylation and Fmoc deprotection of 6-amino-2-methyl-2'-(Fmoc protected methylamino)methyl-2H-1-benzopyran resin II-2: N-benzylation and Fmoc deprotection of 6-amino-2,7-dimethyl-2'-(Fmoc protected methylamino)methyl-2H-1-benzopyran resin

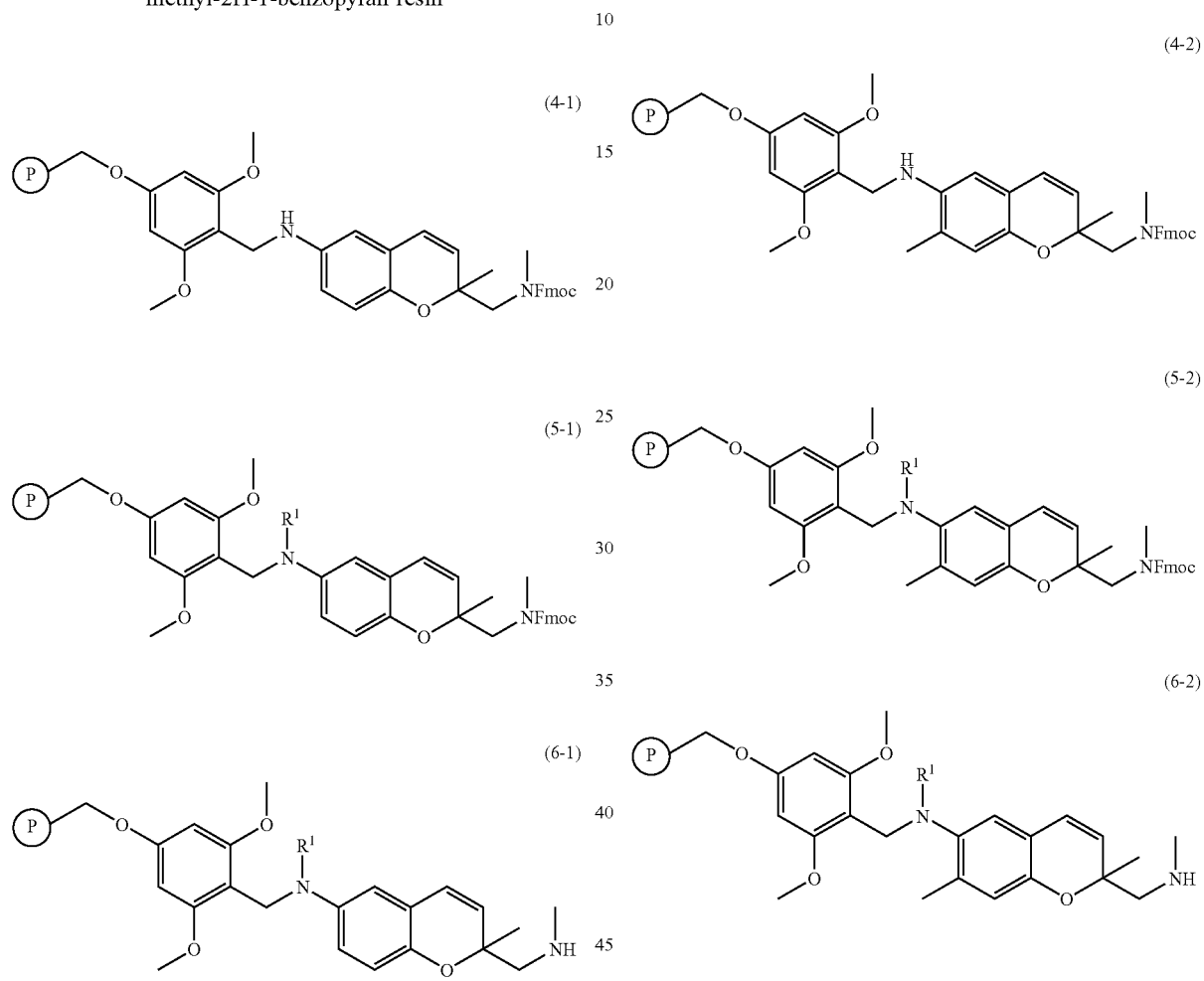

A benzopyran resin (0.200 g, 0.22 mmol) represented by the formula 4-1 was added to 3 mL of DMF and the reaction mixture was shaken at room temperature for 10 minutes. Then, benzyl bromide (BnBr; 0.12 mL, 0.66 mmol) and diisopropylamine (0.092 mL, 0.66 mmol) were added and the reaction mixture was shaken at room temperature for 15 hours for mixing. After the completion of reaction, the reaction mixture was filtered and washed repeatedly with DMF, MC, MC/MeOH and MeOH to obtain a light-brown solid resin (formula 5-1).

The obtained resin (formula 5-1) was added to 5 mL of DMF containing 20% piperidine and the reaction mixture was shaken at room temperature for 3 hours. After the completion of reaction, the reaction mixture was filtered and was washed repeatedly with DMF, MC, MC/MeOH (1/1, υ/υ) and MeOH to obtain a light-brown solid resin (formula 5-1) (ATR-FTIR; carbamate peak disappeared: 1700 $cm^{-1}$).

A benzopyran resin (0.200 g, 0.20 mmol) represented by the formula 4-2 was added to 3 mL of DMF and then the reaction mixture was shaken at room temperature for 10 minutes. BnBr (0.071 mL, 0.60 mmol) and diisopropylamine (0.084 mL, 0.60 mmol) were added thereto and then the reaction mixture was shaken at room temperature for 15 hours for mixing. After the completion of reaction, the reaction mixture was filtered and washed repeatedly with DMF, MC, MC/MeOH and MeOH to obtain a light-brown solid resin (formula 5-2).

The obtained resin (formula 5-2) was added to 5 mL of DMF containing 20% piperidine and the reaction mixture was shaken at room temperature for 3 hours. After the completion of reaction, the reaction mixture was filtered and washed repeatedly with DMF, MC, MC/MeOH (1/1, υ/υ) and MeOH to obtain a light-brown solid resin (formula 5-2) (ATR-FTIR; carbamate peak disappeared: 1700 $cm^{-1}$).

EXAMPLE III

N-sulfonation using 6-alkylamino-2-methyl-2'-(methylamino)methyl-2H-1-benzopyran resin (formula 4)

III-1: N-sulfonation and confirmation of 6-alkylamino-2-methyl-2'-(methylamino)methyl-2H-1-benzopyran resin

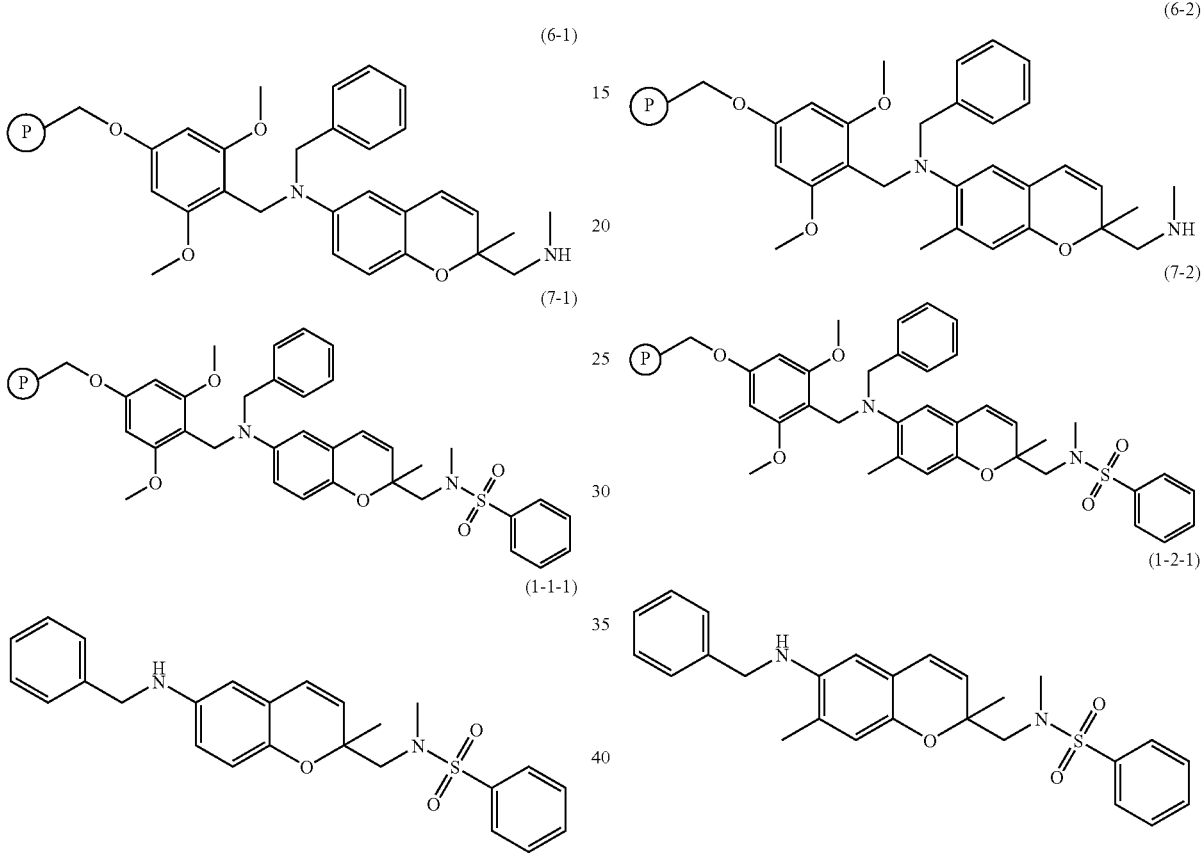

A benzopyran resin (0.200 g, 0.22 mmol) represented by the formula 6-1 was added to 3 mL of DMF and then the reaction mixture was shaken at room temperature for 10 minutes. Benzenesulfonyl chloride (PhSO₂Cl; 0.084 mL, 0.66 mmol) and triethylamine (0.092 mL, 0.66 mmol) were added thereto and then the reaction mixture was shaken at room temperature for 15 hours for mixing. After the completion of reaction, the reaction mixture was filtered and washed repeatedly with DMF, MC, MC/MeOH (1/1, v/v) and MeOH to obtain a light-brown solid resin (formula 7-1).

The obtained resin (formula 7-1, 0.200 g, 0.66 mmol) was added to 5 mL of DCM and then 1 mL of TFA was added thereto. The reaction mixture was shaken at room temperature for 4 hours. After the completion of reaction, the reaction mixture was filtered and was washed repeatedly with DCM and MeOH. The washed solution and the filtrate were combined and then concentrated. After 3 mL of ethylacetate was added to the concentrated mixture, the reaction mixture was filtered with a strong anion exchange resin (SAX resin) and washed repeatedly with ethylacetate to remove residual TFA. After concentration under reduced pressure, the concentrate was isolated and purified by silica gel column chromatography using a solvent mixture of hexane/ethylacetate (4/1, υ/υ) to obtain an oil represented by the formula 1-1 (78 mg, 82%; loading capacity of resin 4-1=1.1 mmol/g).

III-2: N-sulfonation and confirmation of 6-alkylamino-2-methyl-2'-(methylamino)methyl-2H-1-benzopyran resin A benzopyran resin (0.200 g, 0.22 mmol) represented by the formula 6-1 was added to 3 mL of DMF and then the reaction mixture was shaken at room temperature for 10 minutes. PhSO₂Cl (0.077 mL, 0.60 mmol) and triethylamine (0.083 mL, 0.60 mmol) were added thereto and then the reaction mixture was shaken at room temperature for 15 hours for mixing. After the completion of reaction, the reaction mixture was filtered and washed repeatedly with DMF, MC, MC/MeOH and MeOH to obtain a light-brown solid resin (formula 7-2).

The obtained resin (formula 7-2, 0.200 g, ___ mmol) was added to 5 mL of DCM and then 1 mL of TFA was added thereto. The reaction mixture was shaken at room temperature for 4 hours. After the completion of reaction, the reaction mixture was filtered and washed repeatedly with DCM and MeOH. The washed solution and the filtrate were combined and then concentrated. 3 mL of ethylacetate was added to the concentrated mixture and the reaction mixture was filtered with a strong anion exchange resin (SAX resin) and washed repeatedly with ethylacetate to remove residual TFA. After concentration under reduced pressure, the concentrate was isolated and purified by silica gel column chromatography using a solvent mixture of hexane/ethylacetate (4/1, υ/υ) to obtain an oil represented by the formula 1-2-1 (68 mg, 76%; loading capacity of resin 4-2=1.0 mmol/g).

Isomeric compounds of the 6-alkylamino-2-methyl-2'-(N-methyl substituted sulfonamido)methyl-2H-1-benzopyran derivatives were synthesized by a solid-phase parallel synthetic method in the same manner as in Examples. They are also shown in Table 1.

Table 1

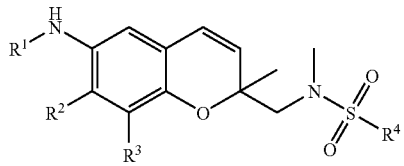

(1)

| Compd. No. | R₁ | R₂ | R₃ | R₄ | Analysis result (NMR/MS) |
|---|---|---|---|---|---|
| 1-1-1 | 4-MeOBn | H | H | Ph | $^1$H NMR(200 MHz, CDCl$_3$) δ 7.78-7.72(m, 2H), 7.61-7.44(m, 3H), 7.32-7.23(m, 2H), 6.92-6.81(m, 2H), 6.57(d, 1H, J=8.5 Hz), 6.44-6.30(m, 3H), 5.63(d, 1H, J=9.8 Hz), 4.17(s, 2H), 3.80(s, 3H), 3.22(d, 1H, J=14.2 Hz), 3.14(d, 1H, J=14.2 Hz), 2.87(s, 3H), 1.51(s, 3H) |
| 1-1-2 | 3-MeOBn | H | H | Ph | $^1$H NMR(200 MHz, CDCl$_3$) δ 7.78-7.73(m, 2H), 7.61-7.44(m, 3H), 7.29-7.21(m, 1H), 6.93(d, 2H, J=7.1 Hz), 6.91-6.77(m, 1H), 6.57(d, 1H, J=8.5 Hz), 6.44-6.30(m, 3H), 5.64(d, 1H, J=9.8 Hz), 4.22(s, 2H), 3.80(s, 3H), 3.23(d, 1H, J=14.2 Hz), 3.15(d, 1H, J=14.2 Hz), 2.87(s, 3H), 1.51(s, 3H) |
| 1-1-3 | 2-MeOBn | H | H | Ph | $^1$H NMR(200 MHz, CDCl$_3$) δ 7.78-7.73(m, 2H), 7.60-7.44(m, 3H), 7.30-7.20(m, 2H), 6.93-6.86(m, 2H), 6.56(d, 1H, J=8.5 Hz), 6.43(dd, 1H, J=8.5 Hz, J=2.8 Hz), 6.39-6.32(m, 2H), 5.63(d, 1H, J=9.7 Hz). 4.25(s, 2H), 3.85(s, 3H), 3.23(d, 1H, J=14.4 Hz), 3.14(d, 1H, J=14.4 Hz), 2.87(s, 3H), 1.51(s, 3H) |
| 1-1-4 | Bn | H | H | Ph | $^1$H NMR(200 MHz, CDCl$_3$) δ 7.78-7.73(m, 2H), 7.61-7.44(m, 3H), 7.38-7.23(m, 5H), 6.57(d, 1H, J=8.5 Hz), 6.44-6.30(m, 3H), 5.64(d, 1H, J=9.8 Hz), 4.25(s, 2H), 3.23(d, 1H, J=14.4 Hz), 3.14(d, 1H, J=14.4 Hz), 2.87(s, 3H), 1.51(s, 3H) |
| 1-1-5 | 4-tert-BuBn | H | H | Ph | $^1$H NMR(200 MHz, CDCl$_3$) δ 7.78-7.73(m, 2H), 7.51-7.44(m, 3H), 7.39-7.26(m, 4H), 6.58(d, 1H, J=8.3 hz), 6.45-6.31(m, 2H), 5.65(d, 1H, J=9.9 Hz), 4.21(s, 2H), 3.24(d, 1H, J=14.4 Hz), 3.15(d, 1H, J=14.4 Hz), 2.88(s, 3H), 1.52(s, 3H) |
| 1-1-6 | 3-ClBn | H | H | Ph | $^1$H NMR(200 MHz, CDCl$_3$) δ 7.78-7.73(m, 2H), 7.61-7.44(m, 3H), 7.34(s, 1H), 7.26-7.23(m, 3H), 6.57(d, 1H, J=8.5 Hz), 6.41-6.26(m, 3H), 5.64(d, 1H, J=9.8 Hz), 4.24(s, 2H), 3.23(d, 1H, J=14.4 Hz), 3.15(d, 1H, J=14.4 Hz), 2.87(s, 3H), 1.51(s, 3H) |
| 1-1-7 | 4-CNBn | H | H | Ph | $^1$H NMR(200 MHz, CDCl$_3$) δ 7.77-7.72(m, 2H), 7.63-7.26(m, 7H), 6.55(d, 1H, J=8.5 Hz), 6.37-6.22(m, 3H), 5.65(d, 1H, J=9.8 Hz), 4.34(s, 2H), 3.90(br, 1H), 3.18(s, 2H), 2.85(s, 3H), 1.49(s, 3H) |
| 1-1-8 | 4-EtOBn | H | H | Ph | $^1$H NMR(200 MHz, CDCl$_3$) δ 7.78-7.73(m, 2H), 7.61-7.44(m, 3H), 7.30-7.23(m, 2H), 6.85(d, 2H, J=8.5 Hz), 6.57(d, 1H, J=8.3 Hz), 6.44-6.30(m, 2H), 5.64(d, 1H, J=9.8 Hz), 4.16(s, 2H), 4.09-3.97(m, 4H), 3.23(d, 1H, J=14.2 Hz), 3.14(d, 1H, J=14.2 Hz), 2.87(s, 3H), 1.52(s, 3H), 1.41(t, 3H, J=7.1 Hz) |
| 1-1-9 | 2-FBn | H | H | Ph | $^1$H NMR(200 MHz, CDCl$_3$) δ 7.78-7.72(m, 2H), 7.61-7.44(m, 3H), 7.39-7.28(m, 1H), 7.26-7.19(m, 1H), 7.19-6.99(m, 2H), 6.59(d, 1H, J=8.5 Hz), 6.45-6.30(m, 3H), 5.63(d, 1H, J=9.8 Hz), 4.31(s, 2H), 3.23(d, 1H, J=14.4 Hz), 3.14(d, 1H, J=14.4 Hz), 2.86(s, 3H), 1.51(s, 3H) |
| 1-1-10 | 4-FBn | H | H | Ph | $^1$H NMR(200 MHz, CDCl$_3$) δ 7.78-7.73(m, 2H), 7.61-7.44(m, 3H), 7.37-7.25(m, 2H), |

-continued

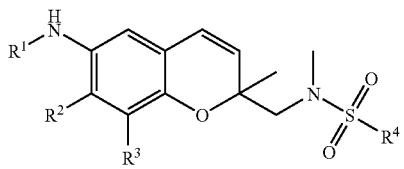

(1)

| Compd. No. | R₁ | R₂ | R₃ | R₄ | Analysis result (NMR/MS) |
|---|---|---|---|---|---|
| | | | | | 7.09-6.96(m, 2H), 6.57(d, 1H, J=8.5 Hz), 6.42-6.28(m, 3H), 5.65(d, 1H, J=9.8 Hz), 4.21(s, 2H), 3.23(d, 1H, J=14.4 Hz), 3.15(d, 1H, J=14.4 Hz), 2.86(s, 3H), 1.51(s, 3H) |
| 1-1-11 | 3-FBn | H | H | Ph | ¹H NMR(200 MHz, CDCl₃) δ 7.78-7.73(m, 2H), 7.61-7.44(m, 3H), 7.34-7.23(m, 1H), 7.14-7.03(m, 2H), 6.99-6.89(m, 1H), 6.57(d, 1H, J=8.5 Hz), 6.42-6.27(m, 3H), 5.64(d, 1H, J=9.8 Hz), 4.26(s, 2H), 3.23(d, 1H, J=14.3 Hz), 3.14(d, 1H, J=14.3 Hz), 2.87(s, 3H), 1.51(s, 3H) |
| 1-1-12 | i-Bu | H | H | Ph | ¹H NMR(200 MHz, CDCl₃) δ 7.79-7.72(m, 2H), 7.60-7.44(m, 3H), 6.57(d, 1H, J=8.5 Hz), 6.41-6.35(m, 2H), 6.27(d, 1H, J=2.5 Hz), 5.63(d, 1H, J=9.8 Hz), 3.23(d, 1H, J=14.2 Hz), 3.13(d, 1H, J=14.2 Hz), 2.87-2.82(m, 5H), 1.51(s, 2H), 0.96(d, 6H, J=6.7 Hz) |
| 1-1-13 | 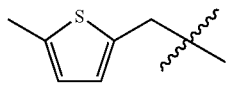 | H | H | Ph | ¹H NMR(200 MHz, CDCl₃) δ 7.79-7.72(m, 2H), 7.60-7.43(m, 3H), 6.78-6.73(m, 1H), 6.60-6.55(m, 2H), 6.34-6.32(m, 2H), 5.64(d, 1H, J=9.8 Hz), 4.33(s, 2H), 3.23(d, 1H, J=14.3 Hz), 3.14(d, 1H, J=14.3 Hz), 2.86(s, 3H), 2.43(s, 3H), 1.51(s, 3H) |
| 1-1-14 | 2-NO₂Bn | H | H | Ph | ¹H NMR(200 MHz, CDCl₃) δ 8.11-8.00(m, 1H), 7.77-7.70(m, 2H), 7.66-7.35(m, 6H), 6.53(d, 1H, J=8.5 Hz), 6.36-6.30(m, 2H), 6.22(d, 1H, J=2.8 Hz), 5.63(d, 1H, J=9.8 Hz), 4.97(s, 2H), 4.61(s, 3H), 3.17(s, 2H), 2.85(s, 3H), 1.48(s, 3H) |
| 1-1-15 | 4-NO₂Bn | H | H | Ph | ¹H NMR(200 MHz, CDCl₃) δ 8.16(d, 2H, J=8.8 Hz), 7.77-7.72(m, 2H), 7.61-7.43(m, 5H), 6.55(d, 1H, J=8.5 Hz), 6.37-6.29(m, 2H), 5.64(d, 1H, J=10.0 Hz), 4.38(s, 2H), 3.99(br, 1H), 3.18(s, 2H), 2.85(s, 3H), 1.48(s, 3H) |
| 1-1-16 | 3-NO₂Bn | H | H | Ph | ¹H NMR(200 MHz, CDCl₃) δ 8.21(s, 1H), 8.12-8.07(m, 2H), 7.76-7.66(m, 3H), 7.56-7.44(m, 4H), 6.55(d, 1H, J=8.5 Hz), 6.39-6.30(m, 2H), 6.25(d, 1H, J=2.6 Hz), 5.64(d, 1H, J=9.8 Hz), 4.37(s, 2H), 3.18(s, 2H), 2.85(s, 3H), 1.50(s, 3H) |
| 1-1-17 | PhEt | H | H | Ph | ¹H NMR(200 MHz, CDCl₃) δ 7.78-7.72(m, 2H), 7.56-7.43(m, 3H), 7.35-7.18(m, 5H), 6.57(d, 1H, J=8.3 Hz), 6.41-6.34(m, 2H), 6.28(d, 1H, J=2.6 Hz), 5.63(d, 1H, J=9.8 Hz), 3.82(t, 3H, J=7.4 Hz), 3.23(d, 1H, J=12.4 Hz), 3.13(d, 1H, J=12.4 Hz), 2.91-2.16(m, 5H), 1.51(s, 3H) |
| 1-1-18 | n-Pr | H | H | Ph | ¹H NMR(200 MHz, CDCl₃) δ 7.77-7.72(m, 2H), 7.56-7.43(m, 3H), 6.56(d, 1H, J=8.2 Hz), 6.41-6.34(m, 2H), 6.27(d, 1H, J=2.8 Hz), 5.63(d, 1H, J=10.0 Hz), 3.22(d, 1H, J=14.3 Hz), 3.14(d, 1H, J=14.3 Hz), 2.99(t, 2H, J=7.1 Hz), 2.86(s, 3H), 1.65-1.54(m, 2H), 1.51(s, 3H), 0.97(t, 3H, J=7.3 Hz) |
| 1-1-19 | 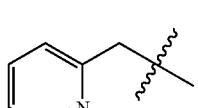 | H | H | Ph | ¹H NMR(200 MHz, CDCl₃) δ 8.57-8.54(m, 1H), 7.77-7.71(m, 2H), 7.67-7.54(m, 1H), 7.53-7.42(m, 3H), 7.30(d, 1H, J=7.9 Hz), 7.19-7.13(m, 1H), 6.56(d, 1H, J=8.5 Hz), 6.47-6.31(m, 3H), 5.62(d, 1H, J=10.0 Hz), 4.36(s, 2H), 3.22(d, 1H, J=14.3 Hz), 3.14(d, 1H, J=14.3 Hz), 2.86(s, 3H), 1.50(s, 3H) |

-continued

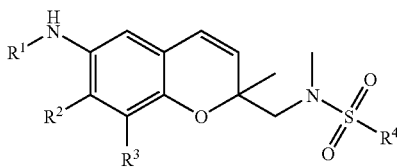

(1)

| Compd. No. | R₁ | R₂ | R₃ | R₄ | Analysis result (NMR/MS) |
|---|---|---|---|---|---|
| 1-1-20 | (3-pyridylmethyl) | H | H | Ph | ¹H NMR(200 MHz, CDCl₃) δ 8.59(m, 1H), 8.50(d, 1H, J=4.1 Hz), 7.77-7.64(m, 3H), 7.60-7.42(m, 3H), 7.28-7.20(m, 1H), 6.56(d, 1H, J=8.5 Hz), 6.42-6.31(m, 1H), 6.28(d, 1H, J=2.6 Hz), 5.63(d, 1H, J=9.8 Hz), 4.27(s, 2H), 3.21(d, 1H, J=15.2 Hz), 3.14(d, 1H, J=15.2 Hz), 2.85(s, 3H), 1.49(s, 3H) |
| 1-1-21 | (4-pyridylmethyl) | H | H | Ph | ¹H NMR(200 MHz, CDCl₃) δ 8.55-8.51(m, 2H), 7.77-7.72(m, 2H), 7.56-7.43(m, 3H), 7.28-7.25(m, 2H), 6.55(d, 1H, J=8.5 Hz), 6.37-6.29(m, 2H), 6.23(d, 1H, J=2.6 Hz), 5.64(d, 1H, J=10.0 Hz), 4.29(s, 2H), 3.18(s, 2H), 2.85(s, 3H), 1.49(s, 3H) |
| 1-1-22 | (4-(diethoxymethyl)benzyl) | H | H | Ph | m/z 537 [M + H]⁺ |
| 1-1-23 | (2-thienylmethyl) | H | H | Ph | ¹H NMR(200 MHz, CDCl₃) δ 7.77-7.72(m, 2H), 7.59-7.41(m, 4H), 7.32(d, 2H, J=8.3 Hz), 6.55(d, 1H, J=8.5 Hz), 6.42-6.28(m, 3H), 5.63(d, 1H, J=9.8 Hz), 4.23(s, 2H), 3.70-3.44(m, 4H), 3.23(d, 1H, J=14.2 Hz), 3.14(d, 1H, J=14.2 Hz), 2.86(s, 3H), 1.50(s, 3H), 1.23(t, 3H, J=7.0 Hz) |
| 1-1-24 | (3-thienylmethyl) | H | H | Ph | m/z 441 [M + H]⁺ |
| 1-1-25 | (4-acetoxybenzyl) | H | H | Ph | m/z 493 [M + H]⁺ |
| 1-1-26 | 4-ClBn | H | H | Ph | m/z 470 [M + H]⁺ |
| 1-1-27 | 4-HOBn | H | H | Ph | m/z 451 [M + H]⁺ |
| 1-1-28 | 4-MeOBn | H | H | 4-MeOPh | ¹H NMR(500 MHz, CDCl₃) δ 7.68(d, 2H, J=8.7 Hz), 7.16-7.11(m, 4H), 6.96(d, 2H, J=8.7 Hz), 6.86-6.82(m, 4H), 6.56-6.50(m, 2H), 6.40(d, 1H, J=2.8 Hz), 6.31(d, 1H, J=10.0 Hz), 5.60(d, 1H, J=10 Hz), 4.41(s, 3H), 3.86(s, 6H), 3.16(s, 2H), 2.84(s, 3H), 1.57(s, 3H) |
| 1-1-29 | 3-MeOBn | H | H | 4-MeOPh | ¹H NMR(500 MHz, CDCl₃) δ 7.69-7.67(m, 2H), 7.26-7.22(m, 1H), 6.96-6.94(m, 4H), 6.91-6.90(m, 1H), 6.56(d, 1H, J=8.5 Hz), 6.41(m, 1H), 6.35(d, 1H, J=9.8 Hz), 6.30(d, 1H, J=2.8 Hz), 5.60(d, 1H, J=9.8 Hz), 4.22(s, 2H), 3.85(s, 3H), 3.79(s, 3H), 3.18(d, 1H, J=14.2 Hz), 3.11(d, 1H, J=14.2 Hz), 2.84(s, 3H), 1.50(s, 3H) |
| 1-1-30 | 2-MeOBn | H | H | 4-MeOPh | ¹H NMR(500 MHz, CDCl₃) δ 7.68(d, 2H, J=7.0 Hz), 7.27-7.25(m, 2H), 6.95(d, 2H, J=7.0 Hz), 6.90-6.86(m, 2H), 6.55(d, 1H, J=8.6 Hz), 6.43(m, 1H), 6.35(d, 1H, J=9.8 Hz), 6.32(d, 1H, J=2.7 Hz), 5.62(d, 1H, J=9.8 Hz), 4.24(s, 2H), |

-continued

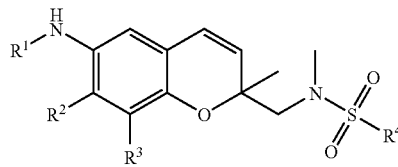

(1)

| Compd. No. | R₁ | R₂ | R₃ | R₄ | Analysis result (NMR/MS) |
|---|---|---|---|---|---|
| | | | | | 3.85(s, 6H), 3.18(d, 1H, J=14.3 Hz), .11(d, 1H, J=14.3 Hz), 2.83(s, 3H), 1.50(s, 3H) |
| 1-1-31 | Bn | H | H | 4-MeOPh | $^1$H NMR(500 MHz, CDCl$_3$) δ 6.68(d, 2H, J=6.9 Hz), 7.35-7.32(m, 4H), 7.25(m, 1H), 6.95(d, 2H, J=6.9 Hz), 6.57(d, 1H, J=8.5 Hz), 6.41(dd, 1H, J=8.6, 2.8 Hz), 6.35(d, 1H, J=2.8 Hz), 5.63(d, 1H, J=9.8 Hz), 4.24(s, 2H), 3.85(s, 3H), 3.18(d, 1H, J=14.3 Hz), 3.12(d, 1H, J=14.3 Hz), 2.83(s, 3H), 1.50(s, 3H) |
| 1-1-32 | 4-tert-BuBn | H | H | 4-MeOPh | $^1$H NMR(500 MHz, CDCl$_3$) δ 7.67(d, 2H, J=7.0 Hz), 7.37-7.35(m, 2H), 7.29-7.25(m, 2H), 6.95(d, 2H, J=7.0 Hz), 6.57(d, 1H, J=8.5 Hz), 6.42(m, 1H), 6.36(d, 1H, J=9.8 Hz), 6.32(d, 1H, J=2.8 Hz), 5.64(d, 1H, J=9.8 Hz), 4.20(s, 2H), 3.85(s, 3H), 3.19(d, 1H, J=14.3 Hz), 3.12(d, 1H, J=14.3 Hz), 2.84(s, 3H), 1.50(s, 3H), 1.31(s, 9H) |
| 1-1-33 | 3-ClBn | H | H | 4-MeOPh | $^1$H NMR(500 MHz, CDCl$_3$) δ 7.68(d, 2H, J=6.9 Hz), 7.26-7.23(m, 4H), 6.95(d, 2H, J=6.9 Hz), 6.57(d, 1H, J=8.5 Hz), 6.39-6.33(m, 2H), 6.27(d, 1H, J=2.8 Hz), 5.64(d, 1H, J=9.8 Hz), 4.24(s, 2H), 3.86(s, 3H), 3.18(d, 1H, J=14.3 Hz), 3.13(d, 1H, J=14.3 Hz), 2.84(s, 3H), 1.50(s, 3H) |
| 1-1-34 | 4-CNBn | H | H | 4-MeOPh | $^1$H NMR(500 MHz, CDCl$_3$) δ 7.67(d, 2H, J=7.0 Hz), 7.60(d, 2H, J=8.0 Hz), 7.46(d, 2H, J=8.0 Hz), 6.95(d, 2H, J=7.0 Hz), 6.55(d, 1H, J=8.6 Hz), 6.35-6.31(m, 2H), 6.23(d, 1H, J=2.8 Hz), 5.65(d, 1H, J=9.8 Hz), 4.34(s, 2H), 3.86(s, 3H), 3.18(d, 1H, J=14.3 Hz), 3.12(d, 1H, J=14.3 Hz), 2.83(s, 3H), 1.48(s, 3H) |
| 1-1-35 | 4-EtOBn | H | H | 4-MeOPh | $^1$H NMR(500 MHz, CDCl$_3$) δ 7.68(d, 2H, J=6.9 Hz), 7.25(d, 2H, J=6.7 Hz), 6.95(d, 2H, J=6.9 Hz), 6.85(d, 2H, J=6.7 Hz), 6.57(d, 1H, J=8.5 Hz), 6.41(m, 1H), 6.35(d, 1H, J=9.8 Hz) 6.30(d, 1, J=2.7 Hz), 5.63(d, 1H, J=9.8 Hz), 4.15(s, 2H), 4.02(q, 2H, J=7.0 Hz), 3.84(s, 3H), 3.18(d, 1H, J=14.3 Hz), 3.11(d, 1H, J=14.3 Hz), 2.84(s, 3H), 1.50(s, 3H), 1.40(t, 3H, J=7.0 Hz) |
| 1-1-36 | 2-FBn | H | H | 4-MeOPh | $^1$H NMR(500 MHz, CDCl$_3$) δ 7.68(d, 2H, J=7.0 Hz), 7.40-7.30(m, 1H), 7.26-7.15(m, 1H), 7.10-7.00(m, 1H), 6.95(d, 2H, J=7.0 Hz), 6.57(d, 1H, J=8.6 Hz), 6.42(dd, 1H, J=8.6, 2.8 Hz), 6.35(d, 1, J=9.8 Hz), 6.31(d, 1H, J=9.8 Hz), 4.31(s, 2H), 3.84(s, 3H), 3.17(d, 1H, J=14.3 Hz), 3.12(d, 1H, J=14.3 Hz), 2.83(s, 3H), 1.50(s, 3H) |
| 1-1-37 | 4-FBn | H | H | 4-MeOPh | $^1$H NMR(500 MHz, CDCl$_3$) δ 7.68(d, 2H, J=7.0 Hz), 7.31-7.29(m, 2H), 7.03-6.98(m, 2H), 6.95(d, 2H, J=7.0 Hz), 6.57(d, 1H, J=8.6 Hz), 6.40(m, 1H), 6.34(d, 1H, J=9.9 Hz), 6.28(d, 1H, J=2.8 Hz), 5.64(d, 1H, J=9.9 Hz), 4.21(s, 2H), 3.85(s, 3H), 3.18(d, 1H, J=14.3 Hz), 3.12(d, 1H, J=14.3 Hz), 2.83(s, 3H), 1.50(s, 3H) |
| 1-1-38 | 3-FBn | H | H | 4-MeOPh | $^1$H NMR(500 MHz, CDCl$_3$) δ 7.68(d, 2H, J=6.9 Hz), 7.26(m, 1H), 7.12-7.10(m, 2H), 6.95(m, 3H), 6.56(d, 1H, J=8.6 Hz), 6.38(dd, 1H, J=8.6, 2.8 Hz), 6.34(d, 1H, J=9.8 Hz), 6.27(d, 1H, J=2.8 Hz), 4.25(s, 2H), 3.85(s, 3H), 3.18(d, 1H, J=14.3 Hz), 3.12(d, 1H, J=14.3 Hz), 2.84(s, 3H), 1.50(s, 3H) |
| 1-1-39 | i-Bu | H | H | 4-MeOPh | $^1$H NMR(500 MHz, CDCl$_3$) δ 7.28(d, 2H, J=6.9 Hz), 6.95(d, 2H, J=6.9 Hz), 6.56(d, 1H, J=8.6 Hz), 6.38(m, 1H), 6.27(d, 1H, J=2.8 Hz), |

-continued

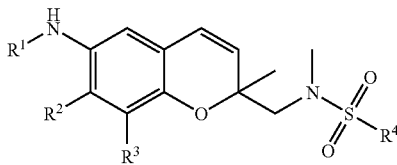

(1)

| Compd. No. | R₁ | R₂ | R₃ | R₄ | Analysis result (NMR/MS) |
|---|---|---|---|---|---|
| | | | | | 5.63(d, 1H, J=9.8 Hz), 3.85(s, 3H), 3.19(d, 1H, J=14.3 Hz), 3.11(d, 1H, J=14.3 Hz), 2.86-2.83(m, 5H), 1.86-1.82(m, 1H), 1.51(s, 3H), 0/96(d, 6H, J=6.7 Hz) |
| 1-1-40 | ![thiophene-CH2] | H | H | 4-MeOPh | ¹H NMR(500 MHz, CDCl₃) δ 7.68(d, 2H, J=6.9 Hz), 6.95(d, 2H, J=6.9 Hz), 6.75(d, 1H, J=3.4 Hz), 6.59-6.56(m, 2H), 6.44(m, 1H), 6.36(d, 1H, J=9.8 Hz), 6.33(d, 1H, J=2.8 Hz), 5.64(d, 1H, J=9.8 Hz), 4.33(s, 3H), 3.18(d, 1H, J=14.3 Hz), 3.12(d, 1H, J=14.3 Hz), 2.43(s, 3H), 1.50(s, 3H) |
| 1-1-41 | 2-NO₂Bn | H | H | 4-MeOPh | ¹H NMR(500 MHz, CDCl₃) δ 8.03(s, 1H), 7.69-7.63(m, 3H), 7.56(m, 1H), 7.40(m, 1H), 6.95(d, 2H, J=6.9 Hz), 6.54(d, 1H, J=8.6 Hz), 6.35-6.30(m, 2H), 6.22(d, 1H, J=2.7 Hz), 5.63(d, 1H, J=9.8 Hz), 4.63(s, 2H), 3.85(s, 3H), 3.17(d, 1H, J=14.3 Hz), 3.12(d, 1H, J=14.3 Hz), 1.49(s, 3H) |
| 1-1-42 | 4-NO₂Bn | H | H | 4-MeOPh | ¹H NMR(500 MHz, CDCl₃) δ 7.18(d, 2H, J=8.6 Hz), 7.68(d, 2H, J=6.9 Hz), 7.52(d, 2H, J=8.6 Hz), 6.95(d, 2H, J=6.9 Hz), 6.56(d, 1H, J=8.6 Hz), 6.36-6.31(m, 1H), 6.24(d, 1H, J=2.7 Hz), 5.65(d, 1H, J=9.9 Hz), 4.39(s, 2H), 3.86(s, 3H), 3.17(d, 1H, J=14.3 Hz), 3.12(d, 1H, J=14.3 Hz), 2.82(s, 3H), 1.49(s, 3H) |
| 1-1-43 | 3-NO₂Bn | H | H | 4-MeOPh | ¹H NMR(500 MHz, CDCl₃) δ 8.22(s, 1H), 8.10(m, 1H), 7.70-7.6(m, 3H), 7.52-7.47(m, 1H), 6.95(d, 2H, J=8.9 Hz), 6.56(d, 1H, J=8.5 Hz), 6.38-6.31(m, 2H), 6.25(d, 1H, J=2.7 Hz), 5.64(d, 1H, J=9.8 Hz), 4.38(s, 2H), 3.17(d, 1H, J=14.3 Hz), 3.13(d, 1H, J=14.3 Hz), 2.83(s, 3H), 1.49(s, 3H) |
| 1-1-44 | PhEt | H | H | 4-MeOPh | ¹H NMR(500 MHz, CDCl₃) δ 7.68(d, 2H, J=6.9 Hz), 7.31-7.29(m, 2H), 7.26-7.19(m, 3H), 6.95(d, 2H, 6.9 Hz), 6.57(d, 1H, J=8.6 Hz), 6.38-6.35(m, 2H), 6.28(d, 1H, J=2.7 Hz), 5.64(d, 1H, J=9.8 Hz), 3.85(s, 3H), 3.32(t, 2H, J=7.0 Hz), 3.18(d, 1H, J=14.3 Hz), 3.12(d, 1H, J=14.3 Hz), 2.89(t, 2H, J=7.0 Hz), 2.84(s, 3H), 1.51(s, 3H) |
| 1-1-45 | n-Pr | H | H | 4-MeOPh | ¹H NMR(500 MHz, CDCl₃) δ 7.68(d, 2H, J=6.9 Hz), 6.95(d, 2H, J=6.9 Hz), 6.57(d, 1H, J=8.6 Hz), 6.40-6.31(m, 2H), 6.28(d, 1H, J=2.8 Hz), 5.64(d, 1H, J=9.8 Hz), 3.18(d, 1H, J=14.3 Hz), 3.11(d, 1H, J=14.3 Hz), 3.00(t, 2H, J=7.2 Hz), 2.84(s, 3H), 1.63-1.56(m, 2H), 1.51(s, 3H), 0/98(t, 3H, J=7.4 Hz) |
| 1-1-46 | ![pyridine-CH2] | H | H | 4-MeOPh | ¹H NMR(500 MHz, CDCl₃) δ 8.57(d, 1H, J=4.1 Hz), 7.69-7.64(m, 3H), 7.32(d, 1H, J=7.8 Hz), 7.24-7.20(m, 1H), 6.95(d, 2H, J=6.9 Hz), 6.57(d, 1H, J=8.6 Hz), 7.45(m, 1H), 6.37-6.33(m, 2H), 5.63(d, 1H, J=9.8 Hz), 4.38(s, 2H), 3.84(s, 2H), 3.18(d, 1H, J=14.3 Hz), 3.13(d, 1H, J=14.3 Hz), 2.84(s, 3H) |

-continued

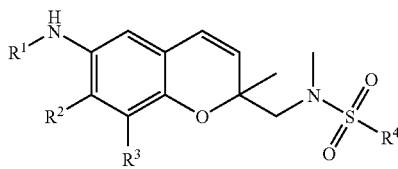

(1)

| Compd. No. | R₁ | R₂ | R₃ | R₄ | Analysis result (NMR/MS) |
|---|---|---|---|---|---|
| 1-1-47 | (3-pyridylmethyl) | H | H | 4-MeOPh | $^1$H NMR(500 MHz, CDCl$_3$) δ 8.51(d, 1H, J=3.8 Hz), 7.68(d, 2H, J=7.0 Hz), 7.26(m, 1H), 6.95(d, 2H, =7.0 Hz), 6.57(d, 1H, J=8.6 Hz), 6.40(dd, 1H, J=8.6, 2.8 Hz), 6.34(d, 1H, J=9.8 Hz), 6.29(d, 1H, =2.8 Hz), 5.65(d, 1H, J=9.8 Hz), 4.28(s, 2H), 3.85(s, 3H), 3.18(d, 1H, J=14.3 Hz), 3.13(d, 1H, J=14.3 Hz), 2.83(s, 3H), 1.50(s, 3H) |
| 1-1-48 | (4-pyridylmethyl) | H | H | 4-MeOPh | $^1$H NMR(500 MHz, CDCl$_3$) δ 8.54(d, 2H, J=5.7 Hz), 7.68(d, 2H, J=8.8 Hz), 7.28(d, 2H, J=5.7 Hz), 5.65(d, 2H, J=8.8 Hz), 5.65(d, 1H, J=8.6 Hz), 6.36-6.31(m, 2H), 6.23(d, 1H, J=2.8 Hz), 5.64(d, 1H, J=9.8 Hz), 4.30(s, 2H), 3.85(s, 3H), 3.17(d, 1H, J=14.3 Hz), 3.13(d, 1H, J=14.3 Hz), 2.83(s, 3H), 1.49(S, 3H) |
| 1-1-49 | (4-(diethoxymethyl)benzyl) | H | H | 4-MeOPh | $^1$H NMR(500 MHz, CDCl$_3$) δ 7.68(d, 2H, J=6.9 Hz), 7.43(d, 2H, J=8.1 Hz), 7.34(d, 2H, J=8.1 Hz), 6.95(d, 2H, J=6.9 Hz), 6.56(d, 1H, J=8.6 Hz), 6.41(m, 1H), 6.34(d, 1H, J=9.8 Hz), 6.29(d, 1H, J=2.8 Hz), 5.63(d, 1H, J=9.8 Hz), 5.48(s, 1H), 4.24(s, 2H), 3.64-3.60(m, 2H), 3.55-3.51(m, 2H), 2.84(s, 3H), 1.50(s, 3H), 1.26-1.21(m, 6H) |
| 1-1-50 | (2-thienylmethyl) | H | H | 4-MeOPh | $^1$H NMR (500 MHz, CDCl$_3$) δ 7.67(d, 2H, J=6.9 Hz), 7.19(m, 1H), 6.98-6.94(m, 4H), 6.58(d, 1H, J=8.5 Hz), 6.45(m, 1H), 6.37-6.33(m, 2H), 5.64(d, 1H, J=9.8 Hz), 4.42(s, 2H), 3.85(s, 3H), 3.18(d, 1H, J=14.3 Hz), 3.12(d, 1H, J=14.3 Hz), 2.83(s, 3H), 1.50(s, 3H) |
| 1-1-51 | (3-thienylmethyl) | H | H | 4-MeOPh | $^1$H NMR(500 MHz, CDCl$_3$) δ 7.68(d, 2H, J=6.9 Hz), 7.27(m, 1H), 7.16(m, 1H), 7.05(m, 1H), 6.95(d, 2H, J=6.9 Hz), 6.58(d, 1H, J=8.6 Hz), 6.44-6.41(m, 1H), 6.36(d, 1H, J=9.8 Hz), 6.32(d, 1H, 2.8 Hz), 5.64(d, 1H, J=9.8 Hz), 4.25(s, 2H), 3.85(s, 3H), 3.18(d, 1H, J=14.3 Hz), 3.12(d, 1H, J=14.3 Hz), 2.84(s, 3H), 1.50(s, 3H) |
| 1-1-52 | (4-acetoxybenzyl) | H | H | 4-MeOPh | $^1$H NMR(500 MHz, CDCl$_3$) δ 7.68(d, 2H, J=6.9 Hz), 7.35(d, 2H, J=8.5 Hz), 6.95(d, 2H, J=6.9 Hz), 6.57(d, 1H, J=8.6 Hz), 6.40(m, 2H), 6.35(d, 1H, J=9.8 Hz), 6.29(d, 1H, J=2.8 Hz), 5.64(d, 1H, J=9.8 Hz), 4.22(s, 2H), 3.85(s, 3H), 3.18(d, 1H, J=14.3 Hz), 3.12(d, 1H, J=14.3 Hz), 2.83(s, 3H), 2.30(s, 3H), 1.50(S, 3H) |
| 1-1-53 | 4-ClBn | H | H | 4-MeOPh | $^1$H NMR(500 MHz, CDCl$_3$) δ 7.68(d, 2H, J=6.9 Hz), 7.28-7.25(m, 4H), 6.95(d, 2H, J=6.9 Hz), 6.56(d, 1H, J=8.6 Hz), 6.39-6.36(m, 2H), 6.34(d, 1H, J=9.9 Hz), 6.27(d, 1H, J=2.8 Hz), 5.64(d, 1H, J=9.9 Hz), 4.22(s, 2H), 3.85(s, 3H), 3.18(d, 1H, J=14.3 Hz), 3.12(d, 1H, J=14.3 Hz), 2.83(s, 3H), 1.50(s, 3H) |
| 1-1-54 | 4-HOBn | H | H | 4-MeOPh | $^1$H NMR(500 MHz, CDCl$_3$) δ 7.68(d, 2H, J=6.9 Hz), 7.19(d, 1H, J=8.1 Hz), 6.95(d, 2H, J=6.9 Hz), 6.78(d, 2H, J=8.5 Hz), 6.57(d, 1H, J=8.5 Hz), 6.41(m, 1H), 6.35(d, 1H, J=9.8 Hz), 6.30(d, 1H, J=2.8 Hz), 5.63(d, 1H, |

-continued

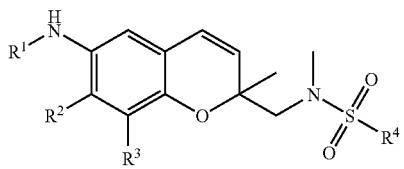

(1)

| Compd. No. | R₁ | R₂ | R₃ | R₄ | Analysis result (NMR/MS) |
|---|---|---|---|---|---|
| | | | | | J=9.8 Hz), 4.14(s, 2H), 3.85(s, 3H), 3.18(d, 1H, J=14.3 Hz), 3.12(d, 1H, J=14.3 Hz), 2.93(s, 3H), 1.50(s, 3H) |
| 1-1-55 | 4-MeOBn | H | H | 2-thienyl | $^1$H NMR(500 MHz, CDCl$_3$) δ 7.55(d, 1H, J=5.0 Hz), 7.51(m, 1H), 7.26(d, 2H, J=8.7 Hz), 7.09(m, 1H), 6.86(d, 2H, J=8.7 Hz), 6.57(d, 1H), 6.37(d, 1H, J=9.8 Hz), 6.31(d, 1H, J=2.8 Hz), 5.63(d, 1H, J=9.8 Hz), 4.16(s, 2H), 3.80(s, 3H), 3.19(d, 1H, J=14.3 Hz), 3.13(d, 1H, J=14.3 Hz), 2.92(s, 3H), 1.51(s, 3H) |
| 1-1-56 | 3-MeOBn | H | H | 2-thienyl | $^1$H NMR(500 MHz, CDCl$_3$) δ 7.55(d, 1H, J=5.0 Hz), 7.51(m, 1H), 7.24(m, 1H), 7.09(m, 1H), 6.91(m, 2H), 6.70(m, 1H), 6.58(d, 1H, J=8.6 Hz), 6.42(m, 1H), 6.36(d, 1H, J=9.9 Hz), 6.30(d, 1H, J=2.8 Hz), 5.62(d, 1H, J=9.9 Hz), 4.22(s, 2H), 3.79(s, 3H), 3.19(d, 1H, J=14.3 Hz), 3.13(d, 1H, J=14.3 Hz), 2.91(s, 3H), 1.51(s, 3H) |
| 1-1-57 | 2-MeOBn | H | H | 2-thienyl | $^1$H NMR(500 MHz, CDCl$_3$) δ 7.54(d, 1H, J=5.0 Hz), 7.51(m, 1H), 7.25(m, 2H), 7.09(m, 1H), 6.90-6.86(m, 2H), 6.57(d, 1H, J=8.6 Hz), 6.44(m, 1H), 6.36(d, 1H, J=9.8 Hz), 6.33(d, 1H, J=2.8 Hz), 5.61(d, 1H, J=9.8 Hz), 4.24(s, 2H), 3.85(s, 3H), 3.18(d, 1H, J=14.3 Hz), 3.12(d, 1H, J=14.3 Hz), 2.90(s, 3H), 1.50(s, 3H) |
| 1-1-58 | Bn | H | H | 2-thienyl | $^1$H NMR(500 MHz, CDCl$_3$) δ 7.55(d, 1H, J=5.0 Hz), 7.52-7.50(m, 1H), 7.35-7.32(m, 4H), 7.25(m, 1H), 7.10-7.08(m, 1H), 6.58(d, 1H, J=8.6 Hz), 6.44(m, 1H), 6.36(d, 1H, J=9.8 Hz), 6.31(d, 1H, J=2.8 Hz), 5.62(d, 1H, J=9.8 Hz), 4.25(s, 2H), 3.19(d, 1H, J=14.3 Hz), 3.13(d, 1H, J=14.3 Hz), 2.92(s, 3H), 1.51(s, 3H) |
| 1-1-59 | 4-tert-BuBn | H | H | 2-thienyl | $^1$H NMR(500 MHz, CDCl$_3$) δ 7.55(d, 1H, J=5.0 Hz), 7.52-7.50(m, 1H), 7.37-7.35(m, 2H), 7.30-7.24(m, 2H), 7.08(m, 1H), 6.59(d, 1H, J=8.6 Hz), 6.44(m, 1H), 6.37(d, 1H, J=9.8 Hz), 6.32(d, 1H, J=2.7 Hz), 5.63(d, 1H, J=9.8 Hz), 4.20(s, 2H), 3.19(d, 1H, J=14.3 Hz), 3.13(d, 1H, J=14.3 Hz), 2.91(s, 3H), 1.51(s, 3H), 1.31(s, 9H) |
| 1-1-60 | 3-ClBn | H | H | 2-thienyl | $^1$H NMR(500 MHz, CDCl$_3$) δ 7.55(d, 1H, J=5.0 Hz), 7.51(m, 1H), 7.35(m, 1H), 7.26-7.23(m, 4H), 7.11-7.09(m, 1H), 6.58(d, 1H, J=8.6 Hz), 6.40(m, 1H), 6.35(d, 1H, J=9.8 Hz), 6.28(d, 1H, J=2.8 Hz), 5.63(d, 1H, J=9.8 Hz), 4.24(s, 2H), 3.19(d, 1H, J=14.3 Hz), 3.14(d, 1H, J=14.3 Hz), 2.91(s, 2H), 1.50(s, 3H) |
| 1-1-61 | 4-CNBn | H | H | 2-thienyl | $^1$H NMR(500 MHz, CDCl$_3$) δ 7.61(d, 2H, J=8.2 Hz), 7.58-7.56(m, 1H), 7.53-7.51(m, 1H), 7.46(d, 2H, J=8.2 Hz), 7.27-7.09(m, 1H), 6.57(d, 1H, J=8.6 Hz), 6.47-6.32(m, 2H), 6.24(d, 1H, J=2.8 Hz), 5.64(d, 1H, J=9.8 Hz), 4.35(s, 2H), 3.16(s, 2H), 2.90(s, 3H), 1.49(s, 3H) |

-continued

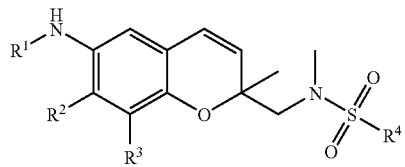

(1)

| Compd. No. | R₁ | R₂ | R₃ | R₄ | Analysis result (NMR/MS) |
|---|---|---|---|---|---|
| 1-1-62 | 4-EtOBn | H | H | (2-thienyl) | ¹H NMR(500 MHz, CDCl₃) δ 7.55(d, 1H, J=5.0 Hz), 7.51(m, 1H), 7.25(d, 2H, J=8.6 Hz), 7.09(m, 1H), 6.85(d, 1H, J=2.8 Hz), 6.59(d, 1H, J=8.5 Hz), 6.44(m, 1H), 6.37(d, 1H, J=9.8 Hz), 6.31(d, 1H, J=2.8 Hz), 4.16(s, 2H), 4.62(q, 2H, J=7.0 Hz), 3.19(d, 1H, J=14.3 Hz), 3.13(d, 1H, J=14.3 Hz), 2.91(s, 3H), 1.51(s, 3H), 1.41(t, 3H, J=7.0 Hz) |
| 1-1-63 | 2-FBn | H | H | (2-thienyl) | ¹H NMR(500 MHz, CDCl₃) δ 7.55(m, 1H), 7.52-7.51(m, 1H), 7.40-7.30(m, 1H), 7.25-7.20(m, 1H), 7.01-7.08(m, 3H), 6.58(d, 1H, J=8.6 Hz), 6.44(m, 1H), 6.36(d, H, J=9.9 Hz), 6.32(d, 1H, J=2.8 Hz), 5.63(d, 1H, J=9.9 Hz), 4.32(s, 2H), 3.19(d, 1H, J=14.3 Hz), 3.13(d, 1H, J=14.3 Hz), 2.91(s, 3H), 1.51(s, 3H) |
| 1-1-64 | 4-FBn | H | H | (2-thienyl) | ¹H NMR(500 MHz, CDCl₃) δ 7.56-7.51(m, 2H), 7.33-7.25(m, 2H), 7.10(m, 1H), 7.02(m, 2H), 6.58(d, 1H, J=2.8 Hz), 5.64(dd, 1H, J=8.6, 2.8 Hz), 4.21(s, 2H), 3.19(d, 1H, J=14.8 Hz), 3.14(d, 1H, J=14.8 Hz), 2.92(s, 3H), 1.51(s, 3H) |
| 1-1-65 | 3-FBn | H | H | (2-thienyl) | ¹H NMR(500 MHz, CDCl₃) δ 7.56-7.51(m, 2H), 7.26(m, 2H), 7.11-7.08(m, 2H), 6.90(m, 1H), 6.58(d, 1H, J=8.6 Hz), 6.41-6.28(m, 2H), 5.63(d, 1H, J=9.8 Hz), 4.26(s, 2H), 3.19(d, 1H, J=14.8 Hz), 3.14(d, 1H, J=14.8 Hz), 2.91(s, 3H), 1.50(s, 3H) |
| 1-1-66 | i-Bu | H | H | (2-thienyl) | ¹H NMR(500 MHz, CDCl₃) δ 7.56-7.51(m, 2H), 7.10(m, 1H), 6.58(d, H, J=8.5 Hz), 6.41-6.37(m, 2H), 6.28(d, 1H, J=2.8 Hz), 5.63(d, 1H, J=9.8 Hz), 4.26(s, 2H), 3.19(d, 1H, J=14.8 Hz), 3.14(d, 1H, J=14.8 Hz), 2.91(s, 3H), 2.85(m, 2H), 1.51(s, 3H), 0.96(m, 6H) |
| 1-1-67 | (5-methyl-2-thienylmethyl) | H | H | (2-thienyl) | ¹H NMR(500 MHz, CDCl₃) δ 7.56-7.51(m, 2H), 7.11-7.09(m, 1H), 6.75(d, 1H, J=3.4 Hz), 6.59(m, 2H), 6.42(m, 1H), 6.39-6.34(m, 2H), 5.63(d, 1H, J=9.8 Hz), 4.33(s, 2H), 3.19(d, 1H, J=14.8 Hz), 3.14(d, 1H, J=14.8 Hz), 2.91(s, 3H), 2.42(s, 3H), 1.51(s, 3H) |
| 1-1-68 | 2-NO₂Bn | H | H | (2-thienyl) | ¹H NMR(500 MHz, CDCl₃) δ 8.03(m, 1H), 7.55(m, 1H), 7.52(m, 2H), 7.10-7.08(m, 1H), 6.56(d, 1H, J=8.6 Hz), 6.36-6.32(m, 2H), 6.33(d, 1H, J=2.8 Hz), 5.63(d, 1H, J=9.8 Hz), 4.64(s, 2H), 3.18(d, 1H, J=14.8 Hz), 3.14(d, 1H, J=14.8 Hz), 2.91(s, 3H), 1.49(s, 3H) |
| 1-1-69 | 4-NO₂Bn | H | H | (2-thienyl) | ¹H NMR(500 MHz, CDCl₃) δ 8.16(m, 2H), 7.56(m, 1H), 7.51(m, 3H), 7.10(m, 1H), 6.57(d, 1H, J=8.6 Hz), 6.34(m, 2H), 6.24(d, 1H, J=2.8 Hz), 5.64(d, 1H, J=9.8 Hz), 4.39(s, 2H), 3.16(m, 2H), 2.91(s, 3H), 1.49(s, 3H) |
| 1-1-70 | 3-NO₂Bn | H | H | (2-thienyl) | ¹H NMR(500 MHz, CDCl₃) δ 8.22(m, 1H), 8.10(m, 1H), 7.68(m, 1H), 7.55(m, 1H), 7.52-7.05(m, 2H), 7.10-7.08(m, 1H), 6.58(d, 1H, J=8.6 Hz), 6.34(m, 2H), 6.26(d, 1H, J=2.8 Hz), 5.63(d, 1H, J=9.8 Hz), 4.38(s, 2H), 3.18(d, 1H, J=14.8 Hz), 3.14(d, 1H, J=14.8 Hz), 2.91(s, 3H), 1.50(s, 3H) |

-continued

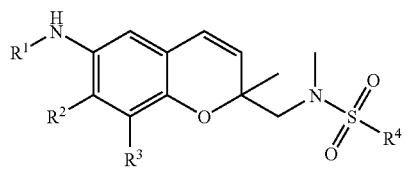

(1)

| Compd. No. | R₁ | R₂ | R₃ | R₄ | Analysis result (NMR/MS) |
|---|---|---|---|---|---|
| 1-1-71 | PhEt | H | H | 2-thienyl | ¹H NMR(500 MHz, CDCl₃) δ 7.56-7.51(m, 2H), 7.32-7.29(m, 2H), 7.26-7.20(m, 4H), 7.10(m, 1H), 6.59(d, 1H, J=8.6 Hz), 6.37(m, 2H), 6.29(d, 1H, J=2.8 Hz), 5.64(d, 1H, J=9.8 Hz), 3.32(t, 2H, J=7.0 Hz), 3.19(d, 1H, J=14.8 Hz), 3.14(d, 1H, J=14.8 Hz), 2.92-2.86(m, 5H), 1.51(s, 3H) |
| 1-1-72 | n-Pr | H | H | 2-thienyl | ¹H NMR(500 MHz, CDCl₃) δ 7.56-7.51(m, 2H), 7.09(m, 1H), 6.59(d, 1H, J=8.5 Hz), 6.41-6.37(m, 2H), 6.29(d, 1H, J=2.8 Hz), 5.63(d, 1H, J=9.8 Hz), 3.19(d, 1H, J=14.8 Hz), 3.14(d, 1H, J=14.8 Hz), 3.00(m, 2H), 2.92(s, 3H), 1.63-1.57(m, 2H), 1.51(s, 3H), 0.98(m, 3H) |
| 1-1-73 | (pyridin-2-yl)methyl | H | H | 2-thienyl | ¹H NMR(500 MHz, CDCl₃) δ 8.57(d, 1H, J=4.5 Hz), 7.64(m, 1H), 7.55-7.50(m, 2H), 7.33(m, 1H), 7.15(m, 1H), 7.08(m, 1H), 6.59(d, 1H, J=2.8 Hz), 5.62(d, 1H, J=9.8 Hz), 4.38(s, 2H), 3.19(d, 1H, J=14.8 Hz), 3.14(d, 1H, J=14.8 Hz), 2.91(s, 3H), 1.50(s, 3H) |
| 1-1-74 | (pyridin-3-yl)methyl | H | H | 2-thienyl | ¹H NMR(500 MHz, CDCl₃) δ 8.61(s, 1H), 8.52(m, 1H), 7.68(m, 1H), 7.56-7.51(m, 2H), 7.26(m, 2H), 7.10-7.08(m, 1H), 6.59(d, 1H, J=8.6 Hz), 6.42(dd, 1H, J=8.6, 2.8 Hz), 6.35(d, 1H, J=9.8 Hz), 5.62(d, 1H, J=9.8 Hz), 4.29(s, 2H), 3.19(d, 1H, J=14.8 Hz), 3.14(d, 1H, J=14.8 Hz), 2.91(s, 3H), 1.50(s, 3H) |
| 1-1-75 | (pyridin-4-yl)methyl | H | H | 2-thienyl | ¹H NMR(500 MHz, CDCl₃) δ 8.53(m, 1H), 7.56-7.51(m, 2H), 7.29-7.25(m, 2H), 7.10-7.08(m, 1H), 6.57(d, 1H, J=8.6 Hz), 6.37-6.32(m, 2H), 6.24(d, 1H, J=2.8 Hz), 5.63(d, 1H, J=9.8 Hz), 4.30(s, 2H), 3.18(d, 1H, J=14.8 Hz), 3.14(d, 1H, J=14.8 Hz), 2.90(s, 3H), 1.49(s, 3H) |
| 1-1-76 | 4-(diethoxymethyl)benzyl | H | H | 2-thienyl | ¹H NMR(500 MHz, CDCl₃) δ 7.56-7.51(m, 2H), 7.43(d, 2H, J=8.6 Hz), 7.34(d, 2H, J=8.6 Hz), 7.10(m, 1H), 6.58(d, 1H, J=8.6 Hz), 6.36(m, 1H), 6.30(d, 1H, J=2.8 Hz), 5.62(d, 1H, J=9.8 Hz), 5.48(s, 1H), 4.24(s, 2H), 3.64-3.60(m, 2H), 3.55-3.51(m, 2H), 3.18-3.14(m, 2H), 2.91(s, 3H), 1.51(s, 3H), 1.23(t, 3H, J=7.0 Hz) |
| 1-1-77 | (thiophen-2-yl)methyl | H | H | 2-thienyl | ¹H NMR(500 MHz, CDCl₃) δ 7.56-7.51(m, 2H), 7.20(d, 1H, J=5.0 Hz), 7.09(m, 1H), 6.99-6.95(m, H), 6.60(d, 1H, J=8.6 Hz), 6.46(m, 1H), 6.38-6.34(m, 2H), 5.63(d, 1H, J=9.8 Hz), 4.43(s, 2H), 3.19(d, 1H, J=14.8 Hz), 3.14(d, 1H, J=14.8 Hz), 2.91(s, 3H), 1.50(s, 3H) |

-continued

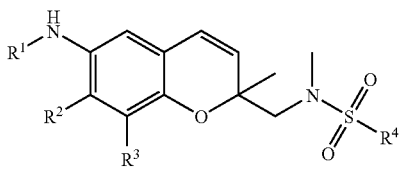

(1)

| Compd. No. | R₁ | R₂ | R₃ | R₄ | Analysis result (NMR/MS) |
|---|---|---|---|---|---|
| 1-1-78 | (3-thienylmethyl-C(CH₃)) | H | H | (2-thienyl) | ¹H NMR(500 MHz, CDCl₃) δ 7.56-7.51(m, 2H), 7.26(m, 1H), 7.17(m, 1H), 7.10-7.06(m, 2H), 6.59(d, 1H, J=8.6 Hz), 6.44(dd, 1H, J=8.6, 2.8 Hz), 6.37(d, 1H, J=9.8 Hz), 6.33(d, 1H, J=2.8 Hz), 5.62(d, 1H, J=9.8 Hz), 4.25(s, 2H), 3.19(d, 1H, J=14.8 Hz), 3.14(d, 1H, J=14.8 Hz), 2.92(s, 3H), 1.51(s, 3H) |
| 1-1-79 | (4-AcO-C₆H₄-CH₂-C(CH₃)) | H | H | (2-thienyl) | ¹H NMR(500 MHz, CDCl₃) δ 7.56-7.51(m, 2H), 7.35(d, 2H, J=8.6 Hz), 7.09(m, 1H), 7.04(d, 2H, J=8.6 Hz), 6.58(d, 1H, J=8.6 Hz), 6.42(m, 1H), 6.36(d, 1H, J=9.8 Hz), 5.63(d, 1H, J=9.8 Hz), 4.24(s, 2H), 3.19(d, 1H, J=14.8 Hz), 3.14(d, 1H, J=14.8 Hz), 2.91(s, 3H), 2.30(s, 3H), 1.51(s, 3H) |
| 1-1-80 | 4-ClBn | H | H | (2-thienyl) | ¹H NMR(500 MHz, CDCl₃) δ 7.57-7.54(m, 2H), 7.29(m, 4H), 7.10(m, 1H), 6.58(m, 1H), 6.39-6.34(m, 2H), 6.28(d, 1H, J=2.8 Hz), 5.63(d, 1H, J=9.8 Hz), 4.23(s, 2H), 3.17(d, 1H, J=14.8 Hz), 3.14(d, 1H, J=14.8 Hz), 2.92(s, 3H), 1.50(s, 3H) |
| 1-1-81 | 4-HOBn | H | H | (2-thienyl) | ¹H NMR(500 MHz, CDCl₃) δ 7.57-7.51(m, 2H), 7.20(d, 2H, J=8.4 Hz), 7.09(m, 2H), 6.78(d, 2H, J=8.5 Hz), 6.58(d, 1H, J=8.5 Hz), 6.38-6.35(m, 2H), 6.31(d, 1H, J=2.8 Hz), 5.65-5.61(m, 1H), 5.62(d, 1H, J=9.8 Hz), 4.29(s, 2H), 3.19(d, 1H, J=14.8 Hz), 3.14(d, 1H, J=14.8 Hz), 2.91(s, 3H), 1.50(s, 3H) |
| 1-1-82 | 4-MeOBn | H | H | 4-MePh | ¹H NMR(500 MHz, CDCl₃) δ 7.62(d, 2H, J=8.3 Hz), 7.29-7.25(m, 4H), 6.88-6.85(m, 2H), 6.56(d, 1H, J=8.6 Hz), 6.40(dd, 1H, J=8.6, 2.8 Hz), 6.35(d, 1H, J=9.8 Hz), 6.30(d, 1H, J=2.8 Hz), 5.63(d, 1H, J=9.8 Hz), 4.16(s, 2H), 3.80(s, 3H), 3.19(d, 1H, J=14.3 Hz), 3.12(d, 1H, J=14.3 Hz), 2.84(s, 3H), 2.41(s, 3H), 1.51(s, 3H) |
| 1-1-83 | 3-MeOBn | H | H | 4-MePh | m/z 479 [M + H]⁺ |
| 1-1-84 | 2-MeOBn | H | H | 4-MePh | ¹H NMR(500 MHz, CDCl₃) δ 7.62(d, 2H, J=8.2 Hz), 7.28-7.21(m, 4H), 6.91-6.86(m, 2H), 6.55(d, 1H, J=8.6 Hz), 6.40(dd, 1H, J=8.6, 2.8 Hz), 6.34(d, 1H, J=9.8 Hz), 6.31(d, 1H, J=2.8 Hz), 5.61(d, 1H, J=9.8 Hz), 4.23(s, 2H), 3.84(s, 3H), 3.18(d, 1H, J=14.8 Hz), 3.12(d, 1H, J=14.8 Hz), 2.84(s, 3H), 2.40(s, 3H), 1.50(s, 3H) |
| 1-1-85 | Bn | H | H | 4-MePh | ¹H NMR(500 MHz, CDCl₃) δ 7.62(d, 2H, J=8.2 Hz), 7.35-7.30(m, 4H), 7.29-7.24(m, 4H), 6.56(d, 1H, J=8.6 Hz), 6.40(dd, 1H, J=8.6, 2.8 Hz), 6.34(d, 1H, J=9.8 Hz), 6.30(d, 1H, J=2.8 Hz), 5.63(d, 1H, J=9.8 Hz), 4.23(s, 2H), 3.19(d, 1H, J=14.8 Hz), 3.12(d, 1H, J=14.8 Hz), 2.84(s, 3H), 2.41(s, 3H), 1.50(s, 3H) |
| 1-1-86 | 4-tert-BuBn | H | H | 4-MePh | m/z 505 [M + H]⁺ |
| 1-1-87 | 3-ClBn | H | H | 4-MePh | ¹H NMR(500 MHz, CDCl₃) δ 7.62(d, 2H, J=8.3 Hz), 7.34(s, 1H), 7.29-7.21(m, 5H), 6.56(d, 1H, J=8.6 Hz), 6.38-6.32(m, 2H), 6.25(d, 1H, J=2.8 Hz), 5.63(d, 1H, J=9.8 Hz), 4.23(s, 2H), 3.18(d, 1H, J=14.3 Hz), 3.13(d, 1H, J=14.3 Hz), 2.84(s, 3H), 2.40(s, 3H), 1.50(s, 3H) |

-continued

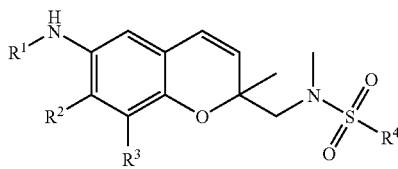

(1)

| Compd. No. | R₁ | R₂ | R₃ | R₄ | Analysis result (NMR/MS) |
|---|---|---|---|---|---|
| 1-1-88 | 4-CNBn | H | H | 4-MePh | m/z 474 [M + H]⁺ |
| 1-1-89 | 4-EtOBn | H | H | 4-MePh | $^1$H NMR(500 MHz, CDCl$_3$) δ 7.62(d, 2H, J=8.3 Hz), 7.29-7.23(m, 4H), 6.85(d, 2H, J=8.6 Hz), 6.56(d, 1H, J=8.6 Hz), 6.56-6.39(m, 12H), 6.35(d, 1H, J=9.8 Hz), 6.29(d, 1H, J=2.8 Hz), 5.63(d, 1H, J=9.8 Hz), 4.15(s, 2H), 4.04-3.99(m, 2H), 3.19(d, 1H, J=14.8 Hz), 3.12(d, 1H, J=14.8 Hz), 2.84(s, 3H), 2.40(s, 3H), 1.54(s, 3H), 1.47-1.38(m, 3H) |
| 1-1-90 | 2-FBn | H | H | 4-MePh | m/z 467 [M + H]⁺ |
| 1-1-91 | 4-FBn | H | H | 4-MePh | $^1$H NMR(500 MHz, CDCl$_3$) δ 7.62(d, 2H, J=8.2 Hz), 7.32-7.25(m, 4H), 7.02-6.98(m, 2H), 6.56(d, 1H, J=8.6 Hz), 6.38(dd, 1H, J=8.6, 2.8 Hz), 6.34(d, 1H, J=4-MePh9.8 Hz), 6.28(d, 1H, J=2.8 Hz), 5.63(d, 1H, J=9.8 Hz), 4.21(s, 2H), 3.18(d, 1H, J=14.3 Hz), 3.13(d, 1H, J=14.3 Hz), 2.84(s, 3H), 2.40(s, 3H), 1.50(s, 3H) |
| 1-1-92 | 3-FBn | H | H | 4-MePh | m/z 467 [M + H]⁺ |
| 1-1-93 | i-Bu | H | H | 4-MePh | $^1$H NMR(500 MHz, CDCl$_3$) δ 7.62(d, 2H, J=8.2 Hz), 7.29-7.2(m, 2H), 6.56(d, 1H, J=8.6 Hz), 6.39-6.35(m, 2H), 6.27(d, 1H, J=2.8 Hz), 5.63(d, 1H, J=9.8 Hz), 3.18(d, 1H, J=14.8 Hz), 3.13(d, 1H, J=14.8 Hz), 2.84(m, 3H), 2.40(s, 3H), 1.83(m, 1H), 1.51(s, 3H), 0.96(d, 6H, J=6.7 Hz) |
| 1-1-94 | (5-methylthien-2-yl)methyl | H | H | 4-MePh | m/z 469 [M + H]⁺ |
| 1-1-95 | 2-NO₂Bn | H | H | 4-MePh | $^1$H NMR(500 MHz CDCl$_3$) δ 8.05-8.02(m, 1H), 7.66-7.61(m, 3H), 7.56-7.55(m, 1H), 7.29-7.26(m, 2H), 6.54(d, 1H, J=8.6 Hz), 6.35-6.30(m, 2H), 6.22(d, 1H, J=2.8 Hz), 5.62(d, 1H, J=9.8 Hz), 4.61(s, 2H), 3.17(d, 1H, J=14.3 Hz), 3.13(d, 1H, J=14.3 Hz), 2.84(s, 3H), 2.40(s, 3H), 1.49(s, 3H) |
| 1-1-96 | 4-NO₂Bn | H | H | 4-MePh | m/z 494 [M + H]⁺ |
| 1-1-97 | 3-NO₂Bn | H | H | 4-MePh | m/z 494 [M + H]⁺ |
| 1-1-98 | PhEt | H | H | 4-MePh | $^1$H NMR(500 MHz, CDCl$_3$) δ 7.62(d, 2H, J=8.3 Hz), 7.31-7.19(m, 7H), 6.56(d, 1H, J=8.6 Hz), 6.39-6.35(m, 2H), 6.28(d, 1H, J=2.8 Hz), 5.64(d, 1H, J=9.8 Hz), 3.31(t, 2H, J=7.0 Hz), 3.19(d, 1H, J=14.3 Hz), 3.12(d, 1H, J=14.3 Hz), 2.90-2.80(m, 5H), 2.40(s, 3H), 1.51(s, 3H) |
| 1-1-99 | n-Pr | H | H | 4-MePh | m/z 401 [M + H]⁺ |
| 1-1-100 | (pyridin-2-yl)methyl | H | H | 4-MePh | $^1$H NMR(500 MHz, CDCl$_3$) δ 8.66(d, 1H, J=4.3 Hz), 7.62(m, 3H), 7.33-7.26(m, 3H), 7.19-7.17(m, 1H), 6.56(d, 1H, J=8.6 Hz), 6.46-6.42(m, 1H), 6.37-6.32(m, 2H), 5.63(d, 1H, J=9.8 Hz), 4.37(s, 2H), 3.18(d, 1H, J=14.8 Hz), 3.12(d, 1H, J=14.8 Hz), 2.84(s, 3H), 2.40(s, 3H), 1.50(s, 3H) |
| 1-1-101 | (pyridin-3-yl)methyl | H | H | 4-MePh | m/z 450 [M + H]⁺ |

-continued

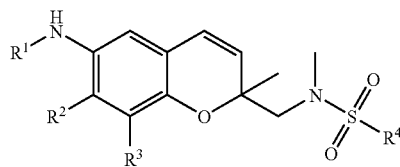

(1)

| Compd. No. | R₁ | R₂ | R₃ | R₄ | Analysis result (NMR/MS) |
|---|---|---|---|---|---|
| 1-1-102 | 4-pyridylmethyl | H | H | 4-MePh | m/z 450 [M + H]⁺ |
| 1-1-103 | 4-(diethoxymethyl)benzyl | H | H | 4-MePh | ¹H NMR(500 MHz, CDCl₃) δ 7.62(d, 2H, J=8.3 Hz), 7.43(d, 2H, J=8.3 Hz), 7.29-7.25(m, 2H), 6.56(d, 1H, J=8.6 Hz), 6.39(dd, 1H, J=8.6, 2.8 Hz), 6.34(d, 1H, J=9.8 Hz), 6.29(d, 1H, J=2.8 Hz), 5.63(d, 1H, J=9.8 Hz), 4.24(s, 2H), 3.64-3.60(m, 2H), 3.55-3.51(m, 2H), 3.18(d, 1H, J=14.3 Hz), 2.84(s, 3H), 2.10(s, 3H), 1.50(s, 3H), 1.26-1.21(m, 6H) |
| 1-1-104 | 2-thienylmethyl | H | H | 4-MePh | m/z 455 [M + H]⁺ |
| 1-1-105 | 3-thienylmethyl | H | H | 4-MePh | ¹H NMR(500 MHz, CDCl₃) δ 7.62(d, 2H, J=8.6 Hz), 7.30-7.25(m, 4H), 7.06-7.04(m, 1H), 6.57(d, 1H, J=8.6 Hz), 6.42(m, 1H), 6.36(d, 1H, J=9.8 Hz), 6.32(d, 1H, J=2.8 Hz) 5.64(d, 1H, J=9.8 Hz), 4.25(s, 2H), 3.18(d, 1H, J=14.8 Hz), 3.13(d, 1H, J=14.8 Hz), 2.84(s, 3H), 2.40(s, 3H), 1.51(s, 3H) |
| 1-1-106 | 4-acetoxybenzyl | H | H | 4-MePh | m/z 507 [M + H]⁺ |
| 1-1-107 | 4-ClBn | H | H | 4-MePh | ¹H NMR(500 MHz, CDCl₃) δ 7.62(d, 2H, J=8.3 Hz)c, 7.29-7.25(m, 4H), 6.55(d, 1H, J=8.6 Hz), 6.39-6.32(m, 2H), 6.26(d, 1H, J=2.8 Hz), 5.63(d, 1H, J=9.8 Hz), 4.21(s, 2H), 3.18(d, 1H, J=14.3 Hz), 3.13(d, 1H, J=14.3 Hz), 2.84(s, 3H), 2.40(s, 3H), 1.50(s, 3H) |
| 1-1-108 | 4-HOBn | H | H | 4-MePh | m/z 465 [M + H]⁺ |
| 1-1-109 | 4-MeOBn | H | H | 4-tert-BuPh | ¹H NMR(500 MHz, CDCl₃) δ 7.67(m, 2H), 7.50-7.47(m, 2H), 7.27-7.25(m, 2H), 6.87-6.85(m, 2H), 6.57(d, 1H, J=8.6 Hz), 6.41(m, 1H), 6.35(d, 1H, J=9.8 Hz), 6.31(d, 1H, J=2.8 Hz), 5.64(d, 1H, J=9.8 Hz), 4.16(s, 2H), 3.79(s, 3H), 3.21(d, 1H, J=14.3 Hz), 3.13(d, 1H, J=14.3 Hz), 2.86(s, 3H), 1.52(s, 3H), 1.33(s, 9H) |
| 1-1-110 | 3-MeOBn | H | H | 4-tert-BuPh | ¹H NMR(500 MHz, CDCl₃) δ 7.66(m, 2H), 7.50-7.47(m, 2H), 7.24(d, 2H, J=7.0 Hz), 6.93-6.90(m, 2H), 6.80(m, 1H), 6.56(d, 1H, J=8.6 Hz), 6.41(m, 1H), 6.35(d, 1H, J=9.8 Hz), 6.30(d, 1H, J=2.8 Hz), 5.63(d, 1H, J=9.8 Hz), 4.21(s, 2H), 3.78(s, 3H), 3.21(d, 1H, J=14.3 Hz), 3.13(d, 1H, J=14.3 Hz), 2.87(s, 3H), 1.52(s, 3H), 1.33(s, 9H) |
| 1-1-111 | 2-MeOBn | H | H | 4-tert-BuPh | m/z 521 [M + H]⁺ |
| 1-1-112 | Bn | H | H | 4-tert-BuPh | m/z 491 [M + H]⁺ |
| 1-1-113 | 4-tert-BuBn | H | H | 4-tert-BuPh | ¹H NMR(500 MHz, CDCl₃) δ 7.66(d, 2H, J=8.5 Hz), 7.48(d, 2H, J=8.5 Hz), 7.35(d, 2H, J=8.6 Hz), 7.29-7.24(m, 2H), 6.57(d, 1H, J=8.6 Hz), |

-continued

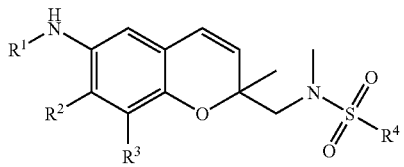

(1)

| Compd. No. | R₁ | R₂ | R₃ | R₄ | Analysis result (NMR/MS) |
|---|---|---|---|---|---|
| | | | | | 6.42(m, 1H), 6.36(d, 1H, J=9.8 Hz), 6.32(d, 1H, J=2.8 Hz), 5.64(6, 1H, J=9.8 Hz), 4.19(s, 2H), 3.22(d, 1H, J=14.3 Hz), 3.13(d, 1H, J=14.3 Hz), 2.86(s, 3H), 1.52(s, 3H), 1.33(m, 18H) |
| 1-1-114 | 3-ClBn | H | H | 4-tert-BuPh | m/z 596 [M + H]⁺ |
| 1-1-115 | 4-CNBn | H | H | 4-tert-BuPh | ¹H NMR(500 MHz, CDCl₃) δ 7.66(d, 2H, J=8.5 Hz), 7.60(d, 2H, J=8.1 Hz), 7.49(d, 2H, J=8.5 Hz), 7.44(d, 2H, J=8.1 Hz), 6.55(d, 1H, J=8.6 Hz), 6.35-6.31(m, 2H) 6.23(d, 1H, J=2.8 Hz), 5.65(d, 1H, J=9.8 Hz), 4.33(s, 2H), 3.19(d, 1H, J=14.3 Hz), 3.13(d, 1H, J=14.3 Hz), 2.85(s, 3H), 1.50(s, 3H), 1.33(s, 9H) |
| 1-1-116 | 4-EtOBn | H | H | 4-tert-BuPh | m/z 535 [M + H]⁺ |
| 1-1-117 | 2-FBn | H | H | 4-tert-BuPh | ¹H NMR(500 MHz, CDCl₃) δ 7.65(d, 2H, J=8.5 Hz), 7.48(d, 2H, J=8.5 Hz), 7.35(m, 1H), 7.25(m, 1H), 7.09-7.03(m, 2H), 6.56(d, 1H, J=1H, J=8.6 Hz), 6.43-6.40(m, 1H), 6.35(d, 1H, J=9.8 Hz), 6.31(d, 1H, J=2.8 Hz), 5.63(d, 1H, J=9.8 Hz), 4.31(s, 2H), 3.21(d, 1H, J=14.3 Hz), 3.13(d, 1H, J=14.3 Hz), 2.86(s, 3H), 1.52(s, 3H), 1.33(s, 9H) |
| 1-1-118 | 4-FBn | H | H | 4-tert-BuPh | m/z 509 [M + H]⁺ |
| 1-1-119 | 3-FBn | H | H | 4-tert-BuPh | ¹H NMR(500 MHz, CDCl₃) δ 7.66(d, 2H, J=8.1 Hz), 7.48(d, 2H, J=8.1 Hz), 7.27(m, 1H), 7.11(m, 1H), 6.94(m, 1H), 6.56(d, 1H, J=1H, J=8.6 Hz), 6.40-6.37(m, 1H), 6.34(d, 1H, J=9.8 Hz), 6.27(d, 1H, J=2.8 Hz), 5.64(d, 1H, J=9.8 Hz), 4.25(s, 2H), 3.21(d, 1H, J=14.3 Hz), 3.15(d, 1H, J=14.3 Hz), 2.86(s, 3H), 1.51(s, 3H), 1.33(s, 9H) |
| 1-1-120 | i-Bu | H | H | 4-tert-BuPh | m/z 457 [M + H]⁺ |
| 1-1-121 | (5-methylthiophen-2-yl)CH₂– | H | H | 4-tert-BuPh | ¹H NMR(500 MHz, CDCl₃) δ 7.66(d, 2H, J=8.5 Hz), 7.48(d, 2H, J=8.5 Hz), 6.74(d, 1H, J=3.2 Hz), 6.57(m, 2H), 6.36(d, 1H, J=9.8 Hz), 6.33(d, 1H, J=2.8 Hz), 5.64(d, 1H, J=9.8 Hz), 4.32(s, 2H), 3.21(d, 1H, J=14.3 Hz), 3.13(d, 1H, J=14.3 Hz), 2.42(s, 3H), 1.52(s, 3H), 1.33(s, 9H) |
| 1-1-122 | 2-NO₂Bn | H | H | 4-tert-BuPh | m/z 536 [M + H]⁺ |
| 1-1-123 | 4-NO₂Bn | H | H | 4-tert-BuPh | ¹H NMR(500 MHz, CDCl₃) δ 8.18(d, 2H, J=8.7 Hz), 7.66(d, 2H, J=8.7 Hz), 7.53-7.48(m, 4H), 6.56(d, 1H, J=1H, J=8.6 Hz), 6.36-5.31(d, 1H, J=9.8 Hz), 6.24(d, 1H, J=2.8 Hz), 5.65(d, 1H, J=9.8 Hz), 4.39(s, 2H), 3.20(d, 1H, J=14.3 Hz), 3.16(d, 1H, J=14.3 Hz), 2.85(s, 3H), 1.50(s, 3H), 1.33(s, 9H) |
| 1-1-125 | 3-NO₂Bn | H | H | 4-tert-BuPh | m/z 536 [M + H]⁺ |
| 1-1-125 | PhEt | H | H | 4-tert-BuPh | ¹H NMR(500 MHz, CDCl₃) δ 7.67-7.65(m, 2H), 7.49-7.47(m, 2H), 7.31-7.19(m, 7H), 6.57(d, 1H, J=8.6 Hz), 6.34(m, 2H), 6.28(d, 1H, J=2.8 Hz), 5.64(d, 1H, J=9.8 Hz), 3.32(t, 2H, J=7.0 Hz), 3.21(d, 1H, J=14.3 Hz), 3.14(d, 1H, J=14.3 Hz), 2.88(m, 4H), 1.52(s, 3H), 1.32(s, 9H) |
| 1-1-126 | n-Pr | H | H | 4-tert-BuPh | m/z 423 [M + H]⁺ |

-continued

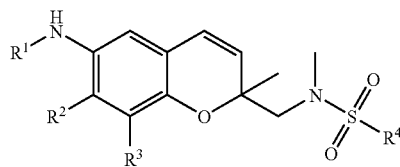

(1)

| Compd. No. | R₁ | R₂ | R₃ | R₄ | Analysis result (NMR/MS) |
|---|---|---|---|---|---|
| 1-1-127 | 2-pyridylmethyl | H | H | 4-tert-BuPh | ¹H NMR(500 MHz, CDCl₃) δ 8.56(m, 1H), 7.68-7.63(m, 2H), 7.50-7.47(m, 2H), 7.31(m, 1H), 6.95(m, 1H), 6.57(d, 1H, J=8.6 Hz), 6.45(m, 1H), 6.37-6.33(m, 2H), 5.63(d, 1H, J=9.8 Hz), 4.37(s, 2H), 3.21(d, 1H, J=14.3 Hz), 3.13(d, 1H, J=14.3 Hz), 2.86(s, 3H), 1.51(s, 3H), 1.32(s, 9H) |
| 1-1-128 | 3-pyridylmethyl | H | H | 4-tert-BuPh | m/z 492 [M + H]⁺ |
| 1-1-129 | 4-pyridylmethyl | H | H | 4-tert-BuPh | ¹H NMR(500 MHz, CDCl₃) δ 8.55-8.52(m, 2H), 7.66(d, 2H, J=8.4 Hz), 7.49(d, 2H, J=8.4 Hz), 7.29-7.26(m, 2H), 6.56(d, 1H, J=8.6 Hz), 6.36-6.31(m, 2H), 6.23(d, 1H, J=2.8 Hz), 5.65(d, 1H, J=9.8 Hz), 4.30(s, 2H), 3.21(d, 1H, J=14.3 Hz), 3.15(d, 1H, J=14.3 Hz), 2.86(s, 3H), 1.50(s, 3H), 1.33(s, 9H) |
| 1-1-130 | 4-(diethoxymethyl)benzyl | H | H | 4-tert-BuPh | m/z 593 [M + H]⁺ |
| 1-1-131 | 2-thienylmethyl | H | H | 4-tert-BuPh | ¹H NMR(500 MHz, CDCl₃) δ 7.67-7.65(m, 2H), 7.50-7.48(m, 2H), 7.20(d, 1H, J=5.0 Hz), 6.98-6.94(m, 2H), 6.58(m, 1H), 6.38-6.34(m, 2H), 5.66-5.63(m, 1H), 4.42(s, 2H), 3.21(d, 1H, J=14.3 Hz), 3.15(d, 1H, J=14.3 Hz), 2.86(s, 3H), 1.52(s, 3H), 1.33(s, 9H) |
| 1-1-132 | 3-thienylmethyl | H | H | 4-tert-BuPh | m/z 497 [M + H]⁺ |
| 1-1-133 | 4-acetoxybenzyl | H | H | 4-tert-BuPh | ¹H NMR(500 MHz, CDCl₃) δ 7.66(d, 2H, J=8.2 Hz), 7.48(d, 2H, J=8.2 Hz), 7.35(d, 2H, J=8.3 Hz), 7.04(d, 2H, J=8.3 Hz), 6.57(d, 1H, J=8.6 Hz), 6.39(dd, 1H, J=8.6, 2.8 Hz), 6.35(d, 1H, J=9.8 Hz), 6.29(d, 1H, J=2.8 Hz), 5.64(d, 1H, J=9.8 Hz), 4.23(s, 2H), 3.21(d, 1H, J=14.3 Hz), 3.14(d, 1H, J=14.3 Hz), 2.86(s, 3H), 2.29(s, 3H), 1.52(s, 3H), 1.33(s, 9H) |
| 1-1-134 | 4-ClBn | H | H | 4-tert-BuPh | m/z 526 [M + H]⁺ |
| 1-1-135 | 4-HOBn | H | H | 4-tert-BuPh | m/z 507 [M + H]⁺ |
| 1-1-136 | 4-MeOBn | H | H | 2,4,6-tri-MePh | m/z 507 [M + H]⁺ |
| 1-1-137 | 3-MeOBn | H | H | 2,4,6-tri-MePh | ¹H NMR(500 MHz, CDCl₃) δ 7.27-7.23(m, 2H), 6.95-6.92(m, 4H), 6.81(d, 1H, J=8.4 Hz), 6.56(d, 1H, J=8.4 Hz), 6.43-6.40(m, 1H), 6.32-6.29(m, 2H), 4.23(s, 2H), 3.79(s, 3H), 3.42(d, 1H, J=14.8 Hz), 3.38(d, 1H, J=14.8 Hz), 2.82(s, 3H), 2.56(s, 6H), 2.28(s, 3H), 1.38(s, 3H) |
| 1-1-138 | 2-MeOBn | H | H | 2,4,6-tri-MePh | m/z 507 [M + H]⁺ |

-continued

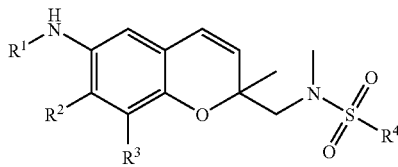

(1)

| Compd. No. | R₁ | R₂ | R₃ | R₄ | Analysis result (NMR/MS) |
|---|---|---|---|---|---|
| 1-1-139 | Bn | H | H | 2,4,6-tri-MePh | $^1$H NMR(500 MHz, CDCl$_3$) δ 7.37-7.24(m, 5H), 6.92(s, 2H), 6.57(d, 1H, J=8.6 Hz), 6.44-6.41(dd, 1H, J=8.6, 2.8 Hz), 6.32-6.29(m, 2H), 5.46(d, 1H, J=9.8 Hz), 4.25(s, 2H), 3.42(d, 1H, J=14.8 Hz), 3.38(d, 1H, J=14.8 Hz), 2.82(s, 3H), 2.56(s, 6H), 2.28(s, 3H), 1.39(s, 3H) |
| 1-1-140 | 4-tert-BuBn | H | H | 2,4,6-tri-MePh | m/z 533 [M + H]$^+$ |
| 1-1-141 | 3-ClBn | H | H | 2,4,6-tri-MePh | $^1$H NMR(500 MHz, CDCl$_3$) δ 7.36-7.22(m, 4H), 6.92(s, 2H), 6.56(d, 1H, J=8.6 Hz), 6.40-6.37(dd, 1H, J=8.6, 2.8 Hz), 6.30-6.27(m, 2H), 5.47(d, 1H, J=9.8 Hz), 4.24(s, 2H), 3.42(d, 1H, J=14.8 Hz), 3.38(d, 1H, J=14.8 Hz), 2.82(s, 3H), 2.56(s, 6H), 2.28(s, 3H), 1.39(s, 3H) |
| 1-1-142 | 4-CNBn | H | H | 2,4,6-tri-MePh | m/z 502 [M + H]$^+$ |
| 1-1-143 | 4-EtOBn | H | H | 2,4,6-tri-MePh | m/z 521 [M + H]$^+$ |
| 1-1-144 | 2-FBn | H | H | 2,4,6-tri-MePh | $^1$H NMR(500 MHz, CDCl$_3$) δ 7.37(m, 1H), 7.26-7.22(m, 2H), 7.11-7.04(m, 2H), 6.92(s, 2H), 6.57(d, 1H, J=8.6 Hz), 6.44.-6.41(dd, 1H, J=8.6, 2.8 Hz), 6.32-6.29(m, 2H), 5.46(d, 1H, J=9.8 Hz), 4.32(s, 3H), 3.42(d, 1H, J=14.8 Hz), 3.37(d, 1H, J=14.8 Hz), 2.82(s, 3H), 2.56(s, 6H), 2.28(s, 3H), 1.39(s, 3H) |
| 1-1-145 | 4-FBn | H | H | 2,4,6-tri-MePh | m/z 495 [M + H]$^+$ |
| 1-1-146 | 3-FBn | H | H | 2,4,6-tri-MePh | m/z 495 [M + H]$^+$ |
| 1-1-147 | i-Bu | H | H | 2,4,6-tri-MePh | $^1$H NMR(500 MHz, CDCl$_3$) δ 6.93(s, 2H), 6.57(d, 1H, J=8.6 Hz), 6.40(dd, 1H, J=8.6, 2.8 Hz), 6.33(d, 1H, J=9.8 Hz), 6.28(d, 1H, J=2.8 Hz), 5.48(d, 1H, J=9.8 Hz), 3.42(d, 1H, J=14.8 Hz), 3.38(d, 1H, J=14.8 Hz), 2.86(d, 2H, J=6.7 Hz), 2.83(s, 3H), 2.57(s, 6H), 2.29(s, 3H), 1.88-1.82(m, 1H), 1.40(s, 3H), 0.97(d, 6H, J=6.7 Hz) |
| 1-1-148 | 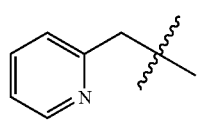 | H | H | 2,4,6-tri-MePh | m/z 497 [M + H]$^+$ |
| 1-1-149 | 2-NO$_2$Bn | H | H | 2,4,6-tri-MePh | m/z 522 [M + H]$^+$ |
| 1-1-150 | 4-NO$_2$Bn | H | H | 2,4,6-tri-MePh | $^1$H NMR(500 MHz, CDCl$_3$) δ 8.21-8.17(m, 2H), 7.52(d, 2H, J=8.7 Hz), 6.93(s, 2H), 6.56(m, 1H), 6.36(dd, 1H, J=8.6, 2.8 Hz), 6.28(d, 1H, J=8.6 Hz), 6.24(d, 1H, J=2.8 Hz), 5.50(d, 1H, J=9.8 Hz), 4.40(s, 2H), 3.43(d, 1H, J=14.8 Hz), 3.37(d, 1H, J=14.8 Hz), 2.81(s, 3H), 2.56(s, 6H), 2.29(s, 3H), 1.40(s, 3H) |
| 1-1-151 | 3-NO$_2$Bn | H | H | 2,4,6-tri-MePh | m/z 522 [M + H]$^+$ |
| 1-1-152 | PhEt | H | H | 2,4,6-tri-MePh | m/z 491 [M + H]$^+$ |
| 1-1-153 | n-Pr | H | H | 2,4,6-tri-MePh | $^1$H NMR(500 MHz, CDCl$_3$) δ 6.93(s, 2H), 6.57(d, 1H, J=8.6 Hz), 6.40(dd, 1H, J=8.6, 2.8 Hz), 6.33(d, 1H, J=9.8 Hz), 6.30(d, 1H, J=2.8 Hz), 5.48(d, 1H, J=9.8 Hz), 3.42(d, 1H, J=14.8 Hz), 3.38(d, 1H, J=14.8 Hz), 3.02(t, 2H, J=7.0 Hz), 2.82(s, 3H), 2.57(s, 6H), 2.29(s, 3H), 1.65-1.59(m, 2H), 1.41(s, 3H), 1.00-0.96(m, 3H) |
| 1-1-154 | 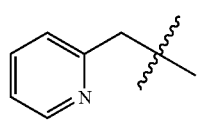 | H | H | 2,4,6-tri-MePh | m/z 478 [M + H]$^+$ |

-continued

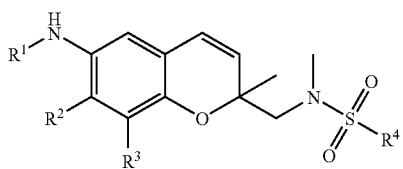

(1)

| Compd. No. | R₁ | R₂ | R₃ | R₄ | Analysis result (NMR/MS) |
|---|---|---|---|---|---|
| 1-1-155 | 3-pyridylmethyl | H | H | 2,4,6-tri-MePh | m/z 478 [M + H]⁺ |
| 1-1-156 | 4-pyridylmethyl | H | H | 2,4,6-tri-MePh | m/z 478 [M + H]⁺ |
| 1-1-157 | 4-(diethoxymethyl)benzyl | H | H | 2,4,6-tri-MePh | m/z 579 [M + H]⁺ |
| 1-1-158 | 2-thienylmethyl | H | H | 2,4,6-tri-MePh | m/z 483 [M + H]⁺ |
| 1-1-159 | 3-thienylmethyl | H | H | 2,4,6-tri-MePh | ¹H NMR(500 MHz, CDCl₃) δ 7.31-7.28(m, 1H), 7.78(s, 1H), 7.07(d, 1H, J=4.9 Hz), 6.93(s, 2H), 6.58(d, 1H, J=8.6 Hz), 6.44(dd, 1H, J=8.6, 2.8 Hz), 6.32(m, 2H), 5.48(d, 1H, J=9.8 Hz), 4.26(s, 2H), 3.42(d, 1H, J=14.8 Hz), 3.38(d, 1H, J=14.8 Hz), 2.82(s, 3H), 2.57(s, 6H), 2.29(s, 3H), 1.39(s, 3H) |
| 1-1-160 | 4-acetoxybenzyl | H | H | 2,4,6-tri-MePh | m/z 535 [M + H]⁺ |
| 1-1-161 | 4-ClBn | H | H | 2,4,6-tri-MePh | m/z 512 [M + H]⁺ |
| 1-1-162 | 4-HOBn | H | H | 2,4,6-tri-MePh | m/z 493 [M + H]⁺ |
| 1-1-163 | 4-MeOBn | H | H | Bn | ¹H NMR(500 MHz, CDCl₃) δ 7.33(m, 5H), 7.28-7.24(m, 2H), 6.87(d, 2H, J=8.6 Hz), 6.57(d, 1H, J=8.6 Hz), 6.42(dd, 1H, J=8.6, 2.8 Hz), 6.32-6.30(m, 2H), 5.51(d, 1H, J=9.8 Hz), 4.21(s, 2H), 4.17(s, 2H), 3.79(s, 3H), 3.11(d, 1H, J=14.8 Hz), 2.99(d, 1H, J=14.8 Hz), 1.33(s, 3H) |
| 1-1-164 | 3-MeOBn | H | H | Bn | m/z 479 [M + H]⁺ |
| 1-1-165 | 2-MeOBn | H | H | Bn | m/z 479 [M + H]⁺ |
| 1-1-166 | Bn | H | H | Bn | m/z 449 [M + H]⁺ |
| 1-1-167 | 4-tert-BuBn | H | H | Bn | ¹H NMR(500 MHz, CDCl₃) δ 7.38-7.24(m, 9H), 6.58(d, 1H, J=8.6 Hz), 6.46-6.43(dd, 1H, J=8.6, 2.8 Hz), 6.34-6.31(m, 2H), 5.52(d, 1H, J=9.8 Hz), 4.22(s, 2H), 4.21(s, 2H), 3.12(d, 1H, J=14.8 Hz), 2.99(d, 1H, J=14.8 Hz), 2.88(s, 3H), 1.32(s, 9H) |
| 1-1-168 | 3-ClBn | H | H | Bn | m/z 484 [M + H]⁺ |

-continued

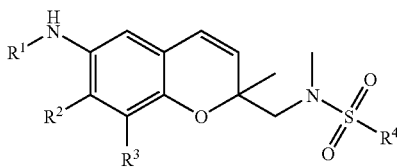

(1)

| Compd. No. | R₁ | R₂ | R₃ | R₄ | Analysis result (NMR/MS) |
|---|---|---|---|---|---|
| 1-1-169 | 4-CNBn | H | H | Bn | $^1$H NMR(500 MHz, CDCl$_3$) δ 7.62-7.60(m, 2H), 7.47(d, 2H, J=8.2 Hz), 7.34(m, 5H), 6.56(d, 1H, J=8.6 Hz), 6.36(dd, 1H, J=8.6, 2.8 Hz), 6.28(d, 1H, J=8.6 Hz), 6.24(d, 1H, J=2.8 Hz), 5.53(d, 1H, J=9.8 Hz), 4.35(s, 2H), 4.22(s, 2H), 3.12(d, 1H, J=14.8 Hz), 2.98(d, 1H, J=14.8 Hz), 2.87(s, 3H), 1.31(s, 3H) |
| 1-1-170 | 4-EtOBn | H | H | Bn | m/z 493 [M + H]⁺ |
| 1-1-171 | 2-FBn | H | H | Bn | $^1$H NMR(500 MHz, CDCl$_3$) δ 7.38-7.33(m, 6H), 7.24(m, 1H), 7.10-7.04(m, 2H), 6.57(d, 1H, J=8.6 Hz), 6.44(dd, 1H, J=8.6, 2.8 Hz), 6.33-6.30(m, 2H), 5.51(d, 1H, J=9.8 Hz), 4.33(s, 2H), 4.22(s, 2H), 3.11(d, 1H, J=14.8 Hz), 2.99(d, 1H, J=14.8 Hz), 2.87(s, 3H), 1.32(s, 3H) |
| 1-1-172 | 4-FBn | H | H | Bn | m/z 467 [M + H]⁺ |
| 1-1-173 | 3-FBn | H | H | Bn | m/z 467 [M + H]⁺ |
| 1-1-174 | i-Bu | H | H | Bn | $^1$H NMR(500 MHz, CDCl$_3$) δ 7.34(m, 5H), 6.58(d, 1H, J=8.6 Hz), 6.41(dd, 1H, J=8.6, 2.8 Hz), 6.33(d, 1H, J=8.6 Hz), 6.28(m, 2H), 5.51(d, 1H, J=9.8 Hz), 4.22(s, 2H), 3.12(d, 1H, J=14.8 Hz), 2.99(d, 1H, J=14.8 Hz), 2.88(m, 5H), 1.88-1.82(m, 1H), 1.33(s, 3H), 0.97(d, 6H, J=6.7 Hz) |
| 1-1-175 | ![thiophene] | H | H | Bn | m/z 469 [M + H]⁺ |
| 1-1-176 | 2-NO₂Bn | H | H | Bn | m/z 494 [M + H]⁺ |
| 1-1-177 | 4-NO₂Bn | H | H | Bn | $^1$H NMR(500 MHz, CDCl$_3$) δ 8.21-8.17(m, 2H), 7.52(d, 2H, J=8.3 Hz), 7.34(m, 5H), 6.56(d, 1H, J=8.6 Hz), 6.37(dd, 1H, J=8.6, 2.8 Hz), 6.28(d, 1H, J=8.6 Hz), 6.25(d, 1H, J=2.8 Hz), 5.53(d, 1H, J=9.8 Hz), 4.40(s, 2H), 4.22(s, 2H), 3.13(d, 1H, J=14.8 Hz), 2.98(d, 1H, J=14.8 Hz), 2.87(s, 3H), 1.31(s, 3H) |
| 1-1-178 | 3-NO₂Bn | H | H | Bn | m/z 494 [M + H]⁺ |
| 1-1-179 | PhEt | H | H | Bn | m/z 463 [M + H]⁺ |
| 1-1-180 | n-Pr | H | H | Bn | $^1$H NMR(500 MHz, CDCl$_3$) δ 7.34(m, 5H), 6.57(d, 1H, J=8.6 Hz), 6.42(dd, 1H, J=8.6, 2.8 Hz), 6.33(d, 1H, J=8.6 Hz), 6.30(d, 1H, J=2.8 Hz), 5.52(d, 1H, J=9.8 Hz), 4.23(s, 2H), 3.12(d, 1H, J=14.8 Hz), 3.04-2.97(m, 2H), 2.89(s, 3H), 1.65-1.60(m, 2H), 1.33(s, 3H), 1.00-0.97(m, 3H) |
| 1-1-181 | 2-pyridylmethyl | H | H | Bn | m/z 450 [M + H]⁺ |
| 1-1-182 | 3-pyridylmethyl | H | H | Bn | m/z 450 [M + H]⁺ |
| 1-1-183 | 4-pyridylmethyl | H | H | Bn | m/z 450 [M + H]⁺ |

-continued

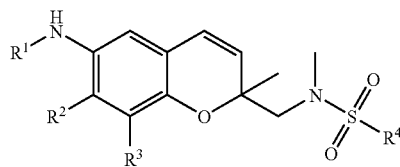

(1)

| Compd. No. | R₁ | R₂ | R₃ | R₄ | Analysis result (NMR/MS) |
|---|---|---|---|---|---|
| 1-1-184 | (4-(diethoxymethyl)benzyl group) | H | H | Bn | m/z 551 [M + H]⁺ |
| 1-1-185 | (2-thienylmethyl) | H | H | Bn | m/z 455 [M + H]⁺ |
| 1-1-186 | (3-thienylmethyl) | H | H | Bn | m/z 455 [M + H]⁺ |
| 1-1-187 | (4-acetoxybenzyl) | H | H | Bn | m/z 507 [M + H]⁺ |
| 1-1-188 | 4-ClBn | H | H | Bn | ¹H NMR(500 MHz, CDCl₃) δ 7.34(m, 5H), 7.29(m, 4H), 6.56(d, 1H, J=8.6 Hz), 6.40(dd, 1H, J=8.6, 2.8 Hz), 6.32-6.27(m, 2H), 5.53(d, 1H, J=9.8 Hz), 4.24(s, 2H), 4.22(s, 2H), 3.12(d, 1H, J=14.8 Hz), 2.99(d, 1H, J=14.8 Hz), 2.87(s, 3H), 1.32(s, 3H) |
| 1-1-189 | 4-HOBn | H | H | Bn | m/z 465 [M + H]⁺ |
| 1-1-190 | 4-MeOBn | H | H | 2,5-di-MeOPh | m/z 525 [M + H]⁺ |
| 1-1-191 | 3-MeOBn | H | H | 2,5-di-MeOPh | ¹H NMR(500 MHz, CDCl₃) δ 7.47(m, 1H), 7.26-7.23(m, 2H), 7.01-7.00(m, 1H), 6.95-6.87(m, 3H), 6.75(m, 1H), 6.58(d, 1H, J=8.6 Hz), 6.43(m, 1H), 6.36-6.31(m, 2H), 5.63(d, 1H, J=9.8 Hz), 4.23(s, 2H), 3.82(s, 3H), 3.79(s, 6H), 3.44(d, 1H, J=14.8 Hz), 3.38(d, 1H, J=14.8 Hz), 2.87(s, 3H), 1.49(s, 3H) |
| 1-1-192 | 2-MeOBn | H | H | 2,5-di-MeOPh | m/z 525 [M + H]⁺ |
| 1-1-193 | Bn | H | H | 2,5-di-MeOPh | ¹H NMR(500 MHz, CDCl₃) δ 7.47(m, 1H), 7.46-7.35(m, 4H), 7.26(m, 2H), 7.01(m, 1H), 6.90-6.87(m, 1H), 6.59(d, 1H, J=8.6 Hz), 6.43(m, 1H), 6.36-6.32(m, 2H), 5.63(d, 1H, J=9.8 Hz), 4.25(s, 2H), 3.82(s, 3H), 3.79(s, 3H), 3.43(d, 1H, J=14.8 Hz), 3.39(d, 1H, J=14.8 Hz), 2.87(s, 3H), 1.49(s, 3H) |
| 1-1-194 | 4-tert-BuBn | H | H | 2,5-di-MeOPh | m/z 551 [M + H]⁺ |
| 1-1-195 | 3-ClBn | H | H | 2,5-di-MeOPh | ¹H NMR(500 MHz, CDCl₃) δ 7.47(s, 1H), 7.36(s, 1H), 7.26-7.24(m, 3H), 7.01(m, 1H), 6.90(m, 1H), 6.58(m, 1H), 6.41-6.28(m, 3H), 5.66-5.63(m, 1H), 4.25(s, 2H), 3.82(s, 3H), 3.80(s, 3H), 3.46-3.40(m, 2H), 2.87(s, 3H), 1.49(s, 3H) |
| 1-1-196 | 4-CNBn | H | H | 2,5-di-MeOPh | m/z 520 [M + H]⁺ |
| 1-1-197 | 4-EtOBn | H | H | 2,5-di-MeOPh | ¹H NMR(500 MHz, CDCl₃) δ 7.47(s, 1H), 7.27-7.24(m, 3H), 7.01(m, 1H), 6.90-6.84(m, 3H), 6.58(d, 1H, J=8.6 Hz), 6.44-6.41(m, 1H), 6.36-6.32(m, 2H), 5.63(d, 1H, J=9.8 Hz), 4.17(s, 2H), 4.04-3.99(m, 2H), 3.82(s, 3H), 3.79(s, |

-continued

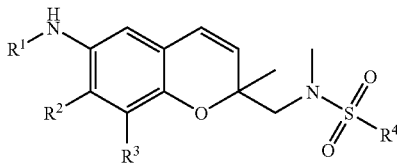

(1)

| Compd. No. | R₁ | R₂ | R₃ | R₄ | Analysis result (NMR/MS) |
|---|---|---|---|---|---|
| | | | | | 3H), 3.43(d, 1H, J=14.8 Hz), 3.38(d, 1H, J=14.8 Hz), 2.87(s, 3H), 1.49(s, 3H), 1.40(t, 3H, J=7.0 Hz) |
| 1-1-198 | 2-FBn | H | H | 2,5-di-MeOPh | m/z 513 [M + H]⁺ |
| 1-1-199 | 4-FBn | H | H | 2,5-di-MeOPh | ¹H NMR(500 MHz, CDCl₃) δ 7.46(s, 1H), 7.34-7.30(m, 2H), 7.04-7.00(m, 3H), 6.89(d, 1H, J=9.0 Hz), 6.59(d, 1H, J=8.6 Hz), 6.42(m, 1H), 6.35(d, 1H, J=9.8 Hz), 6.31(d, 1H, J=2.8 Hz), 5.65(d, 1H, J=9.8 Hz), 4.23(s, 2H), 3.82(s, 3H), 3.80(s, 3H), 3.43(d, 1H, J=14.9 Hz), 3.39(d, 1H, J=14.9 Hz), 2.87(s, 3H), 1.49(s, 3H) |
| 1-1-200 | 3-FBn | H | H | 2,5-di-MeOPh | m/z 513 [M + H]⁺ |
| 1-1-201 | i-Bu | H | H | 2,5-di-MeOPh | ¹H NMR(500 MHz, CDCl₃) δ 7.46(d, 1H, J=3.1 Hz), 7.03-7.01(m, 1H), 6.89(d, 1H, J=9.0 Hz), 6.59(d, 1H, J=8.5 Hz), 6.41-6.36(m, 2H), 6.29(d, 1H, J=2.5 Hz), 5.64(dd, 1H, J=8.6, 2.8 Hz), 3.82(s, 3H), 3.80(s, 3H), 3.43(d, 1H, J=14.8 Hz), 3.38(d, 1H, J=14.8 Hz), 2.87(m, 5H), 1.88-1.82(m, 1H), 1.50(s, 3H), 0.97(d, 6H, J=6.7 Hz) |
| 1-1-202 | 5-methylthiophen-2-ylmethyl | H | H | 2,5-di-MeOPh | ¹H NMR(500 MHz, CDCl₃) δ 7.46(d, 1H, J=3.1 Hz), 7.04-7.00(m, 1H), 6.89(d, 1H, J=9.0 Hz), 6.76(d, 1H, J=3.0 Hz), 6.59(m, 2H), 6.47-6.44(m, 1H), 6.37-6.35(m, 2H), 5.64(d, 1H, J=9.8 Hz), 4.34(s, 2H), 3.82(s, 3H), 3.79(s, 3H), 3.44(d, 1H, J=14.3 Hz), 3.38(d, 1H, J=14.3 Hz), 2.87(s, 3H), 2.44(s, 3H), 1.49(s, 3H) |
| 1-1-203 | 2-NO₂Bn | H | H | 2,5-di-MeOPh | m/z 540 [M + H]⁺ |
| 1-1-204 | 4-NO₂Bn | H | H | 2,5-di-MeOPh | ¹H NMR(500 MHz, CDCl₃) δ 8.22(s, 1H), 8.10(d, 1H J=8.1 Hz), 7.70(d, 1H, J=7.7 Hz), 7.50(m, 1H), 7.45(m, 1H), 7.03-7.00(m, 1H), 6.89(d, 1H, J=9.0 Hz), 6.58(d, 1H, J=8.6 Hz), 6.39-6.32(m, 2H), 6.28(d, 1H, J=2.5 Hz), 5.65(d, 1H, J=9.8 Hz), 4.39(s, 2H), 3.82(s, 3H), 3.79(s, 3H), 3.43(d, 1H, J=14.9 Hz), 3.40(d, 1H, J=14.9 Hz), 2.86(s, 3H), 1.48(s, 3H) |
| 1-1-205 | 3-NO₂Bn | H | H | 2,5-di-MeOPh | m/z 540 [M + H]⁺ |
| 1-1-206 | PhEt | H | H | 2,5-di-MeOPh | m/z 509 [M + H]⁺ |
| 1-1-207 | n-Pr | H | H | 2,5-di-MeOPh | ¹H NMR(500 MHz, CDCl₃) δ 7.46(d, 1H, J=3.1 Hz), 7.04-7.01(m, 1H), 6.89(d, 1H, J=9.0 Hz), 6.59(d, 1H, J=8.5 Hz), 6.43-6.36(m, 2H), 6.31(d, 1H, J=2.5 Hz), 5.64(d, 1H, J=9.8 Hz), 3.82(s, 3H), 3.80(s, 3H), 3.44(d, 1H, J=14.8 Hz), 3.38(d, 1H, J=14.8 Hz), 3.01(t, 2H, J=7.0 Hz), 1.66-1.58(m, 2H), 1.50(s, 3H), 0.98(t, 3H, J=7.0 Hz) |
| 1-1-208 | pyridin-2-ylmethyl | H | H | 2,5-di-MeOPh | m/z 496 [M + H]⁺ |

-continued

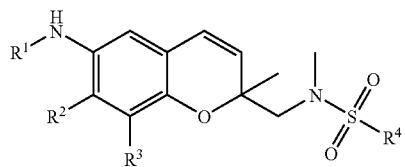

(1)

| Compd. No. | R₁ | R₂ | R₃ | R₄ | Analysis result (NMR/MS) |
|---|---|---|---|---|---|
| 1-1-209 | 3-pyridylmethyl | H | H | 2,5-di-MeOPh | m/z 496 [M + H]⁺ |
| 1-1-210 | 4-pyridylmethyl | H | H | 2,5-di-MeOPh | ¹H NMR(500 MHz, CDCl₃) δ 8.54(d, 1H, J=5.4 Hz), 7.46(d, 1H, J=2.8 Hz), 7.30-7.27(m, 2H), 7.20(m, 1H), 6.90(d, 1H, J=9.9 Hz), 6.58(d, 1H, J=8.6 Hz), 6.37-6.31(m, 2H), 6.26(d, 1H, J=2.7 Hz), 5.65(d, 1H, J=9.8 Hz), 4.31(s, 2H), 3.82(s, 3H), 3.79(s, 3H), 3.42(d, 1H, J=14.8 Hz), 3.40(d, 1H, J=14.8 Hz), 2.86(s, 3H), 1.48(s, 3H) |
| 1-1-211 | 4-(diethoxymethyl)benzyl | H | H | 2,5-di-MeOPh | m/z 597 [M + H]⁺ |
| 1-1-212 | 2-thienylmethyl | H | H | 2,5-di-MeOPh | ¹H NMR(500 MHz, CDCl₃) δ 7.45(d, 1H, J=3.3 Hz), 7.20(m, 1H), 7.01-6.95(m, 2H), 6.89(d, 1H, J=9.0 Hz), 6.59(d, 1H, J=8.6 Hz), 6.47(m, 1H), 6.37-6.34(m, 2H), 5.64(d, 1H, J=9.8 Hz), 4.44(s, 2H), 3.82(s, 3H), 3.79(s, 3H), 3.44(d, 1H, J=14.8 Hz), 3.39(d, 1H, J=14.8 Hz), 1.49(s, 3H) |
| 1-1-213 | 3-thienylmethyl | H | H | 2,5-di-MeOPh | m/z 501 [M + H]⁺ |
| 1-1-214 | 4-acetoxybenzyl | H | H | 2,5-di-MeOPh | m/z 553 [M + H]⁺ |
| 1-1-215 | 4-ClBn | H | H | 2,5-di-MeOPh | m/z 530 [M + H]⁺ |
| 1-1-216 | 4-HOBn | H | H | 2,5-di-MeOPh | m/z 511 [M + H]⁺ |
| 1-1-217 | 4-MeOBn | H | H | 4-ClPh | ¹H NMR(500 MHz, CDCl₃) δ 7.67(d, 2H, J=9.3 Hz), 7.46(d, 2H, J=9.3 Hz), 7.26(d, 2H, J=8.1 Hz), 6.86(d, 2H, J=8.1 Hz), 6.56(d, 1H, J=8.5 Hz), 6.41-6.38(m, 1H), 6.36(d, 1H, J=9.8 Hz), 6.30(d, 1H, J=2.4 Hz), 5.61(d, 1H, J=9.8 Hz), 4.16(s, 2H), 3.79(s, 3H), 3.19(d, 1H, J=14.3 Hz), 3.15(d, 1H, J=14.3 Hz), 2.86(s, 3H), 1.49(s, 3H) |
| 1-1-218 | 3-MeOBn | H | H | 4-ClPh | ¹H NMR(500 MHz, CDCl₃) δ 7.76(d, 2H, J=8.5 Hz), 7.46(d, 2H, J=8.5 Hz), 7.25-7.22(m, 1H), 6.93-6.90(m, 1H), 6.56(d, 1H, J=8.5 Hz), 6.41-6.39(m, 1H), 6.35(d, 1H, J=9.8 Hz), 6.30(d, 1H, J=2.7 Hz), 5.61(d, 1H, J=9.8 Hz), 4.21(s, 2H), 3.78(s, 3H), 3.18(d, 1H, J=14.3 Hz), 3.15(d, 1H, J=14.3 Hz), 2.86(s, 3H), 1.49(s, 3H) |
| 1-1-219 | 2-MeOBn | H | H | 4-ClPh | ¹H NMR(500 MHz, CDCl₃) δ 7.68-7.66(m, 2H), 7.46-7.44(m, 2H), 7.25-7.23(m, 2H), 6.89-6.86(m, 2H), 6.55(d, 1H, J=8.5 Hz), |

-continued

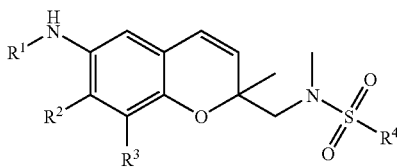

(1)

| Compd. No. | R₁ | R₂ | R₃ | R₄ | Analysis result (NMR/MS) |
|---|---|---|---|---|---|
| | | | | | 6.44-6.43(m, 1H), 6.36-5.68(m, 2H), 5.60(d, 1H, J=9.8 Hz), 4.24(s, 2H), 3.88(s, 3H), 3.23-3.12(m, 2H), 2.88(s, 3H), 1.49(s, 3H) |
| 1-1-220 | Bn | H | H | 4-ClPh | $^1$H NMR(500 MHz, (CDCl$_3$) δ 7.67(d, 2H, J=8.5 Hz), 7.45(d, 2H, J=8.5 Hz), 7.34-7.31(m, 4H), 7.27-7.25(m, 1H), 6.56(d, 1H, J=8.5 Hz), 6.41(dd, 1H, J=8.5 Hz, J=2.7 Hz), 6.35(d, 1H, J=9.8 Hz), 6.31(d, 1H, J=2.7 Hz), 5.61(d, 1H, J=9.8 Hz), 4.24(s, 2H), 3.18(d, 1H, J=14.3 Hz), 3.15(d, 1H, J=14.3 Hz), 2.86(s, 3H), 1.49(s, 3H) |
| 1-1-221 | 4-tert-BuBn | H | H | 4-ClPh | $^1$H NMR(500 MHz, CDCl$_3$): 7.68(d, 2H, J=8.5 Hz), 7.46(d, 2H, J=8.5 Hz), 7.36(d, 2H, J=8.1 Hz), 7.28(d, 2H, J=8.1 Hz), 6.57(d, 1H, J=8.5 Hz), 6.42(dd, 1H, J=8.5 Hz, J=2.7 Hz), 6.36(d, 1H, J=9.8 Hz), 6.31(d, 1H, J=2.7 Hz), 5.62(d, 1H, J=9.8 Hz), 4.19(s, 2H), 3.18-3.16(m, 2H), 2.86(s, 3H), 1.49(s, 3H), 1.31(s, 9H) |
| 1-1-222 | 3-ClBn | H | H | 4-ClPh | $^1$H NMR(500 MHz, CDCl$_3$) δ 7.68-7.67(m, 2H), 7.46-7.45(m, 2H), 7.34(s, 1H), 7.25-7.22(m, 3H), 6.56(d, 1H, J=8.5 Hz), 6.38-6.33(m, 2H), 6.27(d, 1H, J=2.7 Hz), 5.62(d, 1H, J=9.8 Hz), 4.23(s, 2H), 3.19(d, 1H, J=14.3 Hz), 3.16(d, 1H, J=14.3 Hz), 2.86(s, 3H), 1.49(s, 3H) |
| 1-1-223 | 4-CNBn | H | H | 4-ClPh | $^1$H NMR(500 MHz, CDCl$_3$) δ 7.68(d, 2H, J=8.4 Hz), 7.61(d, 2H, J=8.1 Hz), 7.47-7.45(m, 4H), 6.55(d, 1H, J=8.5 Hz), 6.35-6.32(m, 2H), 6.23(d, 1H, J=2.7 Hz), 5.63(d, 1H, J=9.8 Hz), 4.34(s, 2H), 3.17(s, 2H), 2.85(s, 3H), 1.47(s, 3H) |
| 1-1-224 | 4-EtOBn | H | H | 4-ClPh | $^1$H NMR(500 MHz, CDCl$_3$) δ 7.68-7.66(m, 2H), 7.46-7.45(m, 2H), 7.25-7.23(m, 2H), 6.85(d, 2H J=8.5 Hz), 6.56(d, 1H, J=8.5 Hz), 6.41(dd, 1H, J=8.5 Hz, J=2.7 Hz), 6.36(d, 1H, J=9.8 Hz), 6.30(d, 1H, J=2.7 Hz), 5.61(d, 1H, J=9.8 Hz), 4.15(s, 2H), 4.03-3.99(m, 2H), 3.19(d, 1H, J=14.3 Hz), 3.15(d, 1H, J=14.3 Hz), 2.86(s, 3H), 1.19(s, 3H), 1.41-1.39(m, 3H) |
| 1-1-225 | 2-FBn | H | H | 4-ClPh | $^1$H NMR(500 MHz, CDCl$_3$) δ 7.68-7.67(m, 2H), 7.46-7.45(m, 2H), 7.35-7.32(m, 1H), 7.25-7.23(m, 1H), 7.08-7.07(m, 2H), 6.56(d, 1H, J=8.5 Hz), 6.42(dd, 1H, J=8.5 Hz, J=2.7 Hz), 6.35(d, 1H, J=9.8 Hz), 6.31(d, 1H, J=2.7 Hz), 5.61(d, 1H, J=9.8 Hz), 4.31(s, 2H), 3.19(d, 1H, J=14.3 Hz), 3.15(d, 1H, J=14.3 Hz), 2.85(s, 3H), 1.48(s, 3H) |
| 1-1-226 | 4-FBn | H | H | 4-ClPh | $^1$H NMR(500 MHz, CDCl$_3$) δ 7.68-7.67(m, 2H), 7.47-7.45(m, 2H), 7.39-7.29(m, 2H), 7.02-6.99(m, 2H), 6.56(d, 1H, J=8.5 Hz), 6.40-6.39(m, 1H), 6.35(d, 1H, J=9.8 Hz), 6.29(d, 1H, J=2.7 Hz), 5.62(d, 1H, J=9.8 Hz), 4.21(s, 2H), 3.17-3.16(m, 2H), 2.86(s, 3H), 1.49(s, 3H) |
| 1-1-227 | 3-FBn | H | H | 4-ClPh | $^1$H NMR(500 MHz, CDCl$_3$) δ 7.68(d, 2H, J=8.5 Hz), 7.46-7.28(m, 2H), 7.27-7.25(m, 1H), 7.12-7.10(m, 1H), 6.56(d, 1H, J=8.5 Hz), 6.38(dd, 1H, J=8.5 Hz, J=2.7 Hz), 6.34(d, 1H, J=9.8 Hz), 6.27(d, 1H, J=2.7 Hz), 5.62(d, 1H, J=9.8 Hz), 4.25(s, 2H), 3.19(d, 1H, J=14.3 Hz), 3.15(d, 1H, J=14.3 Hz), 2.86(s, 3H), 1.19(s, 3H) |
| 1-1-228 | i-Bu | H | H | 4-ClPh | $^1$H NMR(500 MHz, CDCl$_3$) δ 7.69-7.66(m, 2H), 7.47-7.44(m, 2H), 6.56(d, 1H, J=8.5 Hz), 6.40-6.36(m, 2H), 6.28(d, 1H, J=2.7 Hz), 5.62(d, 1H, J=9.8 Hz), 3.19(d, 1H, J=14.3 Hz), |

-continued

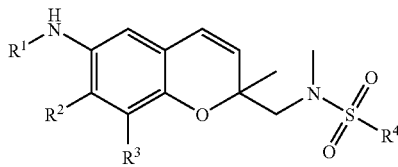

(1)

| Compd. No. | R₁ | R₂ | R₃ | R₄ | Analysis result (NMR/MS) |
|---|---|---|---|---|---|
| | | | | | 3.14(d, 1H, J=14.3 Hz), 2.86-2.84(m, 5H), 1.86-1.82(m, 1H), 1.49(s, 3H), 0.96-0.95(m, 6H) |
| 1-1-229 | 5-methylthiophen-2-ylmethyl | H | H | 4-ClPh | ¹H NMR(500 MHz, CDCl₃) δ 7.68-7.67(m, 2H), 7.47-7.45(m, 2H), 6.75(d, 1H, J=8.6 Hz), 6.58-6.56(m, 2H), 6.45-6.44(m, 1H), 6.36(d, 1H, J=9.8 Hz), 6.33(d, 1H, J=2.7 Hz), 5.63(d, 1H, J=9.8 Hz), 4.33(s, 2H), 3.19(d, 1H, J=14.3 Hz), 3.15(d, 1H, J=14.3 Hz), 2.86(s, 3H), 2.43(s, 3H), 1.49(s, 3H) |
| 1-1-230 | 2-NO₂Bn | H | H | 4-ClPh | ¹H NMR(500 MHz, CDCl₃) δ 8.03(d, 1H, J=1.0 Hz), 7.68-7.56(m, 2H), 7.56-7.54(m, 1H), 7.47-7.45(m, 2H), 6.54(d, 1H, J=8.5 Hz), 6.35-6.34(m, 1H), 6.32(d, 1H, J=9.8 Hz), 6.32(d, 1H, J=2.7 Hz), 5.61(d, 1H, J=9.8 Hz), 4.62(s, 2H), 3.17-3.16(m, 2H), 2.85(s, 3H), 1.47(s, 3H) |
| 1-1-231 | 4-NO₂Bn | H | H | 4-ClPh | ¹H NMR(500 MHz, CDCl₃) δ 8.18(d, 2H, J=8.6 Hz), 7.69-7.67(m, 2H), 7.51(d, 2H, J=8.4 Hz), 7.47-7.46(m, 2H), 6.55(d, 1H, J=8.5 Hz), 6.36-6.34(m, 1H), 6.33(d, 1H, J=9.8 Hz), 6.23(d, 1H, J=2.7 Hz), 5.63(d, 1H, J=9.8 Hz), 4.39(s, 2H), 3.95-3.80(br, 1H), 3.17(s, 2H), 2.86(s, 3H), 1.49(s, 3H) |
| 1-1-232 | 3-NO₂Bn | H | H | 4-ClPh | ¹H NMR(500 MHz, CDCl₃) δ 8.21(s, 1H), 8.10-8.09(m, 1H), 7.69-7.67(m, 2H), 7.49-7.45(m, 2H), 6.56(d, 1H, J=8.5 Hz), 6.38-6.35(m, 1H), 6.34(d, 1H, J=9.8 Hz), 6.25(d, 1H, J=2.7 Hz), 5.63(d, 1H, J=9.8 Hz), 4.38(s, 2H), 3.17(s, 2H), 2.85(s, 3H), 1.48(s, 3H) |
| 1-1-233 | PhEt | H | H | 4-ClPh | ¹H NMR(500 MHz, CDCl₃) δ 7.68(d, 2H, J=8.4 Hz), 7.47-7.45(m, 2H), 7.32-7.25(m, 2H), 7.25-7.19(m, 3H), 6.57(d, 1H, J=8.5 Hz), 6.42-6.41(m, 1H), 6.37(d, 1H, J=9.8 Hz), 6.30(d, 1H, J=2.7 Hz), 5.62(d, 1H, J=9.8 Hz), 3.34-3.31(m, 2H), 3.18-3.16(m, 2H), 2.90-2.86(m, 5H), 1.49(s, 3H) |
| 1-1-234 | n-Pr | H | H | 4-ClPh | ¹H NMR(500 MHz, CDCl₃) δ 7.69-7.67(m, 2H), 7.47-7.45(m, 2H), 6.57(d, 1H, J=8.5 Hz), 6.43(dd, 1H, J=8.5 Hz, J=2.7 Hz), 6.38(d, 1H, J=9.8 Hz), 6.33(d, 1H, J=2.7 Hz), 5.62(d, 1H, J=9.8 Hz), 3.21-3.16(m, 2H), 3.02-2.99(m, 2H), 2.86(s, 3H), 1.63-1.59(m, 2H), 1.49(s, 3H), 0.97(t, 3H, J=7.4 Hz) |
| 1-1-235 | pyridin-2-ylmethyl | H | H | 4-ClPh | ¹H NMR(500 MHz, CDCl₃) δ 8.57(d, 1H, J=4.7 Hz), 7.68-7.63(m, 3H), 7.46(d, 1H, J=8.5 Hz), 7.31(d, 1H, J=7.8 Hz), 7.18-7.17(m, 1H), 6.57(d, 1H, J=8.5 Hz), 6.45(dd, 1H, J=8.5 Hz, J=2.7 Hz), 6.36(d, 1H, J=9.8 Hz), 6.33(d, 1H, J=2.7 Hz), 5.61(d, 1H, J=9.8 Hz), 4.38(s, 2H), 3.19(d, 1H, J=14.3 Hz), 3.15(d, 1H, J=14.3 Hz), 2.88(s, 3H), 1.49(s, 3H) |
| 1-1-236 | pyridin-3-ylmethyl | H | H | 4-ClPh | ¹H NMR(500 MHz, CDCl₃) δ 8.60-8.59(m, 1H), 8.52-8.51(m, 1H), 7.69-7.67(m, 3H), 7.47-7.45(m, 2H), 7.27-7.26(m, 1H), 6.57(d, 1H, J=8.5 Hz), 6.40(dd, 1H, J=8.5 Hz, J=2.7 Hz), 6.35(d, 1H, J=9.8 Hz), 6.29(d, 1H, J=2.7 Hz), 5.63(d, 1H, J=9.8 Hz), 4.28(s, 2H), 3.17-3.16(m, 2H), 2.88(s, 3H), 1.49(s, 3H) |

-continued

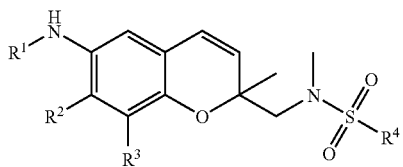

(1)

| Compd. No. | R₁ | R₂ | R₃ | R₄ | Analysis result (NMR/MS) |
|---|---|---|---|---|---|
| 1-1-237 | (4-pyridylmethyl) | H | H | 4-ClPh | ¹H NMR(500 MHz, CDCl₃) δ 8.54(d, 2H, J=8.5 Hz), 6.69-6.67(m, 2H), 6.47-6.45(m, 2H), 7.28-7.26(m, 2H), 6.55(d, 1H, J=8.5 Hz), 6.36-6.32(m, 2H), 6.32(d, 1H, J=2.7 Hz), 5.63(d, 1H, J=9.8 Hz), 4.30(s, 2H), 3.17(s, 2H), 2.88(s, 3H), 1.48(s, 3H) |
| 1-1-238 | (4-(diethoxymethyl)benzyl) | H | H | 4-ClPh | ¹H NMR(500 MHz, CDCl₃) δ 7.68(d, 2H J=8.5 Hz), 7.47-7.42(m, 4H), 7.34(d, 2H, J=8.0 Hz), 6.56(d, 1H, J=8.5 Hz), 6.41-6.40(m, 1H), 6.35(d, 1H, J=9.8 Hz), 6.30(d, 1H, J=2.7 Hz), 5.61(d, 1H, J=9.8 Hz), 5.47(s, 1H), 4.24(s, 2H), 3.63-3.60(m, 2H), 3.54-3.51(m, 2H), 3.17-3.16(m, 2H), 2.86(s, 3H), 1.49(s, 3H), 1.23(t, 6H, J=7.1 Hz) |
| 1-1-239 | (2-thienylmethyl) | H | H | 4-ClPh | ¹H NMR(500 MHz, CDCl₃) δ 7.70-7.67(m, 2H), 7.48-7.45(m, 2H), 7.19-7.18(m, 1H), 6.98-6.95(m, 2H), 6.58(d, 1H, J=8.5 Hz), 6.46-6.45(m, 1H), 6.37-6.34(m, 2H), 5.62(d, 1H, J=9.8 Hz), 4.43(s, 2H), 3.23-3.14(m, 2H), 2.87(s, 3H), 1.49(s, 3H) |
| 1-1-240 | (3-thienylmethyl) | H | H | 4-ClPh | ¹H NMR(500 MHz, CDCl₃) δ 7.69-7.67(m, 2H), 7.47-7.45(m, 2H), 7.30-7.29(m, 1H), 7.18(s, 1H), 7.06-7.05(m, 1H), 6.57(d, 1H, J=8.5 Hz), 6.44-6.43(m, 1H), 6.36(d, 1H, J=9.8 Hz), 6.32(d, 1H, J=2.7 Hz), 5.62(d, 1H, J=9.8 Hz), 4.25(s, 2H), 3.19(d, 1H, J=14.3 Hz), 3.16(d, 1H, J=14.3 Hz), 2.86(s, 3H), 1.49(s, 3H) |
| 1-1-241 | (4-acetoxybenzyl) | H | H | 4-ClPh | m/z 528 [M + H]⁺ |
| 1-1-242 | 4-ClBn | H | H | 4-ClPh | ¹H NMR(500 MHz, CDCl₃) δ 7.68-7.67(m, 2H), 7.47-7.45(m, 2H), 7.28-7.25(m, 4H), 6.56(d, 1H, J=8.5 Hz), 6.37(dd, 1H, J=8.5 Hz, J=2.7 Hz), 6.34(d, 1H, J=9.8 Hz), 6.27(d, 1H, J=2.7 Hz), 5.62(d, 1H, J=9.8 Hz), 4.22(s, 2H), 3.17-3.16(m, 2H), 2.85(s, 3H), 1.48(s, 3H) |
| 1-1-243 | 4-HOBn | H | H | 4-ClPh | ¹H NMR(500 MHz, CDCl₃) δ 7.68-7.66(m, 2H), 7.46-7.45(m, 2H), 7.19(d, 2H, J=8.1 Hz), 6.78(d, 2H, J=8.1 Hz), 6.56(d, 1H, J=8.5 Hz), 6.42-6.41(m, 1H), 6.35(d, 1H, J=9.8 Hz), 6.30(d, 1H, J=2.7 Hz), 5.61(d, 1H, J=9.8 Hz), 4.14(s, 2H), 3.19(d, 1H, J=14.5 Hz), 3.14(d, 1H, J=14.5 Hz), 2.86(s, 3H), 1.49(s, 3H) |
| 1-1-244 | 4-MeOBn | H | H | 4-FPh | ¹H NMR(500 MHz, CDCl₃) δ 7.77-7.46(m, 2H), 7.74-7.25(m, 2H), 7.18-7.15(m, 2H), 6.87-6.85(m, 2H), 6.57(d, 1H, J=8.5 Hz), 6.42-6.41(m, 1H), 6.36(d, 1H, J=9.8 Hz), 6.31(d, 1H, J=2.7 Hz), 5.62(d, 1H, J=9.8 Hz), 4.16(s, 2H), 3.19(d, 1H, J=14.3 Hz), 3.15(d, 1H, J=14.3 Hz), 2.86(s, 3H), 1.48(s, 3H) |
| 1-1-245 | 3-MeOBn | H | H | 4-FPh | ¹H NMR(500 MHz, CDCl₃) δ 7.77-7.74(m, 2H), 7.25-7.24(m, 1H), 7.18-7.14(m, 2H), |

-continued

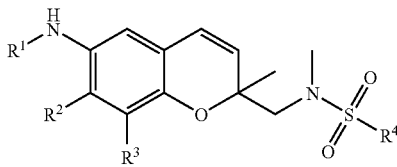

(1)

| Compd. No. | R₁ | R₂ | R₃ | R₄ | Analysis result (NMR/MS) |
|---|---|---|---|---|---|
| | | | | | 6.90-6.89(m, 2H), 6.75-6.74(m, 1H), 6.56(d, 1H, J=8.5 Hz), 6.42-6.41(m, 1H), 6.35(d, 1H, J=9.8 Hz), 6.30(d, 1H, J=2.7 Hz), 5.62(d, 1H, J=9.8 Hz), 4.21(s, 2H), 3.78(s, 3H), 3.19(d, 1H, J=14.3 Hz), 3.15(d, 1H, J=14.3 Hz), 2.85(s, 3H), 1.49(s, 3H) |
| 1-1-246 | 2-MeOBn | H | H | 4-FPh | ¹H NMR(500 MHz, CDCl₃) δ 7.77-7.74(m, 2H), 7.26-7.25(m, 2H), 6.89-6.86(m, 2H), 6.55(d, 1H, J=8.5 Hz), 6.44-6.43(m, 1H), 6.36(d, 1H, J=9.8 Hz), 6.33(d, 1H, J=2.7 Hz), 5.60(d, 1H, J=9.8 Hz), 4.24(s, 2H), 3.84(s, 3H), 3.23-3.12(m, 2H), 2.88(s, 3H), 1.49(s, 3H) |
| 1-1-247 | Bn | H | H | 4-FPh | ¹H NMR(500 MHz, CDCl₃) δ 7.77-7.75(m, 2H), 7.34-7.32(m, 4H), 7.26-7.25(m, 1H), 7.18-7.14(m, 2H), 6.56(d, 1H, J=8.5 Hz), 6.41(dd, 1H, J=8.5 Hz, J=2.7 Hz), 6.35(d, 1H, J=9.8 Hz), 6.30(d, 1H, J=2.7 Hz), 5.62(d, 1H, J=9.8 Hz), 4.21(s, 2H), 3.19(d, 1H, J=14.3 Hz), 3.15(d, 1H, J=14.3 Hz), 1.49(s, 3H) |
| 1-1-248 | 4-tert-BuBn | H | H | 4-FPh | ¹H NMR(500 MHz, CDCl₃) δ 7.77-7.74(m, 2H), 7.36(d, 2H, J=8.1 Hz), 7.28(d, 2H, J=8.1 Hz), 7.18-7.14(m, 2H), 6.57(d, 1H, J=8.5 Hz), 6.41-6.40(m, 1H), 6.37(d, 1H, J=9.8 Hz), 6.31(d, 1H, J=2.7 Hz), 5.62(d, 1H, J=9.8 Hz), 4.19(s, 2H), 3.18-3.16(m, 2H), 2.86(s, 3H), 1.50(s, 3H), 1.31(s, 9H) |
| 1-1-249 | 3-ClBn | H | H | 4-FPh | ¹H NMR(500 MHz, CDCl₃) δ 7.76-7.74(m, 2H), 7.33-7.32(m, 1H), 7.25-7.22(m, 3H), 7.18-7.14(m, 2H), 6.56(d, 1H, J=8.5 Hz), 6.35-6.33(m, 2H), 6.27(d, 1H, J=2.7 Hz), 5.63-5.61(m, 1H), 4.23(s, 2H), 3.19(d, 1H, J=14.3 Hz), 3.15(d, 1H, J=14.3 Hz), 2.85(s, 3H), 1.49(s, 3H) |
| 1-1-250 | 4-CNBn | H | H | 4-FPh | ¹H NMR(500 MHz, CDCl₃) δ 7.77-7.74(m, 2H), 7.61(d, 2H, J=8.0 Hz), 7.46(d, 2H, J=8.0 Hz), 7.19-7.15(m, 2H), 6.56(d, 1H, J=8.5 Hz), 6.34-6.32(m, 2H), 6.24(d, 1H, J=2.7 Hz), 5.64(d, 1H, J=8.5 Hz), 4.34(s, 2H), 3.18(s, 2H), 2.85(s, 3H), 1.48(s, 3H) |
| 1-1-251 | 4-EtOBn | H | H | 4-FPh | ¹H NMR(500 MHz, CDCl₃) δ 7.77-7.74(m, 2H), 7.25-7.23(m, 2H), 7.18-7.14(m, 2H), 6.85(d, 2H, J=8.6 Hz), 6.57(d, 2H, J=8.6 Hz), 6.42-6.40(m, 1H), 6.36(d, 1H, J=9.8 Hz), 6.31(d, 1H, J=2.7 Hz), 5.62(d, 1H, J=9.8 Hz), 4.15(s, 2H), 4.03-3.99(m, 2H), 3.19(d, 1H, J=14.3 Hz), 3.15(d, 1H, J=14.3 Hz), 2.85(s, 3H), 1.49(s, 3H), 1.41-1.39(m, 3H) |
| 1-1-252 | 2-FBn | H | H | 4-FPh | ¹H NMR(500 MHz, CDCl₃) δ 7.77-7.75(m, 2H), 7.35-7.34(m, 1H), 7.25-7.24(m, 1H), 7.18-7.15(m, 2H), 7.08-7.04(m, 2H), 6.57(d, 1H, J=8.5 Hz), 6.44-6.43(m, 1H), 6.36(d, 1H, J=9.8 Hz), 6.32(d, 1H, J=2.7 Hz), 5.62(d, 1H, J=9.8 Hz), 4.31(s, 2H), 3.19(d, 1H, J=14.3 Hz), 3.15(d, 1H, J=14.3 Hz), 2.85(s, 3H) |
| 1-1-253 | 4-FBn | H | H | 4-FPh | ¹H NMR(500 MHz, CDCl₃) δ 7.77-7.75(m, 2H), 7.32-7.29(m, 2H), 7.18-7.15(m, 2H), 7.02-6.99(m, 2H), 6.56(d, 1H, J=8.5 Hz), 6.41-6.40(m, 1H), 6.35(d, 1H, J=9.8 Hz), 6.29(d, 1H, J=2.7 Hz), 5.63(d, 1H, J=9.8 Hz), 4.21(s, 2H), 3.18-3.17(m, 2H), 2.85(s, 3H), 1.49(s, 3H) |
| 1-1-254 | 3-FBn | H | H | 4-FPh | ¹H NMR(500 MHz, CDCl₃) δ 7.77-7.74(m, 2H), 7.25-7.23(m, 1H), 7.16-7.12(m, 4H), 6.91-6.90(m, 1H), 6.56(d, 1H, J=8.5 Hz), |

-continued

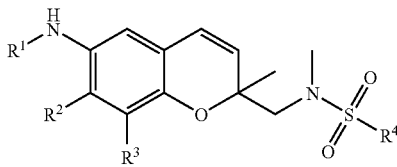

(1)

| Compd. No. | R₁ | R₂ | R₃ | R₄ | Analysis result (NMR/MS) |
|---|---|---|---|---|---|
| | | | | | 6.38(dd, 1H, J=8.5 Hz, J=2.7 Hz), 6.34(d, 1H, J=9.8 Hz), 6.28(d, 1H, J=2.7 Hz), 5.62(d, 1H, J=9.8 Hz), 4.25(s, 2H), 3.18-3.17(m, 2H), 2.85(s, 3H), 1.49(s, 3H) |
| 1-1-255 | i-Bu | H | H | 4-FPh | ¹H NMR(500 MHz, CDCl₃) δ 7.77-7.74(m, 2H), 7.18-7.15(m, 2H), 6.57(d, 1H, J=8.5 Hz), 6.40-6.37(m, 2H), 6.28(d, 1H, J=2.4 Hz), 5.62(d, 1H, J=9.8 Hz), 3.20(d, 1H, J=14.3 Hz), 3.15(d, 1H, J=14.3 Hz), 2.86-2.84(m, 5H), 1.85-1.82(m, 3H), 1.50(s, 3H), 0.96-0.95(m, 6H) |
| 1-1-256 | (5-methylthiophen-2-yl)methyl | H | H | 4-FPh | ¹H NMR(500 MHz, CDCl₃) δ 7.77-7.74(m, 2H), 7.18-7.15(m, 2H), 6.75-6.74(m, 1H), 6.58-6.57(m, 2H), 6.45-6.43(m, 1H), 6.37(d, 1H, J=9.8 Hz), 6.34(d, 1H, J=2.7 Hz), 5.63(d, 1H, J=9.8 Hz), 4.33(s, 2H), 3.20(d, 1H, J=14.3 Hz), 3.15(d, 1H, J=14.3 Hz), 2.85(s, 3H), 2.43(s, 3H), 1.50(s, 3H) |
| 1-1-257 | 2-NO₂Bn | H | H | 4-FPh | ¹H NMR(500 MHz, CDCl₃) δ 8.03-8.02(m, 1H), 7.77-7.74(m, 2H), 7.64-7.63(m, 1H), 7.53-7.52(m, 1H), 7.18-7.15(m, 2H), 6.54(d, 1H, J=8.5 Hz), 6.35-6.31(m, 2H), 6.23(d, 1H, J=2.7 Hz), 5.62(d, 1H, J=9.8 Hz), 4.62(s, 2H), 3.25-3.17(m, 2H), 2.85(s, 3H), 1.48(s, 3H) |
| 1-1-258 | 4-NO₂Bn | H | H | 4-FPh | ¹H NMR(500 MHz, CDCl₃) δ 8.18(d, 1H, J=8.5 Hz), 7.77-7.75(m, 2H), 7.52(d, 2H, J=8.4 Hz), 7.19-7.15(m, 2H), 6.56(d, 1H, J=8.5 Hz), 6.36-6.34(m, 1H), 6.33(d, 1H, J=9.8 Hz), 6.24(d, 1H, J=2.7 Hz), 5.64(d, 1H, J=9.8 Hz), 4.39(s, 2H), 3.18(s, 2H), 2.85(s, 3H), 1.48(s, 3H) |
| 1-1-259 | 3-NO₂Bn | H | H | 4-FPh | ¹H NMR(500 MHz, CDCl₃) δ 8.21(s, 1H), 8.10-8.09(m, 1H), 7.77-7.74(m, 2H), 7.68-7.67(m, 1H), 7.50(d, 1H, J=8.0 Hz), 7.18-7.15(m, 2H), 6.56(d, 1H, J=8.5 Hz), 6.38-6.37(m, 1H), 6.33(d, 1H, J=9.8 Hz), 6.26(d, 1H, J=2.7 Hz), 5.63(d, 1H, J=9.8 Hz), 4.38(s, 2H), 3.18(s, 2H), 2.85(s, 3H), 1.48(s, 3H) |
| 1-1-260 | PhEt | H | H | 4-FPh | ¹H NMR(500 MHz, CDCl₃) δ 7.77-7.74(m, 2H), 7.30-7.14(m, 7H), 6.57(d, 1H, J=8.5 Hz), 6.38-6.36(m, 2H), 6.29(d, 1H, J=2.7 Hz), 5.63(d, 1H, J=9.8 Hz), 3.33-3.30(m, 2H), 3.21-3.13(m, 2H), 2.90-2.83(m, 5H), 1.50(s, 3H) |
| 1-1-261 | n-Pr | H | H | 4-FPr | ¹H NMR(500 MHz, CDCl₃) δ 7.77-7.74(m, 2H), 7.18-7.15(m, 2H), 6.57(d, 1H, J=8.5 Hz), 6.41(dd, 1H, J=8.5 Hz, J=2.7 Hz), 6.38(d, 1H, J=9.8 Hz), 6.30(d, 1H, J=2.7 Hz), 5.63(d, 1H, J=9.8 Hz), 3.20(d, 1H, J=14.3 Hz), 3.15(d, 1H, J=14.3 Hz), 3.01-2.99(m, 2H), 2.86(s, 3H), 1.63-1.58(m, 2H), 1.50(s, 3H), 0.97(t 3, J=7.4 Hz) |
| 1-1-262 | (pyridin-2-yl)methyl | H | H | 4-FPh | ¹H NMR(500 MHz, CDCl₃) δ 8.57-5.56(m, 1H), 7.77-7.74(m, 2H), 7.67-7.66(m, 1H), 7.31(d, 1H, J=7.8 Hz), 7.18-7.14(m, 3H), 6.57(d, 1H, J=8.5 Hz), 6.46-6.45(m, 1H), 6.36(d, 1H, J=9.8 Hz), 6.34(d, 1H, J=2.7 Hz), 5.62(d, 1H, J=9.8 Hz), 4.37(s, 2H), 3.21-3.17(m, 2H), 2.87(s, 3H), 1.49(s, 3H) |

-continued

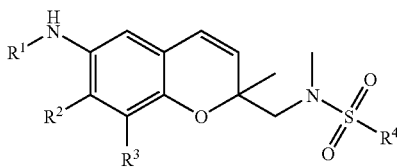

(1)

| Compd. No. | R₁ | R₂ | R₃ | R₄ | Analysis result (NMR/MS) |
|---|---|---|---|---|---|
| 1-1-263 | (pyridin-3-yl)methyl | H | H | 4-FPh | ¹H NMR(500 MHz, CDCl₃) δ 8.60-8.59(m, 1H), 8.52-8.51(m, 1H), 7.77-7.75(m, 2H), 7.69-7.68(m, 1H), 7.27-7.25(m, 1H), 7.18-7.15(m, 2H), 6.57(d, 1H, J=8.5 Hz), 7.40(dd, 1H, J=8.5 Hz, J=2.7 Hz), 6.35(d, 1H, J=9.8 Hz), 6.29(d, 1H, J=2.7 Hz), 5.63(d, 1H, J=9.8 Hz), 4.28(s, 2H), 3.18-3.17(m, 2H), 2.88(s, 3H), 1.49(s, 3H) |
| 1-1-264 | (pyridin-4-yl)methyl | H | H | 4-FPh | ¹H NMR(500 MHz, CDCl₃) δ 8.54(d, 2H, J=5.9 Hz), 7.77-7.75(m, 2H), 7.28-7.26(m, 2H), 7.18-7.15(m, 2H), 6.56(d, 1H, J=8.5 Hz), 6.36-6.35(m, 2H), 6.33(d, 1H, J=9.8 Hz), 6.24(d, 1H, J=2.7 Hz), 5.63(d, 1H, J=9.8 Hz), 4.30(s, 2H), 3.18(s, 2H), 2.88(s, 3H), 1.48(s, 3H) |
| 1-1-265 | 4-(diethoxymethyl)benzyl | H | H | 4-FPh | ¹H NMR(500 MHz, CDCl₃) δ 7.77-7.74(m, 2H), 7.43(d, 2H, J=8.0 Hz), 7.33(d, 2H, J=8.0 Hz), 7.18-7.15(m, 2H), 6.56(d, 1H, J=8.5 Hz), 6.36-3.29(m, 3H), 5.62(d, 1H, J=9.8 Hz), 5.47(s, 1H), 4.24(s, 2H), 3.61-3.60(m, 2H), 3.54-3.53(m, 2H), 3.18-3.16(m, 2H), 2.86(s, 3H), 1.49(s, 3H), 1.25-1.21(m, 6H) |
| 1-1-266 | (thiophen-2-yl)methyl | H | H | 4-FPh | m/z 459 [M + H]⁺ |
| 1-1-267 | (thiophen-3-yl)methyl | H | H | 4-FPh | ¹H NMR(500 MHz, CDCl₃) δ 7.77-7.75(m, 2H), 7.29-7.27(m, 1H), 7.18-7.15(m, 3H), 7.06-7.05(m, 1H), 6.58(d, 1H, J=8.5 Hz), 6.44-6.43(m, 1H), 6.37(d, 1H, J=9.8 Hz), 6.33(d, 1H, J=2.7 Hz), 5.63(d, 1H, J=9.8 Hz), 4.25(s, 2H), 3.20(d, 1H, J=14.3 Hz), 3.16(d, 1H, J=14.3 Hz), 2.86(s, 3H), 1.50(s, 3H) |
| 1-1-268 | 4-acetoxybenzyl | H | H | 4-FPh | ¹H NMR(500 MHz, CDCl₃) δ 7.77-7.74(m, 2H), 7.35(d, 1H, J=8.5 Hz), 7.18-7.14(m, 2H), 7.05-7.03(m, 2H), 6.57(d, 1H, J=8.5 Hz), 6.41-6.40(m, 1H), 6.35(d, 1H, J=9.8 Hz), 6.29(d, 1H, J=2.7 Hz), 5.62(d, 1H, J=9.8 Hz), 4.23(s, 2H), 3.20(d, 1H, J=14.3 Hz), 3.15(d, 1H J=14.3 Hz), 2.86(s, 3H), 2.29(s, 3H), 1.50(s, 3H) |
| 1-1-269 | 4-ClBn | H | H | 4-FPh | ¹H NMR(500 MHz, CDCl₃) δ 7.77-7.74(m, 2H), 7.28-7.25(m, 4H), 7.18-7.15(m, 2H), 6.56(d, 1H, J=8.5 Hz), 6.38(dd, 1H, J=8.5 Hz, J=2.7 Hz), 6.34(d, 1H, J=9.8 Hz), 6.27(d, 1H, J=2.7 Hz), 5.63(d, 1H, J=9.8 Hz), 42.(s, 2H), 3.19(d, 1H, J=14.3 Hz), 3.16(d, 1H, J=14.3 Hz), 2.85(s, 3H), 1.49(s, 3H) |
| 1-1-270 | 4-HOBn | H | H | 4-FPh | ¹H NMR(500 MHz, CDCl₃) δ 7.77-7.74(m, 2H), 7.21-7.15(m, 4H), 6.79(d, 2H, J=8.4 Hz), 6.57(d, 1H, J=8.5 Hz), 6.43-6.42(m, 1H), 6.36(d, 1H, J=9.8 Hz), 6.31(d, 1H, J=2.7 Hz), 5.62(d, 1H, J=9.8 Hz), 4.15(s, 2H), 3.19(d, 1H, J=14.3 Hz), 3.16(d, 1H, J=14.3 Hz), 2.86(s, 3H), 1.48(s, 3H) |

-continued

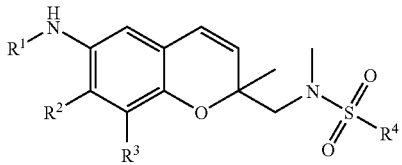

(1)

| Compd. No. | R₁ | R₂ | R₃ | R₄ | Analysis result (NMR/MS) |
|---|---|---|---|---|---|
| 1-1-271 | 4-MeOBn | H | H | Me | ¹H NMR(500 MHz, CDCl₃) δ 7.28(d, 2H, J=8.5 Hz), 6.87(d, 2H, J=8.5 Hz), 6.61(d, 1H, J=8.5 Hz), 6.45(dd, 1H, J=8.5 Hz, J=2.7 Hz), 6.36(d, 1H, J=9.8 Hz), 6.34(d, 1H, J=2.7 Hz), 5.60(d, 1H, J=9.8 Hz), 4.43(s, 2H), 3.80(s, 3H), 3.33(d, 1H, J=14.5 Hz), 3.26(d, 1H, J=14.5 Hz), 2.99(s, 3H), 2.77(s, 3H), 1.44(s, 3H) |
| 1-1-272 | 3-MeOBn | H | H | Me | ¹H NMR(500 MHz, CDCl₃) δ 7.27 7.24(m, 2H), 6.95 6.92(m, 2H), 6.81(d, 1H, J=8.2 Hz), 6.61(d, 1H, J=8.6 Hz), 6.45(dd, 1H, J=8.6 Hz, J=2.8 Hz), 6.36(d, 1H, J=9.8 Hz), 6.33(d, 1H, J=2.8 Hz), 5.58(d, 1H, J=9.8 Hz), 4.24(s, 2H), 3.33(d, 1H, J=14.5 Hz), 3.25(d, 1H, J=14.5 Hz), 2.98(s, 3H), 2.77(s, 3H), 1.43(s, 3H) |
| 1-1-273 | 2-MeOBn | H | H | Me | ¹H NMR(500 MHz, CDCl₃) δ 7.30 7.25(m, 2H), 6.92 6.88(m, 2H), 6.60(d, 1H, J=8.5 Hz), 6.47(dd, 1H, J=8.5 Hz, J=2.7 Hz), 6.37(m, 1H), 6.36(d, 1H, J=9.9 Hz), 5.58(d, 1H, J=9.9 Hz), 4.24(s, 2H), 3.86(s, 3H), 3.32(d, 1H, J=14.5 Hz), 3.24(d, 1H, J=14.5 Hz), 2.98(s, 3H), 2.76(s, 3H), 1.43(s, 3H) |
| 1-1-274 | Bn | H | H | Me | ¹H NMR(500 MHz, CDCl₃) δ 7.37 7.27(m, 5H), 6.61(d, 1H, J=8.5 Hz), 6.45(dd, 1H, J=8.5 Hz, J=2.7 Hz), 6.36(d, 1H, J=9.8 Hz), 6.34(d, 1H, J=2.7 Hz), 5.60(d, 1H, J=9.8 Hz), 3.34(d, 1H, J=14.5 Hz), 3.24(d, 1H, J=14.5 Hz), 2.98(s, 3H), 2.77(s, 3H), 1.43(s, 3H) |
| 1-1-275 | 4-tert-BuBn | H | H | Me | ¹H NMR(500 MHz, CDCl₃) δ 7.37(d, 2H, J=8.2 Hz), 7.30(d, 2H, J=8.2 Hz), 6.62(d, 1H, J=8.5 Hz), 6.47(dd, 1H, J=8.5 Hz, J=2.7 Hz), 6.37(d, 1H, J=9.8 Hz), 6.34(d, 1H, J=2.7 Hz), 5.60(d, 1H, J=9.8 Hz), 4.24(s, 2H), 3.33(d, 1H, J=14.5 Hz), 3.26(d, 1H, J=14.5 Hz), 3.02(s, 3H), 2.79(s, 3H), 1.44(s, 3H), 1.32(s, 9H) |
| 1-1-276 | 3-ClBn | H | H | Me | m/z 407 [M + H]⁺ |
| 1-1-277 | 4-CNBn | H | H | Me | ¹H NMR(500 MHz, CDCl₃) δ 7.62(d, 2H, J=7.9 Hz), 7.47(d, 2H, J=7.9 Hz), 6.60(d, 1H, J=8.5 Hz), 6.38(dd, 1H, J=2.2 Hz, J=8.5 Hz), 6.33(d, 1H, 9.8 Hz), 6.27(s, 1H), 5.61(d, 1H, J=9.8 Hz), 4.36(s, 2H), 3.34(d, 1H, J=14.5 Hz), 3.27(d, 1H, J=14.5 Hz), 2.98(s, 3H), 2.78(s, 3H), 1.42(s, 3H) |
| 1-1-278 | 4-EtOBn | H | H | Me | ¹H NMR(500 MHz, CDCl₃) δ 7.27(d, 2H, J=8.6 Hz), 6.86(d, 2H, J=8.6 Hz), 6.61(d, 1H, J=8.6 Hz), 6.45(dd, 1H, J=8.6 Hz, J=2.8 Hz), 6.36(d, 1H, J=9.8 Hz), 6.33(d, 1H, J=2.8 Hz), 5.60(d, 1H, J=9.8 Hz), 4.18(d, 2H), 4.04 4.00(q, 2H), 3.33(d, 1H, J=14.1 Hz), 3.25(d, 1H, J=14.1 Hz), 2.99(s, 3H), 2.77(s, 3H), 1.48 1.40(m, 6H) |
| 1-1-279 | 2-FBn | H | H | Me | ¹H NMR(500 MHz, CDCl₃) δ 7.37 7.27(m, 1H), 7.23 7.10(m, 3H), 6.61(d, 1H, J=8.5 Hz), 6.48(dd, 1H, J=8.5 Hz, J=2.6 Hz), 6.36(d, 1H, J=9.8 Hz), 6.34(s, 1H), 5.60(d, 1H, J=9.8 Hz), 4.33(s, 2H), 3.34(d, 1H, J=14.5 Hz), 3.28(d, 1H, J=14.5 Hz), 2.98(s, 3H), 2.77(s, 3H), 1.43(s, 3H) |
| 1-1-280 | 4-FBn | H | H | Me | ¹H NMR(500 MHz, CDCl₃) δ 7.34 7.31(m, 2H), 7.04 7.00(m, 2H), 6.61(d, 1H, J=8.5 Hz), 6.45(dd, 1H, J=8.5 Hz, J=2.4 Hz), 6.35(d, 1H, J=9.8 Hz), .32(d, 1H, J=2.4 Hz), 5.60(d, 1H, J=9.8 Hz), 4.23(s, 2H), 3.33(d, 1H, J=14.5 Hz), 3.24(d, 1H, J=14.5 Hz), 2.99(s, 3H), 2.80(s, 3H), 1.43(s, 3H) |
| 1-1-281 | 3-FBn | H | H | Me | ¹H NMR(500 MHz, CDCl₃) δ 7.24(m, 1H), 7.14 7.12(m, 1H), 6.62 6.59(m, 1H), 6.43 6.42(m, 1H), 6.36 6.35(m, 1H), 6.33(d, 1H, J=9.8 Hz), 6.30(d, 1H, J=2.7 Hz), 5.60(d, 1H, J=9.8 Hz), 4.27(s, 2H), 3.32(d, 1H, J=14.5 Hz), 3.26(d, 1H, J=14.5 Hz), 2.98(s, 3H), 2.77(s, 3H), 1.43(s, 3H) |

-continued

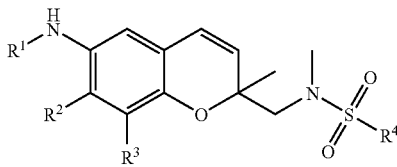

(1)

| Compd. No. | R₁ | R₂ | R₃ | R₄ | Analysis result (NMR/MS) |
|---|---|---|---|---|---|
| 1-1-282 | i-Bu | H | H | Me | $^1$H NMR(500 MHz, CDCl$_3$) δ 6.61(d, 1H, J=8.5 Hz), 6.43(dd, 1H, J=8.5 Hz, J=2.8 Hz), 6.38(dd, 1H, J=9.8 Hz, J=6.7 Hz), 6.31(d, 1H, J=2.8 Hz), 5.60(dd, 1H, J=9.8 Hz, J=6.7 Hz), 3.32(d, 1H, J=15 Hz), 3.26(d, 1H, J=15 Hz), 2.99(s, 3H), 2.87(d, 2H, J=6.7 Hz), 2.77(s, 3H), 1.89 1.84(m, 1H), 0.98(s, 6H) |
| 1-1-283 | 5-methylthiophen-2-ylmethyl | H | H | Me | m/z 393 [M + H]⁺ |
| 1-1-284 | 2-NO₂Bn | H | H | Me | m/z 418 [M + H]⁺ |
| 1-1-285 | 4-NO₂Bn | H | H | Me | $^1$H NMR(500 MHz, CDCl$_3$) δ 8.18(d, 2H, J=8.5 Hz), 7.51(d, 2H, J=8.5 Hz), 6.60(d, 1H, J=8.5 Hz), 6.39(dd, 1H, J=8.5 Hz, J=2.8 Hz), 6.33(d, 1H, J=9.9 Hz), 6.26(dd, 1H, J=8.5 Hz, J=2.8 Hz), 5.61(d, 1H, J=9.9 Hz), 4.41(s, 2H), 3.34(d, 1H, J=14.5 Hz), 3.25(d, 1H, J=14.5 Hz), 2.78(s, 3H), .98(s, 3H), 1.42(s, 3H) |
| 1-1-286 | 3-NO₂Bn | H | H | Me | $^1$H NMR(500 MHz, CDCl$_3$) δ 8.23 8.21(m, 1H), 7.65(m, 1H), 7.51(m, 1H), 7.01 7.00(m, 1H), 6.61(d, 1H, J=8.5 Hz), 6.42(m, 1H), 6.34(d, 1H, J=9.9 Hz), 6.29(d, 1H, J=2.8 Hz), 5.61(d, 1H, J=9.9 Hz), 4.40(s, 2H), 3.31(d, 1H, J=14.3 Hz), 3.25(d, 1H, J=14.3 Hz), 2.98(s, 3H), 2.77(s, 3H), 1.43(s, 3H) |
| 1-1-287 | PhEt | H | H | Me | $^1$H NMR(500 MHz, CDCl$_3$) δ 7.33 7.21(m, 5H), 6.62(d, 1H, J=8.5 Hz), 6.45(dd, 1H, J=8.5 Hz, J=2.8 Hz), 6.37(d, 1H, J=9.9 Hz), 6.33(d, 1H, J=2.8 Hz), 5.61(d, 1H, J=9.9 Hz), 3.37 3.32(m, 2H), 3.27 3.25(m, 1H), 2.99(s, 3H), 2.94 2.90(m, 2H), 2.78(s, 3H), 1.44(s, 3H) |
| 1-1-288 | n-Pr | H | H | Me | $^1$H NMR(500 MHz, CDCl$_3$) δ 6.62(d, 1H, J=8.5 Hz), 6.45(d, 1H, J=8.5 Hz), 6.38(d, 1H, J=9.8 Hz), 6.33(s, 1H), 5.61(dd, 1H, J=9.8 Hz, J=1.0 Hz), 3.34(d, 1H, J=14.6 Hz), 3.26(d, 1H, J=14.6 Hz), 3.04 3.01(m, 2H), 2.99(s, 3H), 2.78(s, 3H), 1.65 1.61(m, 2H), 1.44(s, 3H), 1.00 0.97(m, 3H) |
| 1-1-289 | pyridin-2-ylmethyl | H | H | Me | $^1$H NMR(500 MHz, CDCl$_3$) δ 8.60(d, 1H, J=4.2 Hz), 7.70(d, 1H, J=7.6 Hz), 7.38(d, 1H, J=7.6 Hz), 7.25-7.22(m, 1H), 6.61(d, 1H, J=8.5 Hz), 6.48(dd, 1H, J=8.5 Hz, J=2.6 Hz), 6.37(d, 1H, J=9.8 Hz), 6.36(m, 1H), 5.60(d, 1H, J=9.8 Hz), 4.44(s, 2H), 3.34(d, 1H, J=14.5 Hz), 3.28(d, 1H, J=14.5 Hz), 2.98(s, 3H), 2.77(s, 3H), 1.43(s, 3H) |
| 1-1-290 | pyridin-3-ylmethyl | H | H | Me | $^1$H NMR(500 MHz, CDCl$_3$) δ 8.66(s, 1H), 8.56(d, 1H, J=4.8 Hz), 7.82(d, 1H, J=7.8 Hz), 7.38(dd, 1H, J=7.8 Hz, J=4.8 Hz), 6.62(d, 1H, J=8.5 Hz), 6.42(dd, 1H, J=8.5 Hz, J=2.6 Hz), 6.35(d, 1H, J=9.9 Hz), 6.31-6.30(m, 1H), 5.61(d, 1H, J=9.9 Hz) 4.35(s, 2H), 3.34(d, 1H, J=14.5 Hz), 3.26(d, 1H, J=14.5 Hz), 2.99(s, 3H), 2.78(s, 3H) |
| 1-1-291 | pyridin-4-ylmethyl | H | H | Me | m/z 374 [M + H]⁺ |

-continued

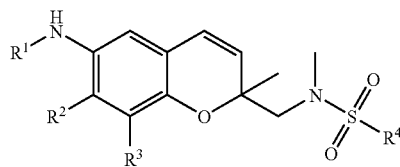

(1)

| Compd. No. | R₁ | R₂ | R₃ | R₄ | Analysis result (NMR/MS) |
|---|---|---|---|---|---|
| 1-1-292 | | H | H | Me | m/z 475 [M + H]⁺ |
| 1-1-293 | | H | H | Me | ¹H NMR(500 MHz, CDCl₃) δ 7.47(m, 1H), 7.00 6.96(m, 1H), 6.62(d, 1H, J=8.5 Hz), 6.49(dd, 1H, J=8.5 Hz, J=2.4 Hz), 6.38(d, 1H, J=9.8 Hz), 6.37(d, 1H, J=2.4 Hz), 5.60(d, 1H, J=9.8 Hz), 4.45(s, 2H), 3.37(d, 1H, J=14.5 Hz), 3.31(d, 1H, J=14.5 Hz), 2.98(s, 3H), 2.77(s, 3H), 1.43(s, 3H) |
| 1-1-294 | | H | H | Me | m/z 479 [M + H]⁺ |
| 1-1-295 | | H | H | Me | ¹H NMR(500 MHz, CDCl₃) δ 7.37(d, 2H, J=8.3 Hz), 7.05(d, 2H, J=8.3 Hz), 6.61(d, 1H, J=8.5 Hz), 6.44(dd, 1H, J=8.5 Hz, J=2.6 Hz), 6.36(d, 1H, J=9.8 Hz), 6.32(d, 1H, J=2.6 Hz), 5.60(d, 1H, J=9.8 Hz), 4.25(s, 2H), 3.33(d, 1H, J=14.7 Hz), 3.27(d, 1H, J=14.7 Hz), 2.99(s, 3H), 2.77(s, 3H), 2.30(s, 3H), 1.43(s, 3H) |
| 1-1-296 | 4-ClBn | H | H | Me | ¹H NMR(500 MHz, CDCl₃) δ 7.28(d, 4H, J=7.6 Hz), 7.16(d, 4H, J=7.6 Hz), 6.60(d, 1H, J=8.6 Hz), 6.50(d, 1H, J=8.6 Hz), 6.38(s, 1H), 6.30(d, 1H, J=9.9 Hz), 5.59(dd, 1H, J=9.9 Hz, J=1.3 Hz), 4.45(s, 4H), 3.36(d, 1H, J=14.5 Hz), 3.24(d, 1H, J=14.5 Hz), 2.99(s, 3H), 2.78(s, 3H), 1.42(s, 3H) |
| 1-1-297 | 4-HOBn | H | H | Me | ¹H NMR(500 MHz, CDCl₃) δ 7.31 7.27(m, 4H), 6.61(d, 1H, J=8.5 Hz), 6.42(dd, 1H, J=8.5 Hz, J=2.4 Hz), 6.35(d, 1H, J=9.9 Hz), 6.30(d, 1H, J=2.4 Hz), 5.60(d, 1H, J=9.9 Hz), 3.34(d, 1H, J=14.5 Hz), 3.25(d, 1H, J=14.5 Hz), 2.98(s, 3H), 2.77(s, 3H), 1.43(s, 3H) |
| 1-1-298 | 4-MeOBn | H | H | n-Pr | ¹H NMR(500 MHz, CDCl₃) δ 7.29-7.25(m, 3H), 6.87(d, 2H, J=6.7 Hz), 6.61(d, 1H, J=8.5 Hz), 6.45(dd, 1H, J=8.5 Hz, J=2.8 Hz), 6.36(d, 1H, J=9.8 Hz), 6.34(d, 1H, J=9.8 Hz), 6.34(d, 1H, J=2.8 Hz), 5.60(d, 1H, J=9.8 Hz), 4.19(s, 2H), 3.80(s, 3H), 3.37(d, 1H, J=14.6 Hz), 3.30(d, 1H, J=14.6 Hz), 3.00(s, 3H), 2.92-2.88(m, 2H), 1.81-1.76(m, 2H), 1.43(s, 3H), 1.01(t, 3H, J=7.4 Hz) |
| 1-1-299 | 3-MeOBn | H | H | n-Pr | ¹H NMR(500 MHz, CDCl₃) δ 7.27-7.24(m, 2H), 6.95-6.92(m, 2H), 6.82-6.81(m, 1H), 6.61(d, 1H, J=8.5 Hz), 6.45(dd, 1H, J=8.5 Hz, J=2.8 Hz), 6.35(d, 1H, J=9.8 Hz), 6.33(d, 1H, J=2.7 Hz), 5.59(d, 1H, J=9.8 Hz), 4.24(s, 2H), 3.80(s, 3H), 3.37(d, 1H, J=14.6 Hz), 3.30(d, 1H, J=14.6 Hz), 3.00(s, 3H), 2.92-2.88(m, 2H), 1.80-1.77(m, 2H), 1.43(s, 3H), 1.01(t, 3H, J=7.4 Hz) |
| 1-1-300 | 2-MeOBn | H | H | n-Pr | ¹H NMR(500 MHz, CDCl₃) δ 7.30-7.24(m, 3H), 6.92-6.88(m, 2H), 6.61(d, 1H, J=8.6 Hz), 6.48-6.46(m, 1H), 6.37(d, 1H, J=9.8 Hz), 5.58(d, |

-continued

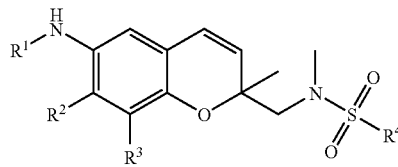

(1)

| Compd. No. | R₁ | R₂ | R₃ | R₄ | Analysis result (NMR/MS) |
|---|---|---|---|---|---|
| | | | | | 1H, J=9.8 Hz), 4.26(s, 2H), 3.85(s, 3H), 3.35(d, 1H, J=14.6 Hz), 3.29(d, 1H, J=14.6 Hz), 2.99(s, 3H), 2.91-2.88(m, 2H), 1.80-1.77(m, 2H), 1.43(s, 3H), 1.01(t, 3H, J=7.5 Hz) |
| 1-1-301 | Bn | H | H | n-Pr | $^1$H NMR(500 MHz, CDCl$_3$) δ 7.37-7.32(m, 4H), 7.26-7.25(m, 1H), 6.61(d, 1H, J=8.5 Hz), 6.45(dd, 1H, J=8.5 Hz, J=2.8 Hz), 6.37-6.33(m, 2H), 5.60(d, 1H, J=9.8 Hz), 4.26(s, 2H), 3.37(d, 1H, J=14.6 Hz), 3.30(d, 1H, J=14.6 Hz), 3.00(s, 3H), 2.92-2.88(m, 2H), 1.80-1.76(m, 2H), 1.43(s, 3H), 1.01(t, 3H, J=7.4 Hz) |
| 1-1-302 | 4-tert-BuBn | H | H | n-Pr | $^1$H NMR(500 MHz, CDCl$_3$) δ 7.37(d, 2H, J=8.3 Hz), 7.30(d, 2H, J=8.3 Hz), 6.61(d, 1H, J=8.5 Hz), 6.45(dd, 1H, J=8.5 Hz, J=2.8 Hz), 6.38-6.34(m, 2H), 5.60(d, 1H, J=9.8 Hz), 4.22(s, 2H), 3.37(d, 1H, J=14.6 Hz), 3.30(d, 1H, J=14.6 Hz), 3.00(s, 3H), 2.92-2.88(m, 2H), 1.80-1.78(m, 2H), 1.43(s, 3H), 1.32(s, 9H), 1.01(t, 3H, J=7.4 Hz) |
| 1-1-303 | 3-ClBn | H | H | n-Pr | $^1$H NMR(500 MHz, CDCl$_3$) δ 7.36(s, 1H), 7.26-7.23(m, 3H), 6.60(d, 1H, J=8.6 Hz), 6.42(dd, 1H, J=8.5 Hz, J=2.7 Hz), 6.35(d, 1H, J=9.8 Hz), 6.30(d, 1H, J=2.7 Hz), 5.60(d, 1H, J=9.8 Hz), 4.26(s, 2H), 3.37(d, 1H, J=14.6 Hz), 3.30(d, 1H, J=14.6 Hz), 3.00(s, 3H), 2.92-2.88(m, 2H), 1.81-1.77(m, 2H), 1.43(s, 3H), 1.01(t, 3H, J=7.5 Hz) |
| 1-1-304 | 4-CNBn | H | H | n-Pr | $^1$H NMR(500 MHz, CDCl$_3$) δ 7.62(d, 2H, J=8.1 Hz), 7.47(d, 2H, J=8.1 Hz), 6.59(d, 1H, J=8.5 Hz), 6.38(dd, 1H, J=8.5 Hz, J=2.8 Hz), 6.34(d, 1H, J=9.9 Hz), 6.26(d, 1H, J=2.8 Hz), 5.61(d, 1H, J=9.9 Hz), 4.36(s, 2H), 3.38(d, 1H, J=14.6 Hz), 3.29(d, 1H, J=14.6 Hz), 2.99(s, 3H), 2.92-2.88(m, 2H), 1.81-1.76(m, 2H), 1.81-1.76(m, 2H), 1.42(s, 3H), 1.01(t, 3H, J=7.4 Hz) |
| 1-1-305 | 4-EtOBn | H | H | n-Pr | $^1$H NMR(500 MHz, CDCl$_3$) δ 7.27-7.25(m, 2H), 6.87-6.857.26-7.25(m, 1H), 6.61(d, 1H, J=8.5 Hz), 6.45(dd, 1H, J=8.5 Hz, J=2.8 Hz), 6.37-6.33(m, 2H), 5.60(d, 1H, J=9.8 Hz), 4.26(s, 2H), 3.37(d, 1H, J=14.6 Hz), 3.30(d, 1H, J=14.6 Hz), 3.00(s, 3H), 2.92-2.88(m, 2H), 1.80-1.76(m, 2H), 1.43(s, 3H), 1.01(t, 3H, J=7.4 Hz) |
| 1-1-306 | 2-FBn | H | H | n-Pr | $^1$NMR(500 MHz, CDCl$_3$) δ 7.37(m, 1H), 7.26(m, 1H), 7.12-7.05(m, 2H), 6.61(d, 1H, J=8.5 Hz), 6.45(dd, 1H, J=8.5 Hz, J=2.7 Hz), 6.37-6.34(m, 2H), 5.60(d, 1H, J=9.8 Hz), 4.33(s, 2H), 3.37(d, 1H, J=14.6 Hz), 2.29(s, 3H), 2.92-2.88(m, 2H), 1.80-1.77(m, 2H), 1.43(s, 3H), 1.01(t, 3H, J=7.5 Hz) |
| 1-1-307 | 4-FBn | H | H | n-Pr | $^1$H NMR(500 MHz, CDCl$_3$) δ 7.34-7.30(m, 2H), 7.04-7.01(m, 2H), 6.61(d, 1H, J=8.6 Hz), 6.43(dd, 1H, J=8.5 Hz, J=2.8 Hz), 6.35(d, 1H, J=9.9 Hz), 6.31(d, 1H, J=2.8 Hz), 5.60(d, 1H, J=9.9 Hz), 3.37(d, 1H, J=14.6 Hz), 3.30(d, 1H, J=14.6 Hz), 2.99(s, 3H), 2.92-2.88(m, 2H), 1.80-1.77(m, 2H), 1.01(t, 3H, J=7.5 Hz) |
| 1-1-308 | 3-FBn | H | H | n-Pr | $^1$H NMR(500 MHz, CDCl$_3$) δ 7.30-7.24(m, 1H), 7.13(d, 1H, J=7.7 Hz), 7.08(d, 1H, J=9.7 Hz), 6.96-6.94(m, 1H), 6.60(d, 1H, J=8.5 Hz), 6.42(dd, 1H, J=8.6 Hz, J=2.8 Hz), 6.35(d, 1H, J=9.9 Hz), 6.30(d, 1H, J=2.8 Hz), 5.60(d, 1H, J=9.8 Hz), 3.37(d, 1H, J=14.6 Hz), 3.30(d, 1H, J=14.6 Hz), 2.99(s, 3H), 2.92-2.88(m, 2H), 1.80-1.77(m, 2H), 1.01(t, 3H, J=7.4 Hz) |

-continued

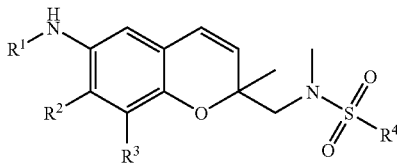

(1)

| Compd. No. | R₁ | R₂ | R₃ | R₄ | Analysis result (NMR/MS) |
|---|---|---|---|---|---|
| 1-1-309 | i-Bu | H | H | n-Pr | $^1$H NMR(500 MHz, CDCl$_3$) δ 6.61(d, 1H, J=8.5 Hz), 6.43(dd, 1H, J=8.9 Hz, J=2.8 Hz), 6.38(d, 1H, J=9.9 Hz), 6.31(d, 1H, J=2.8 Hz), 5.60(d, 1H, J=9.9 Hz), 3.37(d, 1H, J=14.6 Hz), 3.30(d, 1H, J=14.6 Hz), 2.99(s, 3H), 2.92-2.86(m, 4H), 1.86-1.78(m, 3H), 1.03-0.96(m, 9H) |
| 1-1-400 | (5-methylthien-2-yl)CH₂C(CH₃)₂– | H | H | n-Pr | $^1$H NMR(500 MHz, CDCl$_3$) δ 6.76(d, 1H, J=3.3 Hz), 6.63-6.58(m, 2H), 6.48(dd, 1H, J=8.5 Hz, J=2.8 Hz), 6.38-6.36(m, 2H), 5.60(d, 1H, J=9.8 Hz), 3.87(d, 1H, J=14.6 Hz), 3.30(d, 1H, J=14.6 Hz), 2.99(s, 3H), 2.92-2.88(m, 2H), 1.80-1.77(m, 2H), 1.01(t, 3H, J=7.5 Hz) |
| 1-1-401 | 2-NO₂Bn | H | H | n-Pr | $^1$H NMR(500 MHz, CDCl$_3$) δ 8.06-8.04(m, 1H), 7.67(d, 1H, J=7.3 Hz), 7.60-7.57(m, 1H), 7.45-7.42(m, 1H), 6.58(d, 1H, J=8.6 Hz), 6.38(dd, 1H, J=8.6 Hz, J=2.8 Hz), 6.33(d, 1H, J=9.9 Hz), 6.25(d, 1H J=2.8 Hz), 5.59(d, 1H, J=9.9 Hz), 4.64(s, 2H), 3.37(d, 1H, J=14.6 Hz), 3.29(d, 1H, J=14.6 Hz), 2.99(s, 3H), 2.92-2.88(m, 2H), 1.82-1.76(m, 2H), 1.42(s, 3H), 1.01(t, 3H, J=7.5 Hz) |
| 1-1-402 | 4-NO₂Bn | H | H | n-Pr | $^1$H NMR(500 MHz, CDCl$_3$) δ 8.19(d, 2H, J=8.6 Hz), 7.53(d, 2H, J=8.6 Hz), 6.60(d, 1H, J=8.5 Hz), 6.38(dd, 1H, J=8.5 Hz, J=2.8 Hz), 6.32(d, 1H, J=9.9 Hz), 6.26(d, 1H, J=2.8 Hz), 5.61(d, 1H, J=9.9 Hz), 4.42(s, 2H), 3.38(d, 1H, J=14.6 Hz), 3.29(d, 1H, J=14.6 Hz), 2.99(s, 3H), 2.96-2.88(m, 2H), 1.82-1.76(m, 2H), 1.42(s, 3H), 1.01(t, 3H, J=7.4 Hz) |
| 1-1-403 | 3-NO₂Bn | H | H | n-Pr | $^1$H NMR(500 MHz, CDCl$_3$) δ 8.24(s, 1H), 8.13-8.10(m, 1H), 7.72-7.69(m, 1H), 7.53-7.49(m, 1H), 6.60(d, 1H, J=8.5 Hz), 6.40(dd, 1H, J=8.5 Hz, J=2.8 Hz), 6.33(d, 1H, J=9.8 Hz), 6.28(d, 1H, J=2.8 Hz), 5.61(d, 1H, J=9.8 Hz), 4.40(s, 2H), 3.38(d, 1H, J=14.6 Hz), 3.29(d, 1H, J=14.6 Hz), 2.99(s, 3H), 2.92-2.88(m, 2H), 1.80-1.77(m, 2H), 1.42(s, 3H), 1.01(t, 3H, J=7.4 Hz) |
| 1-1-404 | PhEt | H | H | n-Pr | $^1$H NMR(500 MHz, CDCl$_3$) δ 7.33-7.20(m, 5H), 6.62(d, 1H, J=8.6 Hz), 6.47(m, 1H), 6.37(dd, 1H, J=9.9 Hz), 6.34(d, 1H, J=2.8 Hz), 5.61(d, 1H, J=9.9 Hz), 3.37-3.28(m, 4H), 3.30(s, 3H), 2.92-2.88(m, 4H), 1.81-1.78(m, 2H), 1.43(s, 3H), 1.01(t, 3H, J=7.4 Hz) |
| 1-1-405 | n-Pr | H | H | n-Pr | $^1$H NMR(500 MHz, CDCl$_3$) δ 6.62(d, 1H, J=8.5 Hz), 6.46(dd, 1H, J=8.5 Hz, J=2.7 Hz), 6.38(d, 1H, J=9.8 Hz), 6.34(d, 1H, J=2.7 Hz), 5.61(d, 1H, J=9.8 Hz), 3.36(d, 1H, J=14.6 Hz), 3.30(d, 1H, J=14.6 Hz), 3.03(t, 2H, J=7.1 Hz), 3.00(s, 3H), 2.92-2.88(m, 2H), 1.81-1.78(m, 2H), 1.64-1.60(m, 2H), 1.44(s, 3H), 1.03-0.97(m, 6H) |
| 1-1-406 | (pyridin-2-yl)CH₂C(CH₃)₂– | H | H | n-Pr | $^1$H NMR(500 MHz, CDCl$_3$) δ 8.59(d, 1H, J=4.4 Hz), 7.67-7.64(m, 1H), 7.34(d, 1H, J=7.8 Hz), 7.21-7.18(m, 1H), 6.61(d, 1H, J=8.6 Hz), 6.49(dd, 1H, J=8.6 Hz, J=2.8 Hz), 6.38-6.35(m, 2H), 5.59(d, 1H, J=9.9 Hz), 4.41(s, 2H), 3.37(d, 1H, J=14.6 Hz), 3.30(d, 1H, J=14.6 Hz), 3.00(s, 3H), 2.96-2.88(m, 2H), 1.82-1.76(m, 2H), 1.42(s, 3H), 1.01(t, 3H, J=7.4 Hz) |

-continued

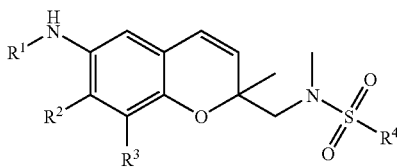

(1)

| Compd. No. | R₁ | R₂ | R₃ | R₄ | Analysis result (NMR/MS) |
|---|---|---|---|---|---|
| 1-1-407 | (3-pyridylmethyl) | H | H | n-Pr | ¹H NMR(500 MHz, CDCl₃) δ 863(d, 1H, J=1.6 Hz), 8.54-8.52(m, 1H), 7.11(d, 1H, J=7.9 Hz), 7.30-7.26(m, 2H), 6.61(d, 1H, J=8.5 Hz), 6.44(dd, 1H, J=8.6 Hz, J=2.8 Hz), 6.38(d, 1H, J=9.9 Hz), 6.31(d, 1H, J=2.8 Hz), 5.61(d, 1H, J=9.9 Hz), 4.32(s, 2H), 3.38(d, 1H, J=14.6 Hz), 3.30(d, 1H, J=14.6 Hz), 2.99(s, 3H), 2.92-2.88(m, 2H), 1.81-1.76(m, 2H), 1.43(s, 3H), 1.01(t, 3H, J=7.4 Hz) |
| 1-1-408 | (4-pyridylmethyl) | H | H | n-Pr | ¹H NMR(500 MHz, CDCl₃) δ 8.56(d, 2H, J=5.0 Hz), 7.30(d, 2H, J=5.0 Hz), 6.60(d, 1H, J=8.5 Hz), 6.38(dd, 1H, J=8.5 Hz, J=2.5 Hz), 6.33(d, 1H, J=9.9 Hz), 6.26(d, 1H, J=2.5 Hz), 5.61(d, 1H, J=9.9 Hz), 4.33(s, 2H), 3.38(d, 1H, J=14.6 Hz), 3.29(d, 1H, J=14.6 Hz), 2.99(s, 3H), 2.92-2.88(m, 2H), 1.82-1.76(m, 2H), 1.42(s, 3H), 1.01(t, 3H, J=7.4 Hz) |
| 1-1-409 | (4-(diethoxymethyl)benzyl) | H | H | n-Pr | ¹H NMR(500 MHz, CDCl₃) δ 7.44(d, 2H, J=8.0 Hz), 7.35(d, 2H, J=8.0 Hz), 7.60(d, 1H, J=8.5 Hz), 6.45(d, 1H, J=2.8 Hz), 6.35(d, 1H, J=9.7 Hz), 6.33(d, 1H, J=2.8 Hz), 5.60(d, 1H, J=9.7 Hz), 4.27(s, 2H), 3.63-3.60(m, 2H), 3.56-3.53(m, 2H), 3.33-3.30(m, 2H), 3.00(s, 3H), 2.92-2.88(m, 2H), 1.82-1.76(m, 2H), 1.43(s, 3H), 1.26-1.22(m, 6H), 1.01(t, 3H, J=7.4 Hz) |
| 1-1-410 | (2-thienylmethyl) | H | H | n-Pr | ¹H NMR(500 MHz, CDCl₃) δ 7.22-7.20(m, 1H), 7.00-6.99(m, 1H), 6.97-6.96(m, 1H), 6.62(d, 1H, J=8.6 Hz), 6.50(d, 1H, 2.8 Hz), 6.38-6.35(m, 2H), 6.51(d, 1H, J=9.9 Hz), 4.45(s, 2H), 3.37(d, 1H, J=14.6 Hz), 3.30(d, 1H, J=14.6 Hz), 2.92-2.88(m, 2H), 1.82-1.76(m, 2H), 1.43(s, 3H), 1.01(t, 3H, J=7.4 Hz) |
| 1-1-411 | (3-thienylmethyl) | H | H | n-Pr | ¹H NMR(500 MHz, CDCl₃) δ 7.30-7.29(m, 1H), 7.19(s, 1H), 7.28-7.06(m, 1H), 6.62(d, 1H, J=8.5 Hz), 6.48-6.46(m, 1H), 6.38-6.34(m, 2H), 5.61(d, 1H, J=9.8 Hz), 4.27(s, 2H), 3.38(d, 1H, J=14.6 Hz), 3.30(d, 1H, J=14.6 Hz), 2.30(s, 3H), 2.92-2.88(m, 2H), 1.82-1.76(m, 2H), 1.43(s, 3H), 1.01(t, 3H, J=7.4 Hz) |
| 1-1-412 | (4-acetoxybenzyl) | H | H | nPr | m/z 459 [M + H]⁺ |
| 1-1-413 | 4-ClBn | H | H | nPr | m/z 435 [M + H]⁺ |
| 1-1-414 | HOBn | H | H | n-Pr | m/z 417 [M + H]⁺ |
| 1-2-1 | 4-MeOBn | Me | H | Ph | ¹H NMR(500 MHz, CDCl₃) δ 7.80-7.71(m, 2H), 7.62-7.41(m, 3H), 7.31-7.22(m, 2H), 6.91-6.80(m, 2H), 6.57(d, 1H, J=8.5 Hz), 6.45-6.31(m, 2H), 5.62(d, 1H, J=9.8 Hz), 4.17(s, 2H), 3.80(s, 3H), 3.21(d, 1H, J=14.2 Hz), 3.13(d, 1H, J=14.2 Hz), 2.88(s, 3H), 2.10(s, 3H), 1.50(s, 3H) |
| 1-2-2 | 3-MeOBn | Me | H | Ph | ¹H NMR(500 MHz, CDCl₃) δ 7.79-7.73(m, 2H), 7.61-7.42(m, 3H), 7.28-7.20(m, 1H), 6.92(d, 2H, J=7.1 Hz), 6.90-6.76(m, 1H), 6.56(d, 1H, J=8.5 Hz), 6.44-6.30(m, 2H), 5.65(d, 1H, J=9.8 Hz), 4.22(s, 2H), 3.81(s, 3H), 3.22(d, 1H, |

-continued

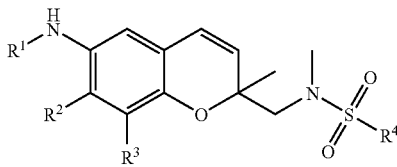

(1)

| Compd. No. | R₁ | R₂ | R₃ | R₄ | Analysis result (NMR/MS) |
|---|---|---|---|---|---|
| | | | | | J=14.2 Hz), 3.16(d, 1H, J=14.2 Hz), 2.89(s, 3H), 2.10(s, 3H), 1.50(s, 3H) |
| 1-2-3 | 2-MeOBn | Me | H | Ph | $^1$H NMR(500 MHz, CDCl$_3$) δ 7.78-7.73(m, 2H), 7.60-7.44(m, 3H), 7.30-7.20(m, 2H), 6.93-6.86(m, 2H), 6.56(d, 1H, J=8.5 Hz), 6.39-6.32(m, 2H), 5.63(d, 1H, J=9.7 Hz), 4.25(s, 2H), 3.85(s, 3H), 3.23(d, 1H, J=14.4 Hz), 3.14(d, 1H, J=14.4 Hz), 2.87(s, 3H), 2.11(s, 3H), 1.51(s, 3H) |
| 1-2-4 | Bn | Me | H | Ph | $^1$H NMR(500 MHz, CDCl$_3$) δ 7.78-7.73(m, 2H), 7.61-7.44(m, 3H), 7.38-7.23(m, 5H), 6.57(d, 1H, J=8.5 Hz), 6.44-6.30(m, 2H), 5.64(d, 1H, J=9.8 Hz), 4.25(s, 2H), 3.23(d, 1H, J=14.4 Hz), 3.14(d, 1H, J=14.4 Hz), 2.87(s, 3H), 2.11(s, 3H), 1.51(s, 3H) |
| 1-2-5 | 4-tert-BuBn | Me | H | Ph | $^1$H NMR(500 MHz, CDCl$_3$) δ 7.79-7.72(m, 2H), 7.51-7.42(m, 3H), 7.39-7.25(m, 4H), 6.58(d, 1H, J=8.3 Hz), 6.45-6.31(m, 1H), 5.64(d, 1H, J=9.9 Hz), 4.21(s, 2H), 3.24(d, 1H, J=14.4 Hz), 3.15(d, 1H, J=14.4 Hz), 2.89(s, 3H), 2.11(s, 3H), 1.52(s, 3H) |
| 1-2-6 | 3-ClBn | Me | H | Ph | $^1$H NMR(500 MHz, CDCl$_3$) δ 7.79-7.73(m, 2H), 7.61-7.44(m, 3H), 7.31(s, 1H), 7.26-7.23(m, 3H), 6.57(d, 1H, J=8.5 Hz), 6.41-6.26(m, 2H), 5.64(d, 1H, J=9.8 Hz), 4.24(s, 2H), 3.23(d, 1H, J=14.4 Hz), 3.16(d, 1H, J=14.4 Hz), 2.88(s, 3H), 2.11(s, 3H), 1.51(s, 3H) |
| 1-2-7 | 4-CNBn | Me | H | Ph | $^1$H NMR(500 MHz, CDCl$_3$) δ 7.78-7.71(m, 2H), 7.63-7.26(m, 7H), 6.55(d, 1H, J=8.5 Hz), 6.37-6.22(m, 2H), 5.64(d, 1H, J=9.8 Hz), 4.34(s, 2H), 3.90(br, 1H), 3.18(s, 2H), 2.88(s, 3H), 2.11(s, 3H), 1.49(s, 3H) |
| 1-2-8 | 4-EtOBn | Me | H | Ph | $^1$H NMR(500 MHz, CDCl$_3$) δ 7.77-7.72(m, 2H), 7.61-7.44(m, 3H), 7.31-7.23(m, 2H), 6.84(d, 2H, J=8.5 Hz), 6.57(d, 1H, J=8.3 Hz), 6.44-6.30(m, 1H), 5.64(d, 1H, J=9.8 Hz), 4.15(s, 2H), 4.09-3.97(m, 4H), 3.23(d, 1H, J=14.2 Hz), 3.14(d, 1H, J=14.2 Hz), 2.87(s, 3H), 2.10(s, 3H), 1.52(s, 3H), 1.41(t, 3H, J=7.1 Hz) |
| 1-2-9 | 2-FBn | Me | H | Ph | $^1$H NMR(500 MHz, CDCl$_3$) δ 7.78-7.72(m, 2H), 7.61-7.44(m, 3H), 7.39-7.28(m, 1H), 7.26-7.19(m, 1H), 7.19-6.99(m, 2H), 6.59(d, 1H, J=8.5 Hz), 6.45-6.30(m, 2H), 5.63(d, 1H, J=9.8 Hz), 4.31(s, 2H), 3.23(d, 1H, J=14.4 Hz), 3.14(d, 1H, J=14.4 Hz), 2.86(s, 3H), 2.11(s, 3H), 1.51(s, 3H) |
| 1-2-10 | 4-FBn | Me | H | Ph | $^1$H NMR(500 MHz, CDCl$_3$) δ 7.78-7.73(m, 2H), 7.61-7.44(m, 3H), 7.37-7.25(m, 2H), 7.09-6.96(m, 2H), 6.57(d, 1H, J=8.5 Hz), 6.42-6.28(m, 2H), 5.65(d, 1H, J=9.8 Hz), 4.21(s, 2H), 3.23(d, 1H, J=14.4 Hz), 3.15(d, 1H, J=14.4 Hz), 2.86(s, 3H), 2.11(s, 3H), 1.51(s, 3H) |
| 1-2-11 | 3-FBn | Me | H | Ph | $^1$H NMR(500 MHz, CDCl$_3$) δ 7.78-7.73(m, 2H), 7.61-7.44(m, 3H), 7.34-7.23(m, 1H), 7.14-7.03(m, 2H), 6.99-6.89(m, 1H), 6.57(d, 1H, J=8.5 Hz), 6.42-6.27(m, 2H), 5.64(d, 1H, J=9.8 Hz), 4.26(s, 2H), 3.23(d, 1H, J=14.3 Hz), 3.14(d, 1H, J=14.3 Hz), 2.87(s, 3H), 2.11(s, 3H), 1.51(s, 3H) |
| 1-2-12 | i-Bu | Me | H | Ph | $^1$H NMR(500 MHz, CDCl$_3$) δ 7.79-7.72(m, 2H), 7.60-7.44(m, 3H), 6.57(d, 1H, J=8.5 Hz), 6.41-6.35(m, 1H), 6.27(d, 1H, J=2.5 Hz), 5.63(d, 1H, J=9.8 Hz), 3.23(d, 1H, J=14.2 Hz), 3.13(d, 1H, J=14.2 Hz), 2.87-2.82(m, 5H), 2.11(s, 3H), 1.51(s, 2H), 0.96(d, 6H, J=6.7 Hz) |

-continued

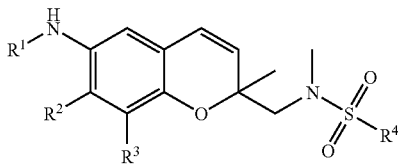

(1)

| Compd. No. | R₁ | R₂ | R₃ | R₄ | Analysis result (NMR/MS) |
|---|---|---|---|---|---|
| 1-2-13 | (5-methylthiophen-2-yl)methyl | Me | H | Ph | ¹H NMR(500 MHz, CDCl₃) δ 7.79-7.72(m, 2H), 7.60-7.43(m, 3H), 6.78-6.73(m, 1H), 6.60-6.55(m, 2H), 6.34-6.32(m, 1H), 5.64(d, 1H, J=9.8 Hz), 4.33(s, 2H), 3.23(d, 1H, J=14.3 Hz), 3.14(d, 1H, J=14.3 Hz), 2.86(s, 3H), 2.43(s, 3H), 2.11(s, 3H), 1.51(s, 3H) |
| 1-2-14 | 2-NO₂Bn | Me | H | Ph | ¹H NMR(500 MHz, CDCl₃) δ 8.11-8.00(m, 1H), 7.77-7.70(m, 2H), 7.66-7.35(m, 6H), 6.53(d, 1H, J=8.5 Hz), 6.36-6.30(m, 1H), 6.22(d, 1H, J=2.8 Hz), 5.63(d, 1H, J=9.8 Hz), 4.97(s, 2H), 4.61(s, 3H), 3.17(s, 2H), 2.85(s, 3H), 2.11(s, 3H), 1.48(s, 3H) |
| 1-2-15 | 4-NO₂Bn | Me | H | Ph | ¹H NMR(500 MHz, CDCl₃) δ 8.16(d, 2H, J=8.8 Hz), 7.77-7.72(m, 2H), 7.61-7.43(m, 5H), 6.55(d, 1H, J=8.5 Hz), 6.37-6.29(m, 1H), 5.64(d, 1H, J=10.0 Hz), 4.38(s, 2H), 3.99(br, 1H), 3.18(s, 2H), 2.85(s, 3H), 2.11(s, 3H), 1.48(s, 3H) |
| 1-2-16 | 3-NO₂Bn | Me | H | Ph | ¹H NMR(500 MHz, CDCl₃) δ 8.21(s, 1H), 8.12-8.07(m, 2H), 7.76-7.66(m, 3H), 7.56-7.44(m, 4H), 6.55(d, 1H, J=8.5 Hz), 6.39-6.30(m, 1H), 6.25(d, 1H, J=2.6 Hz), 5.64(d, 1H, J=9.8 Hz), 4.37(s, 2H), 3.18(s, 2H), 2.85(s, 3H), 2.11(s, 3H), 1.50(s, 3H) |
| 1-2-17 | PhEt | Me | H | Ph | ¹H NMR(500 MHz, CDCl₃) δ 7.78-7.72(m, 2H), 7.56-7.43(m, 3H), 7.35-7.18(m, 5H), 6.57(d, 1H, J=8.3 Hz), 6.41-6.34(m, 1H), 6.28(d, 1H, J=2.6 Hz), 5.63(d, 1H, J=9.8 Hz), 3.82(t, 3H, J=7.4 Hz), 3.23(d, 1H, J=12.4 Hz), 3.13(d, 1H, J=12.4 Hz), 2.91-2.16(m, 5H), 2.11(s, 3H), 1.51(s, 3H) |
| 1-2-18 | n-Pr | Me | H | Ph | ¹H NMR(500 MHz, CDCl₃) δ 7.77-7.72(m, 2H), 7.56-7.43(m, 3H), 6.56(d, 1H, J=8.2 Hz), 6.41-6.34(m, 1H), 6.27(d, 1H, J=2.8 Hz), 5.63(d, 1H, J=10.0 Hz), 3.22(d, 1H, J=14.3 Hz), 3.14(d, 1H, J=14.3 Hz), 2.99(t, 2H, J=7.1 Hz), 2.86(s, 3H), 2.11(s, 3H), 1.65-1.54(m, 2H), 1.51(s, 3H), 0.97(t, 3H, J=7.3 Hz) |
| 1-2-19 | (pyridin-2-yl)methyl | Me | H | Ph | ¹H NMR(500 MHz, CDCl₃) δ 8.57-8.54(m, 1H), 7.77-7.71(m, 2H), 7.67-7.54(m, 1H), 7.53-7.42(m, 3H), 7.30(d, 1H, J=7.9 Hz), 7.19-7.13(m, 1H), 6.56(d, 1H, J=8.5 Hz), 6.47-6.31(m, 2H), 5.62(d, 1H, J=10.0 Hz), 4.36(s, 2H), 3.22(d, 1H, J=14.3 Hz), 3.14(d, 1H, J=14.3 Hz), 2.86(s, 3H), 2.11(s, 3H), 1.50(s, 3H) |
| 1-2-20 | (pyridin-3-yl)methyl | Me | H | Ph | ¹H NMR(500 MHz, CDCl₃) δ 8.59(m, 1H), 8.50(d, 1H, J=4.1 Hz), 7.77-7.64(m, 3H), 7.60-7.42(m, 3H), 7.28-7.20(m, 1H), 6.56(d, 1H, J=8.5 Hz), 6.28(d, 1H, J=2.6 Hz), 5.63(d, 1H, J=9.8 Hz), 4.27(s, 2H), 3.21(d, 1H, J=15.2 Hz), 3.14(d, 1H, J=15.2 Hz), 2.85(s, 3H), 2.11(s, 3H), 1.49(s, 3H) |
| 1-2-21 | (pyridin-4-yl)methyl | Me | H | Ph | ¹H HMR(500 MHz, CDCl₃) δ 8.55-8.51(m, 2H), 7.77-7.72(m, 2H), 7.56-7.43(m, 3H), 7.28-7.25(m, 2H), 6.55(d, 1H, J=8.5 Hz), 6.37-6.29(m, 1H), 6.23(d, 1H, J=2.6 Hz), 5.64(d, 1H, J=10.0 Hz), 4.29(s, 2H), 3.18(s, 2H), 2.85(s, 3H), 2.11(s, 3H), 1.49(s, 3H) |

-continued

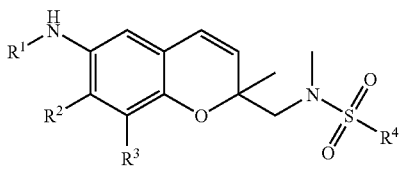

(1)

| Compd. No. | R₁ | R₂ | R₃ | R₄ | Analysis result (NMR/MS) |
|---|---|---|---|---|---|
| 1-2-22 | 4-(diethoxymethyl)benzyl | Me | H | Ph | m/z 551 [M + H]⁺ |
| 1-2-23 | 2-thienylmethyl | | Me | Ph | ¹NMR(500 MHz, CDCl₃) δ7.77-7.72(m, 2H), 7.59-7.41(m, 4H), 7.32(d, 2H J=8.3 Hz), 6.55(d, 1H, J=8.5 Hz), 6.42-6.28(m, 2H), 5.63(d, 1H, J=9.8 Hz), 4.23(s, 2H), 3.70-3.44(m, 4H), 3.23(d, 1H, J=14.2 Hz), 3.14(d, 1H, J=14.2 Hz), 2.86(s, 3H), 2.11(s, 3H), 1.50(s, 3H), 1.23(t, 3H, J=7.0 Hz) |
| 1-2-24 | 3-thienylmethyl | | Me | | m/z 455 [M + H]⁺ |
| 1-2-25 | 4-acetoxybenzyl | | Me | | m/z 507 [M + H]⁺ |
| 1-2-26 | 4-ClBn | | Me | | m/z 484 [M + H]⁺ |
| 1-2-27 | 4-HOBn | | Me | | m/z 465 [M + H]⁺ |

TESTING EXAMPLE

Bioassay Test 1. 5-Lipoxygenase enzyme assay

1) Bioassay Using FOX Reagent

Each test compound (final concentration=1 μM) was added to a lysate (7 μg) obtained from 5-LO expressed insect cells and reaction was performed at room temperature for 3 minutes. Then, arachidonic acid (40 μM) was added as enzyme substrate and reaction was further performed at room temperature for 4 minutes. 100 μL of a FOX reagent (sulfuric acid 25 mM, xylenol orange 100 μM, FeSO₄ 100 μM, methanol/water=9:1) was added thereto and then, after 5 minutes, absorbance was measured at 575 nm.

2) Spectroscopic Assay (234 nm)

Each test compound (final concentration=1 μM) was added to a lysate (7 μg) obtained from 5-LO expressed insect cells and reaction was performed at room temperature for 3 minutes. Then, a reaction buffer solution (50 mM Tris buffer, pH 7.4, 0.4 mM CaCl₂, 24 μg/mL phosphatidylcholine, 40 μM arachidonic acid) was added thereto and change of absorbance was measured at 234 nm over a 4-minute period.

2. LTB4 Cell-Based Assay

Rat basophilic leukemia (RBL-1) cells were inoculated at a 24-well plate to a final concentration of 7.5×10⁵ cells/well and incubated for 2 hours, so that they adhered to the bottom of the plate. After 2 hours, the cells were treated with A23187 (final concentration=10 μM) for 10 minutes and then each test compound was added thereto (final concentration=10 μM) and reaction was performed for 10 minutes. The well plate was centrifuged at 1,500 g for 20 minutes to isolate the supernatant and then the amount of LTB4 of the supernatant was measured with ELISA analysis.

3. In Vivo Bioassay (Mouse Ear Edema Model)

The inside of the right ear of an ICR mouse (6 weeks old) was treated with 2 mg of arachidonic acid dissolved in 20 μL of acetone for 1 hour to induce an inflammation.

After 1 hour, the difference of thickness T (%) between the arachidonic acid-treated right ear and the non-treated left ear was measured with a microgauge.

Further, myeloperoxidase (MPO) activity was measured in order to measure the amount of neutrophil penetrated into the tissue as a primary marker for induced inflammation. The tissue obtained from the arachidonic acid-treated right ear was homogenized in a 50 mM phosphate buffer solution (pH 6.0) containing 0.5% hexadecyltrimethylammonium bromide (HTAB), centrifuged and then the MPO activity (MPO %) of the supernatant was measured.

To measure in vivo activity of each test compound, each compound was dissolved in 0.5% methylcellulose (10 mL/kg) and orally administered to a mouse 1 hour before treatment with arachidonic acid. Then, arachidonic acid was treated for 1 hour and the thickness of ear and MPO activity were measured. In vivo activity of each test compound was estimated by comparing the test result with that of a control which was treated only with arachidonic acid, without the test compound. Table 2

Formulation Form 1: Tablet (Direct Pressurization)

5.0 mg of the active ingredient was sieved, mixed with 14.1 mg of lactose, 0.8 mg of crosspovidone USNF and 0.1 mg of magnesium stearate, and the mixture was directly pressurized to obtain a tablet.

Formulation Form 2: Tablet (Wetting Assembly)

5.0 mg of an active ingredient was sieved and mixed with 16.0 mg of lactose and 4.0 mg of starch. 0.3 mg of polysorbate 80 dissolved in pure water was added to the mixture in a suitable amount and then the mixture was made into micro-particulates. The micro-particulates were dried, sieved and then mixed with 2.7 mg of colloidal silicon dioxide and 2.0 mg of magnesium stearate. The micro-particulates were pressurized to obtain a tablet.

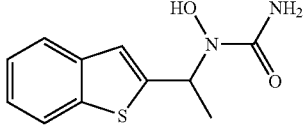

| Test compound | 5-LO enzyme assay (% inhibition, at 1 μM) | Cell-based assay (% inhibition, at 1 μM) | Mouse ear edema model (in vivo assay) |
|---|---|---|---|
| Zilutone | 85 | 80 | Thickness 67% MPO 38% |
| 1-1-1 | 86 | 82 | Thickness 62% MPO 34% |
| 1-1-4 | 78 | 72 | |
| 1-1-7 | 80 | 71 | |
| 1-1-10 | 87 | 81 | Thickness 60% MPO 27% |
| 1-1-11 | 73 | 58 | |
| 1-1-13 | 76 | 54 | |
| 1-1-23 | 79 | 63 | Thickness 56% MPO 24% |
| 1-1-24 | 44 | 34 | |
| 1-1-40 | 45 | 38 | |
| 1-1-51 | 48 | 36 | |
| 1-1-67 | 77 | 49 | |
| 1-1-78 | 59 | 40 | |
| 1-1-103 | 63 | 52 | |
| 1-1-132 | 47 | 35 | |
| 1-1-163 | 61 | 43 | |
| 1-1-183 | 45 | 38 | |
| 1-1-217 | 70 | 56 | |
| 1-1-244 | 67 | 41 | |
| 1-1-256 | 79 | 63 | |
| 1-1-288 | 64 | 39 | |
| 1-1-298 | 73 | 47 | |
| 1-2-7 | 79 | 61 | |
| 1-2-23 | 80 | 74 | |

As seen in Table 2, it was found that the compounds of the present invention are capable of effectively inhibiting the 5-LO activity and some of them showed such a powerful inhibitory effect as to compete with Zilutone in enzyme, cell and animal experiments. Since the compounds of the present invention have potent inhibition effect to 5-LO activity in spite of a unique structure entirely different from that of Zilutone, they can be effectively used to develop a noble drug for preventing or treating chronic inflammation, rheumatoid arthritis, colitis, asthma, psoriasis, etc.

Hereunder are given formulation examples comprising the compounds of the present invention as active ingredient. They and are only for the understanding of the invention and the invention is not limited to or by them.

Formulation Form 3: Powder and Capsule 5.0 mg of the active ingredient was sieved and mixed with 14.8 mg of lactose, 10.0 mg of polyvinyl pyrrolidone and 0.2 mg of magnesium stearate. The mixture was filled into a hard gelatin capsule No. 5 using a proper apparatus.

Formulation Form 4: Injection 100 mg of the active ingredient, 180 mg of mannitol and 26 mg of $Na_2HPO_4.12H_2O$ were dissolved in 2,974 mg of distilled water to obtain an injection.

INDUSTRIAL APPLICABILITY

As apparent from the previous description, while the conventional processes perform multi-step reactions in solution and require several treatment and purification steps after the reactions, the method for preparing 6-alkylamino-2-methyl-2'-(N-methyl substituted sulfonamido)methyl-2H-1-benzopyran derivative using a solid-phase parallel synthetic method in accordance with the present invention makes it possible to significantly reduce the number of treatment and purification steps and to effectively construct a large amount of drug-like libraries. Particularly, according to the finding of the present inventors, when two rounds of N-alkylation are carried out via a parallel synthetic method using 6-amino-2-methyl-2'-(Fmoc protected methylamino)methyl-2H-1-benzopyran resin coupled with a BAL linker on a solid support represented by the formula 4 and 6-alkylamino-2-methyl-2'-(methylamino)methyl-2H-1-benzopyran resin represented by the formula 6, it is possible to conduct tens or hundreds of reactions and purification steps at the same time, which is very useful in effectively synthesizing various 6-alkylamino-2-methyl-2'-(N-methyl substituted sulfonamido)methyl-2H-1-benzopyran derivatives in a short period of time.

Accordingly, the present invention establishes the technology for construction of a 6-alkylamino-2-methyl-2'-(N-methyl substituted sulfonamido)methyl-2H-1-benzopyran library using a solid-phase parallel synthetic method, which highlights the applicability of combinatorial chemical synthetic technique. Particularly, a high inhibitory effect to 5-LO activity of a target compound is useful in the development of a drug for preventing and treating diseases such as chronic inflammation, arthritis, and rheumatism.

While the present invention has been described in detail with reference to the preferred embodiments, those skilled in the art will appreciate that various modifications and substitutions can be made thereto without departing from the spirit and scope of the present invention as set forth in the appended claims.

The invention claimed is:

1. A 6-alkylamino-2-methyl-2'-(N-methyl substituted sulfonamido)methyl-2H-1-benzopyran compound represented by the formula 1:

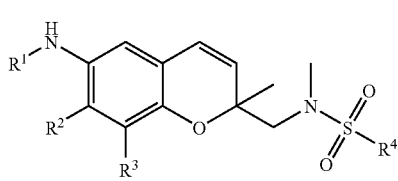

(1)

wherein
R$^1$ is C$_1$-C$_{10}$ alkyl; phenyl; phenyl substituted with a substituent selected from the group consisting of C$_1$-C$_6$ alkyl, C$_1$-C$_6$ acyloxy, C$_1$-C$_{10}$ alkoxyalkyl and C$_1$-C$_{10}$ dialkoxyalkyl; benzyl; benzyl substituted with a substituent selected from the group consisting of halogen, nitro, cyano, hydroxy, C$_1$-C$_6$ alkyl and C$_1$-C$_6$ alkoxy; phenethyl; pyridylmethyl; thiophenemethyl; or thiophenemethyl substituted with C$_1$-C$_6$ alkyl,
each of R$^2$ and R$^3$ is a hydrogen atom; or C$_1$-C$_6$ alkyl and
R$^4$ is C$_1$-C$_{10}$ alkyl; phenyl; phenyl substituted with a substituent selected from the group consisting of halogen, C$_1$-C$_6$ alkyl and C$_1$-C$_6$ alkoxy; benzyl; or thiophene.

2. The 6-alkylamino-2-methyl-2'-(N-methyl substituted sulfonamido)methyl-2H-1-benzopyran derivative compound represented by the formula 1 according to claim 1, wherein
R$^1$ is C$_1$-C$_6$ alkyl; phenyl; phenyl substituted with a substituent selected from the group consisting of C$_1$-C$_4$ alkyl, acetyl and diethoxymethyl; benzyl; benzyl substituted with a substituent selected from the group consisting of halogen, nitro, cyano, hydroxy, C$_1$-C$_4$ alkyl and C$_1$-C$_4$ alkoxy; phenethyl; pyridylmethyl; thiophenemethyl; or thiophenemethyl substituted with C$_1$-C$_4$ alkyl,
each of R$^2$ and R$^3$ is a hydrogen atom, or C$_1$-C$_4$ alkyl and
R$^4$ is C$_1$-C$_6$ alkyl; phenyl; phenyl substituted with a substituent selected from the group consisting of halogen, C$_1$-C$_4$ alkyl and C$_1$-C$_4$ alkoxy; benzyl; or thiophene.

3. A method of preparing a 6-alkylamino-2-methyl-2'-(N-methyl substituted sulfonamido)methyl-2H-1-benzopyran compound represented by the formula 1 comprising the 5 steps of:

synthesizing a 6-amino-2-methyl-2'-(Fmoc protected methylamino)methyl-2H-1-benzopyran resin represented by the formula 4 by introducing 6-amino-2-methyl-2'-(Fmoc protected methylamino)methyl-2H-7,8-disubstituted benzopyran represented by the formula 3 to a solid support coupled with backbone amide linker (BAL linker) represented by the formula 2 (the first step);

synthesizing a 6-alkylamino-2-methyl-2'-(Fmoc protected methylamino)methyl-2H-1-benzopyran represented by the formula 5 by selectively introducing the R$^1$ substituent to the nitrogen atom of the 6-amino-2-methyl-2'-(Fmoc protected methylamino)methyl-2H-1-benzopyran resin represented by the formula 4 (the second step);

synthesizing a 6-alkylamino-2-methyl-2'-(methylamino)methyl-2H-1-benzopyran resin represented by the formula 6 by Fmoc deprotection of the 6-alkylamino-2-methyl-2'-(Fmoc protected methylamino)methyl-2H-1-benzopyran represented by the formula 5 with an organic base selected from the group consisting of alkylamine, pyridine and piperidine (the third step);

synthesizing a 6-alkylamino-2-methyl-2'-(N-methyl substituted sulfonamido)methyl-2H-1-benzopyran resin represented by the formula 7 by selectively introducing the R$^4$ sulfonyl substituent to the nitrogen atom of the 6-alkylamino-2-methyl-2'-(methylamino)methyl-2H-1-benzopyran resin represented by the formula 6 (the fourth step); and synthesizing a 6-alkylamino-2-methyl-2'-(N-methyl substituted sulfonamido)methyl-2H-1-benzopyran library represented by the formula 1, a final target compound, by cleaving the 6-alkylamino-2-methyl-2'-(N-methyl substituted sulfonamido)methyl-2H-1-benzopyran compound from resin represented by the formula 7 with an organic solvent containing an organic acid (the fifth step)

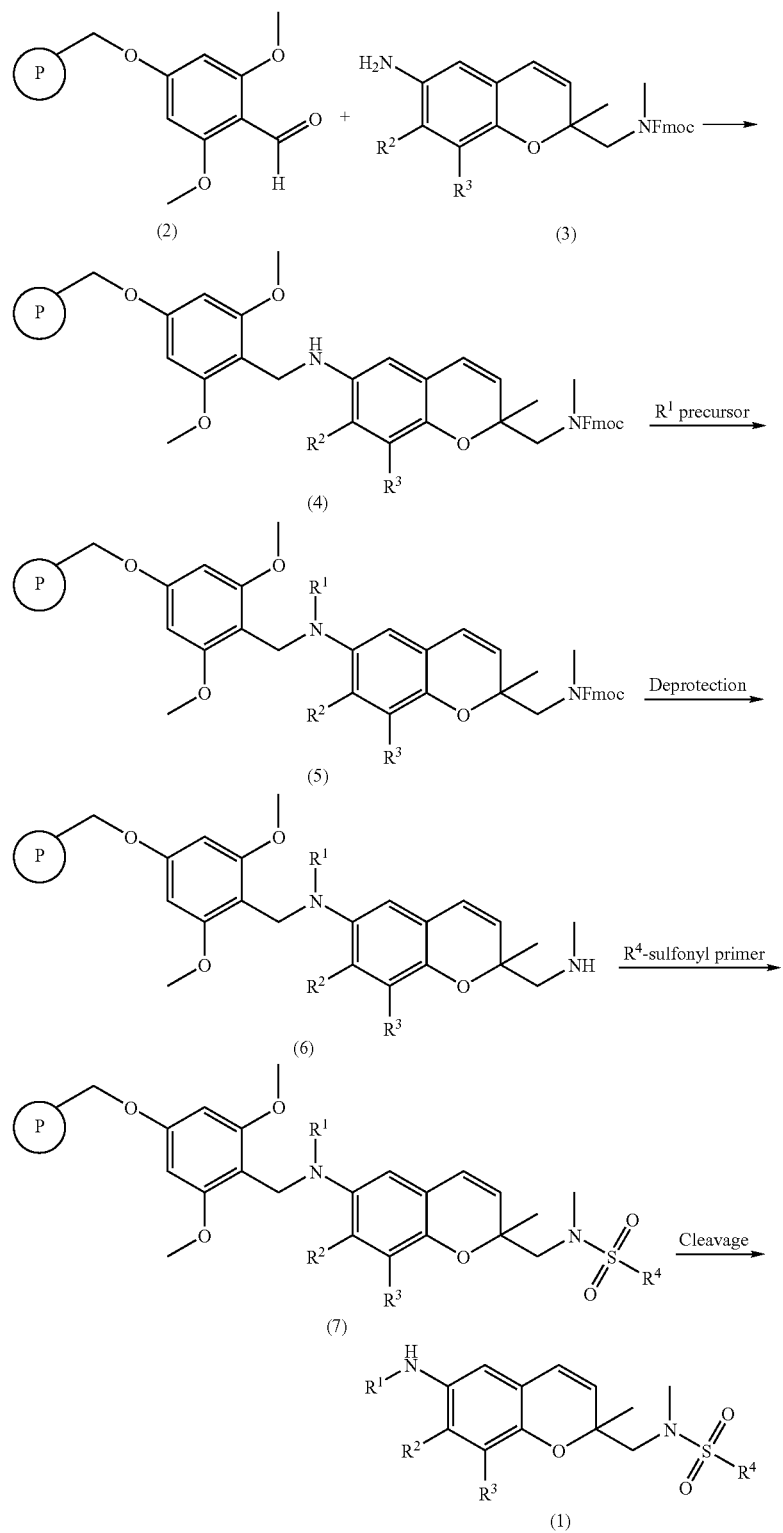

wherein, $R^1$, $R^2$, $R^3$ and $R^4$ are the same as defined in claim 1, and ⓟ is a solid support in the form of high molecular weight polymer selected from the group consisting of polystyrene-divinylbenzene, methacrylic acid-dimethylacrylamide and hydroxyl methacrylic acid.

4. A pharmaceutical composition comprising the compound of claim 1 and a pharmaceutically acceptable carrier.

* * * * *